United States Patent
Faull et al.

(10) Patent No.: US 7,125,896 B2
(45) Date of Patent: Oct. 24, 2006

(54) THIOPHENE CARBOXAMIDE COMPOUNDS AS INHIBITORS OF ENZYME IKK-2

(75) Inventors: Alan Faull, Macclesfield (GB); Craig Johnstone, Macclesfield (GB); Andrew Morley, Macclesfield (GB); Philip Jeffrey Poyser, Macclesfield (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/484,569

(22) PCT Filed: Jul. 19, 2002

(86) PCT No.: PCT/SE02/01403

§ 371 (c)(1),
(2), (4) Date: Jan. 22, 2004

(87) PCT Pub. No.: WO03/010158

PCT Pub. Date: Feb. 6, 2003

(65) Prior Publication Data

US 2004/0242573 A1 Dec. 2, 2004

(30) Foreign Application Priority Data

Jul. 25, 2001 (SE) .................................. 0102616

(51) Int. Cl.
*A61K 31/4436* (2006.01)
*C07D 409/04* (2006.01)

(52) U.S. Cl. .................................. 514/336; 546/281.4
(58) Field of Classification Search ............ 546/281.4, 546/276.4, 193; 544/364; 514/336
See application file for complete search history.

(56) References Cited

U.S. PATENT DOCUMENTS

| 6,048,880 | A * | 4/2000 | Kawai et al. ................ 514/336 |
| 2002/0002199 | A1* | 1/2002 | Jeppesen et al. ............. 514/444 |
| 2002/0107252 | A1* | 8/2002 | Baxter et al. ........... 514/252.01 |
| 2004/0024047 | A1* | 2/2004 | Callahan et al. ............. 514/438 |
| 2004/0235821 | A1* | 11/2004 | Griffiths et al. ........ 514/217.01 |
| 2006/0058522 | A1 | 3/2006 | Faull |

FOREIGN PATENT DOCUMENTS

| EP | 0853083 | 7/1998 |
| EP | 0 908 456 A1 | 4/1999 |
| GB | 1468012 | 3/1977 |
| GB | 2195634 A * | 4/1988 |
| WO | WO 98/02430 | 1/1998 |
| WO | WO 98/54116 | 12/1998 |
| WO | WO 99/46244 | 9/1999 |
| WO | WO 9946244 A1 * | 9/1999 |
| WO | WO 0071532 | 11/2000 |
| WO | WO 200158890 A1 * | 8/2001 |
| WO | WO 0198290 | 12/2001 |
| WO | WO 200198290 A2 * | 12/2001 |
| WO | WO 0230353 | 4/2002 |
| WO | WO 03/010158 A1 | 2/2003 |
| WO | WO 2003028731 A1 * | 4/2003 |
| WO | WO 2003029241 A1 * | 4/2003 |
| WO | WO 2004/063185 | 7/2004 |
| WO | WO 2004/063186 | 7/2004 |

OTHER PUBLICATIONS

Chen, Guoqing and Goeddel, David, "TNF-R1 Signaling: A Beautiful Pathway," Science, vol. 296, pp. 1634-1635 (May 31, 2002) at p. 1634, col. 1, lines 9-19, lines 32-36 and Figure 1; also p. 1635, col. 1, lines 2-17.*
Awada, A., et al., "The pipeline of new anticancer agents for breast cancer treatment in 2003," Critical Reviews in Oncology/Hematology, vol. 48, pp. 45-63 at p. 46, 2nd column, line 3, et seq.*
Compston, A., and Coles, A., "Multiple sclerosis," The Lancet, vol. 359, pp. 1221-1231 (Apr. 6, 2002), at p. 1224, col. 2, lines 21 et seq. (causes of M.S.); p. 1226, lines 10 et seq. (treatment of M.S.); and p. 1221, lines 18-36.*
Hartung, H., et al., "What do we know about the mechanism of action of disease-modifying treatments in MS?" J. Neurol., vol. 251(suppl. 5), pp. V/12-V/29 (2004), at p. V/13, lines 26-30; and p. V/16, col. 2, lines 3-10.*
Zayed et al., "Studies on 5-Aminopyrazole Derivatives. Synthesis of Some New Fused Pyrazole Derivatives", *Monatshefte für Chemie* 115:431-436 (1984).
U.S. Appl. No. 09/868,884, filed Feb. 5, 2002, Baxter et al.
U.S. Appl. No. 10/484,645, filed Jan. 22, 2004, Griffiths et al.

* cited by examiner

*Primary Examiner*—Kamal A. Saeed
*Assistant Examiner*—Nyeemah Grazier
(74) *Attorney, Agent, or Firm*—Fish & Richardson P.C.

(57) ABSTRACT

The invention relates to thiophene carboxanmides of formula (I), wherein A, $R^1$, $R^2$, $R^3$, n and X are as defined in the specification, processes and intermediates used in their preparation, pharmaceutical compositions containing them and their use in therapy.

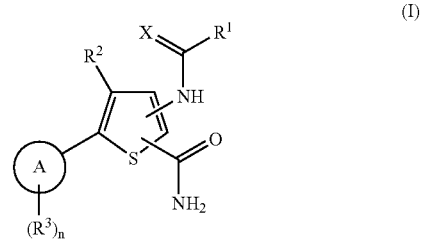

(I)

12 Claims, No Drawings

THIOPHENE CARBOXAMIDE COMPOUNDS AS INHIBITORS OF ENZYME IKK-2

This application claims priority under 35 U.S.C. §371 to a national phase filing of international application number PCT/SE02/01403, filed Jul. 19, 2002, which claims priority to SE 0102616-0, filed Jul. 25, 2001. These applications are incorporated by reference herein.

FIELD OF THE INVENTION

The present invention relates to thiophene carboxamide derivatives, processes and intermediates used in their preparation, pharmaceutical compositions containing them and their use in therapy.

BACKGROUND OF THE INVENTION

The NF-κB (nuclear factor κB) family is composed of homo- and heterodimers of the Rel family of transcription factors. A key role of these transcription factors is to induce and coordinate the expression of a broad spectrum of pro-inflammatory genes including cytokines, chemokines, interferons, MHC proteins, growth factors and cell adhesion molecules (for reviews see Verma et. al., Genes Dev. 9:2723–35, 1995; Siebenlist et. al., Ann. Rev. Cell. Biol. 10:405–455, 1994; Bauerle and Henkel, Ann. Rev. Immunol., 12:141–179, 1994; Barnes and Karin, New Engl. J. Med., 336:1066–1071, 1997).

The most commonly found Rel family dimer complex is composed of p50 NFkB and p65 RelA (Baeuerle and Baltimore, Cell 53:211–217, 1988; Baeuerle and Baltimore, Genes Dev. 3:1689–1698, 1989). Under resting conditions NF-κB dimers are retained in the cytoplasm by a member of the IκB family of inhibitory proteins (Beg et. al., Genes Dev., 7:2064–2070, 1993; Gilmore and Morin, Trends Genet. 9:427–433, 1993; Haskil et. al., Cell 65:1281–1289, 1991). However, upon cell activation by a variety of cytokines or other external stimuli, IκB proteins become phosphorylated on two critical serine residues (Traenckner et. al., EBMO J., 14:2876, 1995) and are then targeted for ubiquitination and proteosome-mediated degradation (Chen, Z. J. et. al., Genes and Dev. 9:1586–1597, 1995; Scherer, D.C. et. al., Proc. Natl. Acad. Sci. USA 92:11259–11263, 1996; Alkalay, I. et. al., Proc. Natl. Acad. Sci. USA 92:10599–10603, 1995). The released NF-κB is then able to translocate to the nucleus and activate gene transcription (Beg et. al., Genes Dev., 6:1899–1913, 1992).

A wide range of external stimulii have been shown to be capable of activating NF-κB (Baeuerle, P. A., and Baichwal, V. R., Adv. Immunol., 65:111–136, 1997). Although the majority of NF-κB activators result in IκB phosphorylation, it is clear that multiple pathways lead to this key event. Receptor-mediated NF-κB activation relies upon specific interactions between the receptor and adapter/signalling molecules (for example, TRADD, RIP, TRAF, MyD88) and associated kinases (IRAK, NIK) (Song et. al., Proc. Natl. Acad. Sci. USA 94:9792–9796, 1997; Natoli et. al., JBC 272:26079–26082, 1997). Environmental stresses such as UV light and γ-radiation appear to stimulate NF-κB via alternative, less defined, mechanisms.

Recent publications have partially elucidated the NF-κB activation. This work has identified three key enzymes which regulate specific IκB/NF-κB interactions: NF-κB inducing kinase (NIK) (Boldin et. al., Cell 85:803–815, 1996), IκB kinase-1 (IKK-1) (Didonato et. al., Nature 388: 548, 1997; Regnier at. al., Cell 90:373 1997) and IκB kinase-2 (IKK-2) (Woronicz et. al., Science 278:866, 1997; Zandi et. al., Cell 91:243, 1997).

NIK appears to represent a common mediator of NF-κB signalling cascades triggered by tumour necrosis factor and interleukin-1, and is a potent inducer of IκB phosphorylation. However NIK is unable to phosphorylate IκB directly.

IKK-1 and IKK-2 are thought to lie immediately downstream of NIK and are capable of directly phosphorylating all three IκB sub-types. IKK-1 and IKK-2 are 52% identical at the amino acid level but appear to have similar substrate specificities; however, enzyme activities appear to be different: IKK-2 is several-fold more potent than IKK-1. Expression data, coupled with mutagenesis studies, suggest that IKK-1 and IKK-2 are capable of forming homo- and heterodimers through their C-terminal leucine zipper motifs, with the heterodimeric form being preferred (Mercurio et. al., Mol. Cell Biol., 19:1526, 1999; Zandi et. al., Science; 281:1360, 1998; Lee et. al, Proc. Natl. Acad. Sci. USA 95:9319, 1998).

NIK, IKK-1 and IKK-2 are all serine/threonine kinases. Recent data has shown that tyrosine kinases also play a role in regulating the activation of NF-κB. A number of groups have shown that TNF-α induced NF-κB activation can be regulated by protein tyrosine phosphatases (PTPs) and tyrosine kinases (Amer et. al., JBC 273:29417–29423, 1998; Hu et. al., JBC 273:33561–33565, 1998; Kackawa et. al., Biochem. J. 337:179–184, 1999; Singh et. al., JBC 271 31049–31054, 1996). The mechanism of action of these enzymes appears to be in regulating the phosphorylation status of IκB. For example, PTP1B and an unidentified tyrosine kinase appear to directly control the phosphorylation of a lysine residue (K42) on IκB-α, which in turn has a critical influence on the accessibility of the adjacent serine residues as targets for phosphorylation by IKK.

Several groups have shown that IKK-1 and IKK-2 form part of a 'signalosome' structure in association with additional proteins including IKAP (Cohen et. al., Nature 395: 292–296, 1998; Rothwarf et. al., Nature 395:297–300, 1998), MEKK-1, putative MAP kinase phosphatase (Lee et. al., Proc. Natl. Acad. Sci. USA 95:9319–9324, 1998), as well as NIK and IκB. Data is now emerging to suggest that although both IKK-1 and IKK-2 associate with NIK, they are differentially activated, and therefore might represent an important integration point for the spectrum of signals that activate NF-κB. Importantly, MEKK-1 (one of the components of the putative signalosome and a target for UV light, LPS induced signalling molecules and small GTPases) has been found to activate IKK-2 but not IKK-1. Similarly, NIK phosphorylation of IKK-1 results in a dramatic increase in IKK-1 activity but only a small effect on IKK-2 (for review, see Mercurio, F., and Manning, A. M., Current Opinion in Cell Biology, 11:226–232, 1999).

Inhibition of NF-κB activation is likely to be of broad utility in the treatment of inflammatory disease.

There is accumulating evidence that NF-κB signalling plays a significant role in the development of cancer and metastasis. Abnormal expression of c-Rel, NF-κB2 or IκBα have been described in a number of tumour types and tumour cell lines, and there is now data to show that constitutive NF-κB signalling via IKK-2 takes place in a wide range of tumour cell lines. This activity has been linked to various upstream defects in growth factor signalling such as the establishment of autocrine loops, or the presence of oncogene products e.g. Ras, AKT, Her2, which are involved in the activation of the IKK complex. Constitutive NF-κB activity is believed to contribute to oncogenesis through activation of a range of anti-apoptotic genes e.g. A1/Bfi-1, IEX-1, XIAP, leading to the suppression of cell death pathways, and transcriptional upregulation of cyclin D1 which promotes cell growth. Other data indicate that this pathway is also likely to be involved in the regulation of cell adhesion and cell surface proteases. This suggests a possible additional role for NF-κB activity in the development of metastasis. Evidence confirming the involvement of NF-κB activity in oncogenesis includes the inhibition of tumour cell growth in vitro and in vivo on expression of a modified form of IκBα (super-repressor IκBα).

In addition to the constitutive NF-κB signalling observed in many tumour types, it has been reported that NF-κB is also activated in response to certain types of chemotherapy. Inhibition of NF-κB activation through expression of the super-repressor form of IκBα in parallel with chemotherapy treatment has been shown to enhance the antitumour effect of the chemotherapy in xenograft models. NF-κB activity is therefore also implicated in inducible chemoresistance.

DISCLOSURE OF THE INVENTION

According to the present invention, there is provided a compound of formula (I)

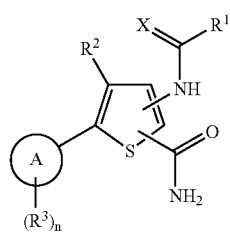

in which:

$R^1$ represents $NH_2$ or $R^1$ represents a methyl group optionally substituted by one or more groups selected independently from $C_1$–$C_4$ alkyl, $C_3$–$C_6$ cycloalkyl, halogen, hydroxyl, $C_1$–$C_4$ alkoxy, $S(O)_v CH_3$ and $NR^4 R^5$;

X represents O or S;

$R^2$ represents hydrogen, halogen, cyano, nitro, —$NR^6 R^7$, —$CONR^6 R^7$, —$COOR^6$, —$NR^6 COR^7$, —$S(O)_m R^6$, —$SO_2 NR^6 R^7$, —$NR^6 SO_2 R^7$, $C_1$–$C_2$ alkyl, trifluoromethyl, $C_2$–$C_3$ alkenyl, $C_2$–$C_3$ alkynyl, trifluoromethoxy, $C_1$–$C_2$ alkoxy or $C_1$–$C_2$ alkanoyl;

A represents a phenyl ring or a 5- to 7-membered heteroaromatic ring containing one to three heteroatoms selected independently from O, N and S; said phenyl or heteroaromatic ring being optionally substituted by one or more substituents selected independently from halogen, cyano, nitro, —$NR^8 R^9$, —$CONR^8 R^9$, —$COOR^9$, —$NR^8 COR^9$, —$S(O)_s R^8$, —$SO_2 NR^8 R^9$, —$NR^8 SO_2 R^9$, $C_1$–$C_6$ alkyl, trifluoromethyl, —$(CH_2)_t R^{10}$, —$O(CH_2)_t R^{11}$ or —$OR^{12}$;

n represents an integer 1 or 2; and when n represents 2, each $R^3$ group may be selected independently;

$R^3$ represents a group —W—Y—Z wherein:

W represents O, $S(O)_r$, $NR^{13}$, $CH_2$, —$CH_2$—O— or a bond;

Y represents a bond or a group —$(CH_2)_p$—T—$(CH_2)_q$— wherein p and q independently represent an integer 0, 1 or 2; and T represents O, —CO— or $CR^{14}R^{15}$;

$R^{14}$ and $R^{15}$ independently represent H, $CH_3$ or F;

or $R^{14}$ represents H or $CH_3$ and $R^{15}$ represents hydroxyl or $OCH_3$;

or the group $CR^{14}R^{15}$ together represents a $C_3$–$C_6$ cycloalkyl ring;

Z represents:

(a) a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, —$NR^{16}R^{17}$, —$CONR^{16}R^{17}$, —$COOR^{16}$, —$COR^{16}$—$NR^{16}COR^{17}$, —$S(O)_u R^{16}$, —$SO_2 NR^{16}R^{17}$, —$NR^{16} SO_2 R^{17}$, hydroxyl, $C_2$–$C_6$ alkenyl, $C_2$–$C_6$ alkynyl, $C_1$–$C_6$ alkyl and $C_1$–$C_6$ alkoxy; said alkyl or alkoxy group being optionally further substituted by one or more groups selected from halogen, cyano, hydroxyl, $C_1$–$C_4$ alkoxy and $NR^{18}R^{19}$; or (b) a 3- to 8-membered saturated or partially unsaturated monocyclic or saturated bicyclic ring system optionally incorporating one or two heteroatoms selected independently from O, N and S, and optionally incorporating a carbonyl group; said ring system being optionally substituted by one or more substituents selected independently from halogen, cyano, —$NR^{16}R^{17}$, $CONR^{16}R^{17}$, —$COOR^{16}$, —$COR^{16}$, —$NR^{16}COR^{17}$, —$S(O)_u R^{16}$, —$SO_2 NR^{16}R^{17}$, —$NR^{16}SO_2 R^{17}$, hydroxyl, $C_2$–$C_6$ alkenyl, $C_2$–$C_6$ alkynyl, $C_1$–$C_6$ alkyl, $C_3$–$C_6$ cycloalkyl and $C_1$–$C_6$ alkoxy; said alkyl or alkoxy group being optionally further substituted by one or more groups selected from halogen, cyano, hydroxyl, $C_3$–$C_6$ cycloalkyl, $C_1$–$C_4$ alkoxy and $NR^{18}R^{19}$; provided that said saturated monocyclic ring Z is not bonded to Y through nitrogen if the group —W—Y— represents —$(CH_2)_{2-4}$— or —O—$(CH_2)_{2-4}$— when the saturated ring Z is also unsubstituted; or (c) if W represents O, then Z may also represent hydroxyl, $OCH_3$, $CF_3$, $CHF_2$ or $CH_2 F$, provided that the group —Y—Z does not thereby represent $(CH_2)_{2-4}$—$OCH_3$;

$R^{10}$ and $R^{11}$ independently represent $NR^{20}R^{21}$ where $R^{20}$ and $R^{21}$ are independently hydrogen or $C_1$–$C_6$ alkyl optionally substituted by $C_1$–$C_4$ alkoxy; or the group $NR^{20}R^{21}$ represents a 5- or 6-membered saturated azacyclic ring optionally containing a further O, S or $NR^{22}$ group; where $R^{22}$ is hydrogen or $C_1$–$C_6$ alkyl; or $R^{10}$ and $R^{11}$ independently represent $C_1$–$C_6$ alkoxy;

$R^4$ and $R^5$ independently represent H or $C_1$–$C_4$ alkyl; or the group $NR^4 R^5$ represents a 5- or 6-membered saturated azacyclic ring optionally containing a further O, S or $NR^{23}$ group; where $R^{23}$ is hydrogen or $C_1$–$C_4$ alkyl;

$R^6$ and $R^7$ independently represent H or $C_1$–$C_2$ alkyl;

$R^8$, $R^9$ and $R^{12}$ independently represent H or $C_1$–$C_6$ alkyl;

$R^{13}$ represents H or $C_1$–$C_4$ alkyl;

$R^{16}$ and $R^{17}$ independently represent H or $C_1$–$C_6$ alkyl optionally substituted by OH, $C_1$–$C_4$ alkoxy or one or more fluoro atoms; or the group $NR^{16}R^{17}$ represents a 5- or 6-membered saturated azacyclic ring optionally containing a further O, S or $NR^{24}$ group; where $R^{24}$ is hydrogen or $C_1$–$C_6$ alkyl optionally substituted by OH, $C_1$–$C_4$ alkoxy or one or more fluoro atoms;

$R^{18}$ and $R^{19}$ independently represent H or $C_1$–$C_4$ alkyl; or the group $NR^{18}R^{19}$ represents a 5- or 6-membered saturated azacyclic ring optionally containing a farther O, S or $NR^{25}$ group; where $R^{25}$ is hydrogen or $C_1$–$C_4$ alkyl;

m, r, s, u and v independently represent an integer 0, 1 or 2;

t represents an integer 2, 3 or 4;

and pharmaceutically acceptable salts thereof:

with the proviso that the following two compounds are excluded:

2-[(aminocarbonyl)amino]-5-(4-[2-(1-(2,2,6,6-tetramethyl)piperidinyl)ethoxy]phenyl)-3-thiophenecarboxamide;

2-[(aminocarbonyl)amino]-5-(4-(thiazol4-yl-methoxy)phenyl)-3-thiophenecarboxamide.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In one embodiment, the invention provides compounds of formula (I) wherein Z represents:

(a) a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, $-NR^{16}R^{17}$, $-CONR^{16}R^{17}$, $-COOR^{16}$, $-COR^{16}-NR^{16}COR^{17}$, $-S(O)_uR^{16}$, $-SO_2NR^{16}R^{17}$, $-NR^{16}SO_2R^{17}$, hydroxyl, $C_2-C_6$ alkenyl, $C_2-C_6$ alkynyl, $C_1-C_6$ alkyl and $C_1-C_6$ alkoxy; said alkyl or alkoxy group being optionally further substituted by one or more groups selected from halogen, cyano, hydroxyl, $C_1-C_4$ alkoxy and $NR^{18}R^{19}$; or (b) a saturated 3- to 7-membered ring optionally incorporating one or two heteroatoms selected independently from O, N and S, and optionally incorporating a carbonyl group; said saturated ring being optionally substituted by one or more substituents selected independently from halogen, cyano, $-NR^{16}R^{17}$, $-CONR^{16}R^{17}$, $-COOR^{16}$, $-COR^{16}$, $-NR^{16}COR^{17}$, $-S(O)_uR^{16}$, $-SO_2NR^{16}R^{17}$, $-NR^{16}SO_2R^{17}$, hydroxyl, $C_2-C_6$ alkenyl, $C_2-C_6$ alkynyl, $C_1-C_6$ alkyl and $C_1-C_6$ alkoxy; said alkyl or alkoxy group being optionally further substituted by one or more groups selected from halogen, cyano, hydroxyl, $C_1-C_4$ alkoxy and $NR^{18}R^{19}$; provided that said saturated ring Z is not bonded to Y through nitrogen if the group $-W-Y-$ represents $-(CH_2)_{2-4}-$ or $-O-(CH_2)_{2-4}-$ when the saturated ring Z is also unsubstituted; or (c) if W represents O, then Z may also represent hydroxyl, $OCH_3$, $CF_3$, $CHF_2$ or $CH_2F$, provided that the group $-Y-Z$ does not thereby represent $-O-(CH_2)_{2-4}-OCH_3$; and all other substituents are as defined above.

In one embodiment, X in formula (I) represents oxygen.

In another embodiment, $R^1$ in formula (I) represents $NH_2$.

Suitably the group A in formula (I) is a phenyl group or a 5- to 7-membered heteroaromatic ring containing one to three heteroatoms selected independently from O, N and S; said phenyl or heteroaromatic ring being optionally substituted by one or more substituents selected independently from halogen, cyano, nitro, $-NR^8R^9$, $-CONR^8R^9$, $-COOR^8$, $-NR^8COR^9$, $-S(O)_sR^8$, $-SO_2NR^8R^9$, $-NR^8SO_2R^9$, $C_1-C_6$ alkyl, trifluoromethyl, $-(CH_2)_rR^{10}$, $-O(CH_2)_rR^{11}$ or $-OR^{12}$. In one embodiment, A represents optionally substituted phenyl. In another embodiment, A represents an optionally substituted pyridyl.

In one embodiment, the group $R^2$ in formula (I) represents H, halogen or $C_1-C_2$ alkyl. In another embodiment, the group $R^2$ represents H or methyl. In another embodiment, the group $R^2$ in formula (I) represents H.

In another embodiment, W in formula (I) represents O, $CH_2$ or a bond.

In another embodiment, Y in formula (I) represents $-CH_2-CH_2-$ or a bond.

In another embodiment, Z in formula (I) represents a 3- to 8-membered saturated or partially unsaturated monocyclic or saturated bicyclic ring system optionally incorporating one or two heteroatoms selected independently from O, N and S, and optionally incorporating a carbonyl group; said ring system being optionally substituted by one or more substituents selected independently from halogen, cyano, $-NR^{16}R^{17}$, $-CONR^{16}R^{17}$, $-COOR^{16}$, $-COR^{16}$, $-NR^{16}COR^{17}$, $-S(O)_uR^{16}$, $-SO_2NR^{16}R^{17}$, $-NR^{16}SO_2R^{17}$, hydroxyl, $C_2-C_6$ alkenyl, $C_2-C_6$ alkynyl, $C_1-C_6$ alkyl, $C_3-C_6$ cycloalkyl and $C_1-C_6$ alkoxy; said alkyl or alkoxy group being optionally further substituted by one or more groups selected from halogen, cyano, hydroxyl, $C_3-C_6$ cycloalkyl, $C_1-C_4$ alkoxy and $NR^{18}R^{19}$; provided that said saturated monocyclic ring Z is not bonded to Y through nitrogen if the group $-W-Y-$ represents $-(CH_2)_{2-4}-$ or $-O-(CH_2)_{2-4}-$ when the saturated ring Z is also unsubstituted.

In another embodiment, Z in formula (I) represents a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, $-NR^{16}R^{17}$, $-CONR^{16}R^{17}$, $-COOR^{16}$, $-COR^{16}-NR^{16}COR^{17}$, $-S(O)_uR^{16}$, $-SO_2NR^{16}R^{17}$, $-NR^{16}R^{17}$, $-NR^{16}SO_2R^{17}$, hydroxyl, $C_2-C_6$ alkenyl, $C_2-C_6$ alkynyl, $C_1-C_6$ alkyl and $C_1-C_6$ alkoxy; said alkyl or alkoxy group being optionally further substituted by one or more groups selected from halogen, cyano, hydroxyl, $C_1-C_4$ alkoxy and $NR^{18}R^{19}$.

In one embodiment, n has the value 1.

The compounds of formula (I) and their pharmaceutically acceptable salts have the advantage that they are inhibitors of the enzyme IKK-2.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of IKK-2 activity is beneficial.

A more particular aspect of the invention provides the use of a compound of formula (I) or a pharmaceutically acceptable salt thereof, in the manufacture of a medicament, for the treatment or prophylaxis of inflammatory disease.

According to the invention, there is also provided a method of treating, or reducing the risk of, diseases or conditions in which inhibition of IKK-2 activity is beneficial which comprises administering to a person suffering from or at risk of, said disease or condition, a therapeutically effective amount of a compound of formula (I), or a pharmaceutically acceptable salt mate thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

Particular compounds of the invention include those exemplified herein:

2-[(aminocarbonyl)amino]-4-methyl-5-(4-biphenyl)-3-thiophenecarboxamide;

2-[(aminocarbonyl)amino]-4-methyl-5-(4-[(3,5-dimethoxylisoxazol-4-yl)methoxy]phenyl)-3-thiophenecarboxamide;

2-[(aminocarbonyl)amino]-4-methyl-5-(4-[(4-chlorophenyl)methoxy]phenyl)-3-thiophenecarboxamide;

2-[(aminocarbonyl)amino]-4-methyl-5-(4-[(5-chlorothien-2-yl)methoxy]phenyl)-3-thiophenecarboxamide;

2-[(aminocarbonyl)amino]-4-methyl-5-{4-[2-(2,2,6,6-tetramethylpiperidine-1-yl)ethoxy]phenyl}-3-thiophenecarboxamide;

2-[(aminocarbonyl)amino]-4-methyl-5-(4-[(thiazol-4-yl)methoxy]phenyl)-3-thiophenecarboxamide;

2-[(aminocarbonyl)amino]-4-methyl-5-(4-[(1,2,5-thiadiazol-3-yl)methoxy]phenyl)-3-thiophenecarboxamide;

2-[(aminocarbonyl)amino]-4-methyl-5-(4-[(1-methylperhydroazepin-3-yl)oxy]phenyl)-3-thiophenecarboxamide;

2-[(aminocarbonyl)amino]-5-[6-(pyrrolidin-1-yl)pyridin-3-yl]-3-thiophenecarboxamide;

2-[(aminocarbonyl)amino]-5-[6-(2,2-difluoroethoxy)pyridin-3-yl]-3-thiophenecarboxamide;

2-[(aminocarbonyl)amino]-5-[6-(piperidin-1-yl)pyridin-3-yl]-3-thiophenecarboxamide;

2-[(aminocarbonyl)amino]-5-[6-(cyclopentyloxy)pyridin-3-yl]-3-thiophenecarboxamide;

2-[(aminocarbonyl)amino]-5-[6-(4-ethanesulfonylpiperazin-1-yl)pyridin-3-yl]-3-thiophenecarboxamide;

2-[(aminocarbonyl)amino]-5-[6-[(tetrahydrofuran-2-yl)methoxy]pyridin-3-yl]-3-thiophenecarboxamide;

2-[(aminocarbonyl)amino]-5-{3-[6-(furan-2-ylmethoxy)]-pyridine}-3-thiophenecarboxamide;

2-[(aminocarbonyl)amino]-5-{3-[6-(4-acetyl)piperazin-1-yl]-pyridine}-3-thiophenecarboxamide;

(R)-2-[(aminocarbonyl)amino]-5-{3-[6-(tetrahydrofuran-3-yloxy)]-pyridine}-3-thiophenecarboxamide;

2-[(aminocarbonyl) amino]-5-{3-[6-(1-isopropyl-pyrrolidin-3-yloxy)]-pyridine}-3-thiophenecarboxamide;

2-[(aminocarbonyl)amino]-5-{3-[6-(1-t-butyloxycarbonyl-piperidin-4-yloxy)]-pyridine}-3-thiophenecarboxamide;

2-[(aminocarbonyl)amino]-5-{3-[6-(piperidin-4-yloxy)]-pyridine}-3-thiophenecarboxamide;

2-[(aminocarbonyl)amino]-5-{3-[6-(1-(2-methoxyethyl)-piperidin-4-yloxy)]-pyridine}-3-thiophenecarboxamide;

2[(aminocarbonyl)amino]-5-{3-[6-(N-methanesulphonyl)-piperidin-4-yloxy]-pyridine}-3-thiophenecarboxamide;

2-[(aminocarbonyl)amino]-5-{3-[6-(4,4-difluoropiperidin-1-yl)pyridine}-3-thiophenecarboxamide;

2-[(aminocarbonyl)amino]-5-{3-[6-(pyrrolidin-1-yl)-5-methyl]pyridine}-3-thiophenecarboxamide;

2-[(aminocarbonyl)amino]-5-{3-[6-(thien-2-ylmethoxy)]pyridine}-3-thiophenecarboxamide;

2-[(aminocarbonyl)amino]-5-{3-[6-(cyclopentylmethoxy)]pyridine}-3-thiophenecarboxamide;

2-[(aminocarbonyl)amino]-5-[3-(6-benzyloxy)pyridine]-3-thiophenecarboxamide;

2-[(aminocarbonyl)amino]-5-{3-[6-(tetrahydrofuran-3-yloxy)]pyridine}-3-thiophenecarboxamide;

2-[(aminocarbonyl)amino]-5-{3-[6-(tetrahydrofuran-3-ylmethoxy)]pyridine}-3-thiophenecarboxamide;

2-[(aminocarbonyl)amino]-5-{3-[6-(cyclopropylmethoxy)]pyridine}-3-thiophenecarboxamide;

(S)-2-[(aminocarbonyl)amino]-5-{3-[6-(tetrahydrofuran-3-yloxy)]pyridine}-3 thiophenecarboxamide;

2-[(aminocarbonyl)amino]-5-{3-[6-(tetrahydropyran-4-yloxy)]pyridine}-3-thiophenecarboxamide;

2-[(aminocarbonyl)amino]-5-{3-[6-(tetrahydrothiopyran-3-yloxy)]pyridine}-3-thiophenecarboxamide;

2-[(aminocarbonyl)amino]-5-{3-[6-(1-isopropylazetidin-3-yloxy)]pyridine}-3-thiophenecarboxamide;

2-[(aminocarbonyl)amino]-5-{3-[6-(benzyloxy-2-ethoxy)]pyridine}-3-thiophenecarboxamide;

2-[(aminocarbonyl)amino]-5-{3-[6-(N-methylpiperidin-3-yloxy)]pyridine}-3-thiophenecarboxamide;

2-[(aminocarbonyl)amino]-5-{3-[6-(2-(1-pyrrolidin-2-one)ethoxy)]pyridine}-3-thiophenecarboxamide;

2-[(aminocarbonyl)amino]-5-[3-(6-(morpholin-4-yl))pyridine]-3-thiophenecarboxamide;

2-[(aminocarbonyl)amino]-5-{3-[6-(4-methylpiperazin-1-yl)]pyridine}-3-thiophenecarboxamide;

2-[(aminocarbonyl)amino]-5-(4-[1,3,4-oxadiazol-2-yl]-2-phenyl)-3-thiophenecarboxamide;

2-[(aminocarbonyl)amino]-5-(4-cyclopropylmethoxyphenyl)-3-thiophenecarboxamide;

2-[(aminocarbonyl)amino]-5-[3-(1,3-thiazol-4-ylmethoxy)phenyl]thiophene-3-carboxamide;

2-[(aminocarbonyl)amino]-5-[4-(morpholin-4-ylmethyl)phenyl]thiophene-3-carboxamide;

2-[(aminocarbonyl)amino]-5-(5-[2-(N-morpholinyl)]pyrimidinyl)-3-thiophenecarboxamide;

2-[(aminocarbonyl)amino]-5-(5-[2-(N-piperidinyl)]pyrimidinyl)-3-thiophenecarboxamide;

2-[(aminocarbonyl)amino]-5-(5-[2-(N-pyrrolidinyl)]pyrimidinyl)-3-thiophenecarboxamide;

2-[(aminocarbonyl)amino]-5-(5-[2-{4-(t-butyloxycarbonyl)piperazin-1-yl}]pyrimidinyl)-3-thiophenecarboxamide;

2-[(aminocarbonyl)amino]-5-(-5-[2-{4H-piperazin-1-yl}]pyrimidinyl)-3-thiophenecarboxamide;

2-[(aminocarbonyl)amino]-5-(5-[2-{4-methylpiperazin-1-yl}]pyrimidinyl)-3-thiophenecarboxamide;

2-[(aminocarbonyl)amino]-5-(5-[2-(3-dimethylaminopyrrolidin-1-yl)]pyrimidinyl)-3-thiophenecarboxamide;

2-[(aminocarbonyl)amino]-5-(5-[2-{2(S)-aminocarbonylpyrrolidin-1-yl}]pyrimidinyl)-3-thiophenecarboxamide;

2-[(aminocarbonyl)amino]-5-(5-[2-{4-acetylpiperazin-1-yl}]pyrimidinyl)-3-thiophenecarboxamide;

2-[(aminocarbonyl)amino]-5-(5-{2-[4,4-difluoropiperidin-1-yl]}pyrimidinyl)-3-thiophenecarboxamide;

2-[(aminocarbonyl)amino]-5-(5-{2-[3,3-difluoropyrrolidin-1-yl]}pyrimidinyl)-3-thiophenecarboxamide;

2-[(aminocarbonyl)amino]-5-{2-(5-N-morpholinomethyl)thienyl}-3-thiophenecarboxamide;

2-[(aminocarbonyl)amino]-5-{2-benzyloxyphenyl}-3-thiophenecarboxamide;

2-[(aminocarbonyl)amino]-5-{2-(4-fluorophenylmethoxy)phenyl}-3-thiophenecarboxamide;

2-[(aminocarbonyl)amino]-5-{2-(2-[4-fluorophenyl]ethoxy)phenyl}-3-thiophenecarboxamide;

2-[(aminocarbonyl)amino]-5-{2-(2-[4-chlorophenyl]ethoxy)phenyl}-3-thiophenecarboxamide;

2-[(aminocarbonyl)amino]-5-{2-(2-phenylethoxy)phenyl}-3-thiophenecarboxamide;

2-[(aminocarbonyl)amino]-5-{4-chlorophenylmethoxy)phenyl}-3-thiophenecarboxamide;

2-[(aminocarbonyl)amino]-5-{2-[2-(N-morpholinyl)]ethylthio)phenyl}-3-thiophenecarboxamide;

2-[(aminocarbonyl)amino]-5-{2-[2-(N-pyrrolidinyl)]ethylthio)phenyl}-3-thiophenecarboxamide;

2-[(aminocarbonyl)amino]-5-{2-[2-(N-piperidinyl)]ethylthio)phenyl}-3-thiophenecarboxamide;

2-[(aminocarbonyl)amino]-5-[4-(pyrrolidinyl)phenyl]-3-thiophenecarboxamide;

2-[(aminocarbonyl)amino]-5-[4-(piperidinyl)phenyl]-3-thiophenecarboxamide;

2-[(aminocarbonyl)amino]-5-[4-(N-imidazolyl)phenyl]-3-thiophenecarboxamide;

2-[(aminocarbonyl)amino]-5-[6-{(1-methylpyrrolidin-2-on-4-yl)methoxy}pyridin-3-yl]-3-thiophenecarboxamide;

2-[(aminocarbonyl)amino]-5 {4-[2-(2-methoxyethoxy)ethoxy]-phenyl}-3-thiophenecarboxamide;

2-[(aminocarbonyl)amino]-5-{4-[2-(cyclopropylmethoxy)ethoxy]phenyl}-3-thiophenecarboxamide;

2-[(aminocarbonyl)amino]-5-(6-(2,2-dimethyl-3-pyrrolidinylpropoxy)pyridin-3-yl]-3-thiophenecarboxamide;

2-[(aminocarbonyl)amino]-5-{3-chloro-4-(tetrahydrofuran-2-ylmethoxy)phenyl}-3-thiophenecarboxamide;

2-[(aminocarbonyl)amino]-5-{4-(tetrahydrofuran-2-ylmethoxy)phenyl}-3-thiophenecarboxamide;

2-[(aminocarbonyl)amino]-5-[(6-cyclopropylmethylthio)pyridin-3-yl]-3-thiophenecarboxamide;

2-[(aminocarbonyl)amino]-5 {4-[2-(2-methoxyethoxy)ethoxy]-3-methylphenyl}-3-thiophenecarboxamide;

2-[(aminocarbonyl)amino]-5-{3-chloro-4-[2-(2-methoxyethoxy)ethoxy]phenyl}-3-thiophenecarboxamide;

2-[(aminocarbonyl)amino]-5-[2-(4-methylpiperazinylmethyl)phenyl-3-thiophenecarboxamide;

2-[(aminocarbonyl)amino]-5-[2-(4-isopropylpiperazinylmethyl)phenyl]-3-thiophenecarboxamide;

2-[(aminocarbonyl)amino]-5-[2-(4-t-butyloxycarbonylpiperazinylmethyl)phenyl]-3-thiophenecarboxamide;

2-[(aminocarbonyl)amino]-5-[4-(pyrrolidinylmethyl)phenyl]thiophene-3-carboxamide;

2-[(aminocarbonyl)amino]-5-[2-(2-(4,4-difluoropiperidin-1-yl)ethoxy)phenyl]-3-thiophenecarboxamide;

2-[(aminocarbonyl)amino]-5-[2-(2-(3,3-difluoropyrrolidin-1-yl)ethoxy)phenyl]-3-thiophenecarboxamide;

3-[(aminocarbonyl)amino]-5-[4-(morpholin-4-ylmethyl)phenyl]thiophene-2-carboxamide;

3-[(aminocarbonyl)amino]-5-[4-(cis-2,6-dimethylmorpholin-4-ylmethyl)phenyl]thiophene-2-carboxamide;

2-[(aminocarbonyl)amino]-5-[4-(cis-2,6-dimethylmorpholin-4-ylmethyl)phenyl]thiophene-3-carboxamide;

2-[(aminocarbonyl)amino]-5-[(6-{4-morpholino}methyl)pyridin-3-yl]thiophene-3-carboxamide;

2-[(aminocarbonyl)amino]-5-[4-(8-oxa-3-azabicyclo[3.2.1]oct-3-ylmethyl)phenyl]thiophene-3-carboxamide;

2-[(aminocarbonyl)amino]-5-[3-(morpholin-4-ylmethyl)-4-isobutoxyphenyl]thiophene-3-carboxamide;

2-[(aminocarbonyl)amino]-5-[3-(morpholin-4-ylmethyl)phenyl]thiophene-3-carboxamide;

2-[(aminocarbonyl)amino]-5-(4-{[2-(methoxymethyl)morpholin-4-yl]methyl}phenyl)thiophene-3-carboxamide;

2-[(aminocarbonyl)amino]-5-[3-fluoro-4-(morpholin-4-ylmethyl)phenyl]thiophene-3-carboxamide;

2-[(aminocarbonyl)amino]-5-[3-chloro-4-(morpholin-4-ylmethyl)phenyl]thiophene-3-carboxamide;

2-[(aminocarbonyl)amino]-5-{4-[(4,4-difluoropiperidin-1-yl)methyl]phenyl}thiophene-3-carboxamide;

2-[(aminocarbonyl)amino]-5-[4-(1-{piperidin-1-yl}ethyl)phenyl]thiophene-3-carboxamide;

2-[(aminocarbonyl)amino]-5-{4-[(1R)-1-morpholin-4-ylethyl]phenyl}thiophene-3-carboxamide;

2-[(aminocarbonyl)amino]-5-(4-{[4-(2-methoxyethyl)piperazin-1-yl]methyl}phenyl)thiophene-3-carboxamide;

2-[(aminocarbonyl)amino]-5-[4-(piperidin-1-ylmethyl)phenyl]thiophene-3-carboxamide;

2-[(aminocarbonyl)amino]-5-{4-[(1S,4S)-2-oxa-5-azabicyclo[2.2.1]hept-5-ylmethyl]phenyl}thiophene-3-carboxamide;

5-{4-[(4-acetylpiperazin-1-yl)methyl]phenyl}-2-[(aminocarbonyl)amino]thiophene-3-carboxamide;

2-[(aminocarbonyl)amino]-5-(4-(1,4-oxazepan-ylmethyl)phenyl]thiophene-3-carboxamide;

(1S)-2-[(aminocarbonyl)amino)-5-(4-(1-{morpholin-4-yl}ethyl)phenyl)thiophene-3-carboxamide;

2-((aminocarbonyl)amino)-5-(4-(1-methyl-1-{morpholin-4-yl}ethyl)phenyl)thiophene-3-carboxamide;

2-[(aminocarbonyl)amino]-5-[4-((4-methylpiperazin-1-yl)methyl)phenyl]thiophene-3-carboxamide;

2-[(aminocarbonyl)amino]-5-[4-((2-ethoxycarbonylpiperidin-1-yl)methyl)phenyl]thiophene-3-carboxamide;

2-[(aminocarbonyl)amino]-5-[4-((3-diethylaminocarbonylpiperidin-1-yl)methyl)phenyl]-thiophene-3-carboxamide;

2-[(aminocarbonyl)amino]-5-[4-((3-hydroxypyrolidin-1-yl)methyl)phenyl]thiophene-3-carboxamide;

2-[(aminocarbonyl)amino]-5-[4-({(2-hydroxyethyl)piperazin-1-yl}methyl)phenyl]thiophene-3-carboxamide;

2-[(aminocarbonyl)amino]-4-methyl-5-{4-[4-morpholino]methylphenyl}-3-thiophenecarboxamide;

2-[(aminocarbonyl)amino]-5-[4-((4-hydroxypiperidine-1-yl)methyl)phenyl]thiophene-3-carboxamide 2-[(aminocarbonyl)amino]-5-(2-piperazin-1-ylphenyl)thiophene-3-carboxamide;

2-[(aminocarbonyl)amino]-5-[2-(4-methylpiperazin-1-yl)phenyl]thiophene-3-carboxamide;

2-[(aminocarbonyl)amino]-5-{2-[3-methylamino)pyrrolidin-1-yl]phenyl}thiophene-3-carboxamide;

2-[(aminocarbonyl)amino]-5-[4-(cyclopentyloxy)-2-(2-{piperidin-1-yl}ethoxy)phenyl]thiophene-3-carboxamide;

2-[(aminocarbonyl)amino]-5-[2-(2-{piperidin-1-yl}ethoxy)-4-pyrrolidin-1-ylphenyl]thiophene-3-carboxamide;

2-[(aminocarbonyl)amino]-5-[4-piperidin-1-yl-2-(2-{piperidin-1-yl}ethoxy)phenyl]thiophene-3-carboxamide;

2-[(aminocarbonyl)amino]-5-[4-(morpholin-4-ylmethyl)-2-(2-{piperidin-1-yl}ethoxy)phenyl]thiophene-3-carboxamide;

2-[(aminocarbonyl)amino]-5-[4-(2-methoxyethoxy)-2-(2-piperidin-1-ylethoxy)phenyl]thiophene-3-carboxamide;

2-[(aminocarbonyl)amino]-5-[4-morpholin-4-yl-2-(2-piperidin-1-ylethoxy)phenyl]thiophene-3-carboxamide;

2-[(aminocarbonyl)amino]-5-[2-(2-hydroxyethoxy)phenyl]thiophene-3-carboxamide;

(3R)-2-[(aminocarbonyl)amino]-5-{2-[tetrahydrofuran-3-yloxy]phenyl}-3-thiophenecarboxamide;

(3S)-2-[(aminocarbonyl)amino]-5-{2-[tetrahydrofuran-3-yloxy]phenyl}-3-thiophenecarboxamide;

2-[(aminocarbonyl)amino]-5-{2-[(tetrahydropyran-4-yloxy]phenyl}-3-thiophenecarboxamide;

2-[(aminocarbonyl)amino]-5-{2-[cyclopropylmethoxy]phenyl}-3-thiophenecarboxamide;

2-[(aminocarbonyl)amino]-5-{2-[cyclopentyloxy]phenyl}-3-thiophenecarboxamide;

2-[(aminocarbonyl)amino]-5-{2-[(1-isopropylpyrrolidin-3-yl)oxy]phenyl}-3-thiophenecarboxamide;

2-[(aminocarbonyl)amino]-5-{2-[(1-ethylpyrrolidin-3-yl)oxy]phenyl}-3-thiophenecarboxamide;

2-[(aminocarbonyl)amino]-5-{2-[(1-tert-butyloxycarbonyl-3-pyrrolidinyl)oxy]phenyl}-3-thiophenecarboxamide;

2-[(aminocarbonyl)amino]-5-[2-(pyrrolidin-3-yloxy)phenyl]-3-thiophenecarboxamide;

2-[(aminocarbonyl)amino]-5-{2-[(1-methylpiperidin-2-yl)methoxy]phenyl}-3-thiophenecarboxamide;

(2S)-2-[(aminocarbonyl)amino]-5-(2-{[1-methylpyrrolidin-2-yl]methoxy}phenyl)-3-thiophenecarboxamide;

2-[(aminocarbonyl)amino]-5-(2-{[1-(2-methoxyethyl)pyrrolidin-3-yl]oxy}phenyl)-3-thiophenecarboxamide;

(2R)-2-[(aminocarbonyl)amino]-5-(2-{[1-methylpyrrolidin-2-yl]methoxy}phenyl)-3-thiophenecarboxamide;

2-[(aminocarbonyl)amino]-5-[2-(2-(2,2,6-trimethylpiperidin-1-yl)ethoxy)phenyl]-3-thiophenecarboxamide;

2-[(aminocarbonyl)amino]-5-{5-chloro-2-[(1-isopropylpyrrolidin-3-yl)oxy]phenyl}-3-thiophenecarboxamide;

2-[(aminocarbonyl)amino]-5-{4-fluoro-2-[(1-isopropylpyrrolidin-3-yl)oxy]phenyl}-3-thiophenecarboxamide;

2-[(aminocarbonyl)amino]-5-{4,5-difluoro-2-[(1-isopropylpyrrolidin-3-yl)oxy]phenyl}-3-thiophenecarboxamide;

2-[(aminocarbonyl)amino]-5-{2-[(1-isopropylpyrrolidin-3-yl)oxy]-5-methylphenyl}-3-thiophenecarboxamide;

2-[(aminocarbonyl)amino]-5-{5-cyano-2-[(1-isopropylpyrrolidin-3-yl)oxy]phenyl}-3-thiophenecarboxamide;

2-[(aminocarbonyl)amino]-5-{2-[(1-isopropylpyrrolidin-3-yl)oxy]-5-methoxyphenyl}-3-thiophenecarboxamide;

2-[(aminocarbonyl)amino]-5-{3,5-difluoro-2-[(1-isopropylpyrrolidin-3-yl)oxy]phenyl}-3-thiophenecarboxamide;

2-[(aminocarbonyl)amino]-5-{2-[(1-isopropylpyrrolidin-3-yl)oxy]-3-methoxyphenyl}-3-thiophenecarboxamide;

2-[(aminocarbonyl)amino]-5-{2-[(1-isopropylpyrrolidin-3-yl)oxy]-5-trifluoromethylphenyl}-3-thiophenecarboxamide;

2-[(aminocarbonyl)amino]-5-{2-[(1-isopropylpyrrolidin-3-yl)oxy]-4-trifluoromethylphenyl}-3-thiophenecarboxamide;

2-[(aminocarbonyl)amino]-5-{2-[(1-isopropylpyrrolidin-3-yl)oxy]-4-methoxyphenyl}-3-thiophenecarboxamide;

2-[(aminocarbonyl)amino]-5-{5-fluoro-2-[(1-isopropylpyrrolidin-3-yl)oxy]phenyl}-3-thiophenecarboxamide;

2-[(aminocarbonyl)amino]-5-{2-[(1-isopropylpyrrolidin-3-yl)oxy]-3-(morpholin-4-ylmethyl)phenyl}-3-thiophenecarboxamide;

2-[(aminocarbonyl)amino]-5-(2-{[1-(cyclopropylmethyl)pyrrolidin-3-yl]oxy}phenyl)-3-thiophenecarboxamide;

2-[(aminocarbonyl)amino]-5-{2-[1-cyclopropylpyrrolidin-3-yl)oxy]phenyl}-3-thiophenecarboxamide;

2-[(aminocarbonyl)amino]-5-{2-[(2-(4-fluoropiperidin-1-yl)ethoxy]phenyl}-3-thiophenecarboxamide;

2-[(aminocarbonyl)amino]-5-{2-[(1-methylpiperidin-4-yl)oxy]phenyl}-3-thiophenecarboxamide;

2-[(aminocarbonyl)amino]-5-{2-[(1-methylpyrrolidin-3-yl)oxy]phenyl}-3-thiophenecarboxamide;

2-[(aminocarbonyl)amino]-5-[4-(2-{morpholin-4-yl}acetyl)phenyl]3-thiophenecarboxamide;

2-[(aminocarbonyl)amino]-5-[2-{2-(4-hydroxy-1-piperidinyl)ethoxy}phenyl]-3-thiophenecarboxamide;

2-[(aminocarbonyl)amino]-5-[2-(2-(2,2,6,6-tetramethylpiperidin-1-yl)ethoxy)phenyl]-3-thiophenecarboxamide;

2-[(aminocarbonyl)amino]-5-{2-[2-(3-pyrrolin-1-yl)ethoxy]phenyl}thiophene-3-carboxamide;

cis/trans-2-[(aminocarbonyl)amino]-5-{2-[2-(2,5-dimethyl-3-pyrrolin-1-yl)ethoxy]phenylthiophene-3-carboxamide;

(2S)-2-[(aminocarbonyl)amino]-5-[4-(2-methoxymethylpyrrolidin-1-ylmethyl)phenyl]thiophene-3-carboxamide;

2-[(aminocarbonyl)amino]-5-[4-(4-aminocarbonylpiperidin-1-ylmethyl)phenylthiophene-3-carboxamide;

2-[(aminocarbonyl)amino]-5-[4-(3-hydroxymethylpiperidin-1-ylmethyl)phenyl]thiophene-3-carboxamide;

2-[(aminocarbonyl)amino]-5-[4-(4-hydroxymethylpiperidin-1-ylmethyl)phenyl]thiophene-3-carboxamide;

2-[(aminocarbonyl)amino]-5-[2-(3-{morpholin-4-yl}pyrrolidin-1-yl)phenyl]thiophene-3-carboxamide;

2-[(aminocarbonyl)amino]-5-{2-[4-(2-methoxyethyl)piperazin-1-yl]phenyl}thiophene-3-carboxamide;

2-[(aminocarbonyl)amino]-5-{2-[(1S, 4S)-2,5-diazabicyclobicyclo[2.2.1]hept-2-yl]phenyl} thiophene-3-carboxamide; and pharmaceutically acceptable salts thereof.

Unless otherwise indicated, the term "$C_1$–$C_6$ alkyl" referred to herein denotes a straight or branched chain alkyl group having from 1 to 6 carbon atoms. Examples of such groups include methyl, ethyl, n-propyl, i-propyl, n-butyl, i-butyl and t-butyl. The terms "$C_1$–$C_2$ alkyl" and "$C_1$–$C_4$ alkyl" are to be interpreted analogously.

Unless otherwise indicated, the term "$C_2$–$C_3$ alkenyl" referred to herein denotes a straight or branched chain alkyl group having 2 or 3 carbon atoms incorporating at least one carbon-carbon double bond. Examples of such groups include ethenyl and propenyl. The term "$C_2$–$C_6$ alkenyl" is to be interpreted analogously.

Unless otherwise indicated, the term "$C_2$–$C_3$ alkynyl" referred to herein denotes a straight chain alkyl group having 2 or 3 carbon atoms incorporating one carbon-carbon triple bond.

Examples of such groups include ethynyl and propynyl. The term "$C_2$–$C_6$ alkynyl" is to be interpreted analogously.

Unless otherwise indicated, the term "$C_3$–$C_6$ cycloalkyl" referred to herein denotes a saturated carbocyclic ring having from 3 to 6 carbon atoms. Examples of such groups include cyclopropyl, cyclopentyl and cyclohexyl.

Unless otherwise indicated, the term "$C_1$–$C_4$ alkoxy" referred to herein denotes a straight or branched chain alkoxy group having 1 to 4 carbon atoms. Examples of such groups include methoxy, ethoxy and isopropoxy. The terms "$C_1$–$C_2$ alkoxy" and "$C_1$–$C_6$ alkoxy" are to be interpreted analogously.

Unless otherwise indicated, the term "$C_1$–$C_2$ alkanoyl" referred to herein denotes a formyl or acetyl group.

Unless otherwise indicated, the term "halogen" referred to herein denotes fluoro, chloro, bromo and iodo.

Examples of a 5- to 7-membered heteroaromatic ring containing one to three heteroatoms selected independently from O, N and S include furan, thiophene, pyrrole, oxazole, isoxazole, thiazole, isothiazole, imidazole, pyrazole, triazole, pyridine, pyridazine, pyrimidine and pyrazine.

Examples of a 3- to 8-membered saturated or partially unsaturated monocyclic or saturated bicyclic ring system optionally incorporating one or two heteroatoms selected independently from O, N and S, and optionally incorporating a carbonyl group include cyclopropyl, cyclopentyl, cyclohexyl, tetrahydrofuran, tetrahydropyran, pyrrolidine, 3-pyrroline, piperidine, piperazine, 8-oxa-3-azabicyclo[3.2.1]octane, pyrrolidone, 2-oxa-5-azabicyclo[2.2.1]heptane, 1,4-oxazepane, 2,5-diazabicyclo[2.2.1]heptane, piperidone and morpholine.

Examples of a 5- or 6-membered saturated azacyclic ring optionally containing a further O, S or NR group include pyrrolidine, piperidine, piperazine and morpholine.

According to the invention there is also provided a process for the preparation of a compound of formula (I) or a pharmaceutically acceptable salt, enantiomer or racemate thereof which comprises:

(a) reaction of a compound of formula (II):

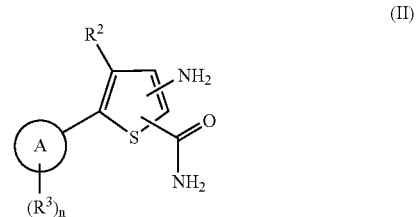

(II)

wherein A, $R^2$, $R^3$ and n are as defined in formula (I) with an isocyanate or an isothiocyanate or an acyl derivative, $R^1$—CO—L where L is a leaving group; or (b) reaction of compound of formula (III)

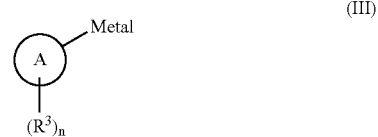

(III)

wherein $R^3$, n and A are as defined in formula (I) with a compound of formula (IV)

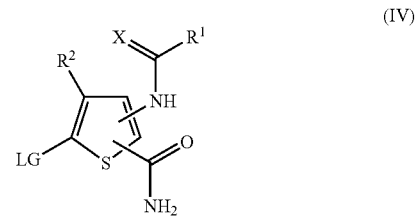

(IV)

wherein X, $R^1$ and $R^2$ are as defined in formula (I) and LG represents a leaving group; or (c) reaction of compound of formula (V)

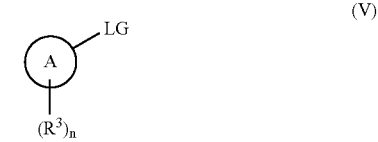

(V)

wherein $R^3$, n and A are as defined in formula (I) and LG represents a leaving group, with a compound of formula (VI)

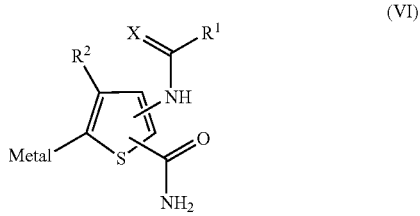

(VI)

wherein X, R¹ and R² are as defined in formula (I);

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), suitable isocyanate reagents include trimethylsilylisocyanate, trimethylsilylisothiocyanate, chlorosulphonylisocyanate, trichloroacetylisocyanate and sodium isocyanate. The reaction with trimethylsilylisocyanate or trimethylsilylisothiocyanate can be carried out in a solvent such as dichloromethane/dimethylformamide at a suitable elevated temperature, for example, at the reflux temperature of the reaction mixture. The reaction with chlorosulphonylisocyanate can be carried out in a solvent such as toluene at ambient temperature. The reaction with sodium isocyanate can be carried out in a suitable solvent system such as aqueous acetic acid at ambient temperature. The trichloroacetylisocyanate reaction can be carried out in a suitable solvent system such as acetonitrile at ambient temperature, and subsequently treating the mixture with ammonia to give compounds of the general formula (I). Suitable acyl derivatives of formula R¹—CO—L include acyl halides, particularly acyl chlorides, and acid anhydrides. Reactions with such acyl derivatives are generally carried out at ambient temperature in a suitable solvent such as pyridine, or in a solvent such as dichloromethane in the presence of a suitable base such as triethylamine or pyridine.

Compounds of formula (I) wherein X represents O may subsequently be converted into corresponding compounds of formula (I) wherein X represents S by reaction with, for example, Lawesson's reagent.

In processes (b) and (c), the compounds of formulae (III) and (IV) or of formulae (V) and (VI) are reacted together under catalysis provided by a complex of a transition metal such as palladium or nickel. In compounds of formulae (III) and (VI), under appropriate conditions, "metal" can be a metal or semi-metal such as magnesium, zinc, copper, tin, silicon, zirconium, aluminium or boron. Suitable leaving groups include iodo, bromo, chloro, triflate or phosphonate.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) can be prepared by standard chemistry described in the literature [for example, J. Het. Chem. 36, 333 (1999)] or by reaction of compounds of formula (VII):

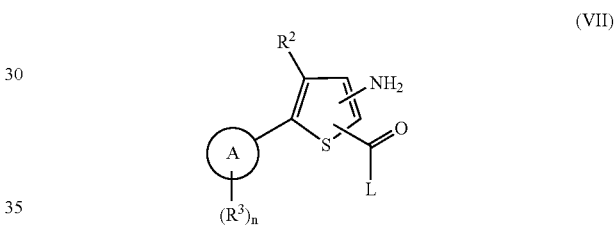

(VII)

where A, R², R³ and n are as defined in formula (I), and L represents a leaving group, with ammonia. Suitable groups L include halogen, in particular chloro.

Compounds of formula (VII) where L is halo can be prepared from the corresponding compound of formula (VIII):

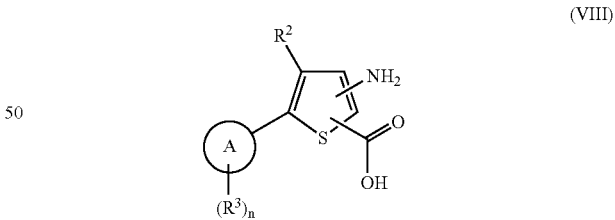

(VIII)

where A, R², R³ and n are as defined in formula (I), by treating with a halogenating agent such as thionyl chloride.

Compounds of formulae (III), (IV), (V), (VI) and (VIII) are commercially available or can be prepared using standard chemistry as exemplified herein.

Certain novel intermediate compounds form a further aspect of the invention.

The compounds of formula (I) have activity as pharmaceuticals, in particular as IKK-2 enzyme inhibitors, and may be used in the treatment (therapeutic or prophylactic) of conditions/diseases in human and non-human animals in which inhibition of IKK-2 is beneficial. Examples of such conditions/diseases include inflammatory diseases or diseases with an inflammatory component. Particular diseases include inflammatory arthritides including rheumatoid arthritis, osteoarthritis, spondylitis, Reiters syndrome, psoriatic arthritis, lupus and bone resorptive disease; multiple sclerosis, inflammatory bowel disease including Crohn's disease; asthma, chronic obstructive pulmonary disease, emphysema, rhinitis, myasthenia gravis, Graves' disease, allograft rejection, psoriasis, dermatitis, allergic disorders, immune complex diseases, cachexia, ARDS, toxic shock, heart failure, myocardial infarcts, atherosclerosis, reperfusion injury, AIDS, cancer and disorders characterised by insulin resistance such as diabetes, hyperglycemia, hyperinsulinemia, dyslipidemia, obesity, polycystic ovarian disease, hypertension, cardiovascular disease and Syndrome X.

The reported roles of NF-κB in both oncogenesis and chemoresistance suggest that inhibition of this pathway through the use of an IKK2 inhibitor, such as a small molecule IKK2 inhibitor, could provide a novel monotherapy for cancer and/or an important adjuvant therapy for the treatment of chemoresistant tumours.

We are particularly interested in diseases selected from asthma, rheumatoid arthritis, psoriasis, inflammatory bowel disease including Crohn's disease, multiple sclerosis, chronic obstructive pulmonary disease, bone resorptive disease, osteoarthritis, diabetes/glycaemic control and cancer.

Thus, the present invention provides a compound of formula (I), or a pharmaceutically acceptable salt thereof, as hereinbefore defined for use in therapy.

In a further aspect, the present invention provides the use of a compound of formula (I), or a pharmaceutically acceptable salt thereof, as hereinbefore defined in the manufacture of a medicament for use in therapy.

In a still further aspect, the present invention provides the use of a compound of formula (I), or a pharmaceutically acceptable salt thereof, as hereinbefore defined in the manufacture of a medicament for the treatment of diseases or conditions in which modulation of the IKK-2 enzyme activity is beneficial.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating an IKK-2 mediated disease which comprises administering to a patient a therapeutically effective amount of a compound of formula (I), or a pharmaceutically acceptable salt thereof, as hereinbefore defined.

The invention also provides a method of treating an inflammatory disease, especially asthma, rheumatoid arthritis or multiple sclerosis, in a patient suffering from, or at risk of, said disease, which comprises administering to the patient a therapeutically effective amount of a compound of formula (I), or a pharmaceutically acceptable salt thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the, pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conventional procedures for the selection and preparation of suitable pharmaceutical formulations are described in, for example, "Pharmaceuticals—The Science of Dosage Form Designs", M. E. Aulton, Churchill Livingstone, 1988.

The invention is illustrated, but in no way limited, by the following examples:

EXAMPLE 1

2-[(Aminocarbonyl)amino]-4-methyl-5-(4-biphenyl)-3-thiophenecarboxamide a) 2-Amino-4-methyl-5-(4-biphenyl)-3-thiophencarboxamide 4-Biphenyl acetone (2.0 g), cyanoacetamide (0.88 g), sulphur (0.37 g) and morpholine (1 ml) in ethanol (5 ml) were stirred and heated at 55° C. for 6 h. The reaction mixture was cooled and filtered before adding to water (150 ml). The precipitated solid was filtered off, washed with water and then dried. The product was then triturated with ether and collected.

MS (ES) 309 (M+H)$^+$. $^1$H NMR (DMSO-D6) 2.3 (s, 3H), 6.8 (s, 2H), 6.9 (s, 2H), 7.4 (m, 5H), 7.6 (m, 4H).

b) 2-[(Aminocarbonyl)amino]-4-methyl-5-(4-biphenyl)-3-thiophenecarboxamide

2-Amino-4-methyl-5-(4-biphenyl)-3-thiophencarboxamide (0.44 g) was dissolved in tetrahydrofuran (10 ml), cooled to 0° C. and trichloroacetylisocyanate (0.11 ml) added dropwise with stirring. Stirring was continued for a further 30 minutes at room temperature and then a solution of ammonia in methanol (8 ml of a 10% solution) was added and stirring was continued for a further 3 h. The solvent was evaporated and the residue treated with ethyl acetate and the product filtered off.

MS (ES) 350 (M−H)⁻. $^1$H NMR (DMSO-D6) 2.2 (s, 3H), 6.7 (s, 2H), 7.4 (m, 2H), 7.45 (m, 4H), 7.7 (m, 5H), 7.8 (m, 1H).

EXAMPLE 2

2-[(Aminocarbonyl)amino]-4-methyl-5-(4-[(3,5-dimethylisoxazol-4-yl)methoxy]phenyl)-3-thiophenecarboxamide a) The title compound was prepared from 4-[(3,5-dimethylisoxazol-4-yl)methoxy]phenyl acetone using the method of Example 1.

MS (ES) 399 (M−H)⁻. $^1$H NMR (DMSO-D6) 2.2 (s, 6H), 2.4 (s, 3H), 4.95 (s, 2H), 6.65 (m, 2H), 7.0 (m, 3H), 10.04 (brs, 1H).

b) 4-[(3,5-Dimethylisoxazol-4-yl)methoxy]phenyl acetone

A mixture of 4-hydroxyphenyl acetone (1.5 g), 4-chloromethyl-3,5-dimethylisoxazole (1.6 g) and potassium carbonate (1.5 g) in dimethylformamide (10 ml) was heated and stirred at 60° C. for 18 h. After cooling, the mixture was poured into water and extracted twice with ethyl acetate. The combined solvent phase was washed twice with brine, dried (magnesium sulphate) and then evaporated. The resultant oil was chromatographed on silica using isohexane to 20% ethyl acetate in isohexane mixtures to give the title compound (2.5 g).

MS (ES) 259 (M−H)⁻. $^1$H NMR (DMSO-D6) 2.05 (s, 3H), 2.2 (s, 3H), 2.4 (s, 3H), 3.6 (s, 2H), 4.85 (s, 2H), 6.9 (d, 2H), 7.1 (d, 2H).

EXAMPLE 3

2-[(Aminocarbonyl)amino]-4-methyl]-5-(4-[(4-chlorophenyl)methoxy]phenyl)-3-thiophenecarboxamide a) The title compound was prepared from 4-[(4-chlorophenyl)methoxy]phenyl acetone by the method of Example 1.

MS (ES) 414 (M−H)⁻. $^1$H NMR (DMSO-D6) 2.2 (s, 3H), 5.1 (s, 2H), 6.7 (br, 2H), 7.05 (d, 2H), 7.25 (m, 3H), 7.4 (m, 5H), 10.04 (m, 1H).

b) 4-[(4-Chlorophenyl)methoxy]phenyl acetone

Prepared from 4-chlorobenzyl chloride and 4-hydroxyphenyl acetone by the method of Example 2 (b).

MS (ES) 275 (M+H)⁺. $^1$H NMR (DMSO-D6) 2.05 (s, 3H), 3.6 (s, 2H), 5.0 (s, 2H), 6.9 (d, 2H), 7.05 (d, 2H), 7.4 (m, 4H).

EXAMPLE 4

2-[(Aminocarbonyl)amino]-4-methyl-5-(4-[(5-chlorothien-2-yl)methoxy]phenyl)-3-thiophenecarboxamide a) The title compound was prepared from 4-[(5-chlorothien-2-yl)methoxy]phenyl acetone by the method of Example 1.

MS (ES) 420 (M−H)⁻. $^1$H NMR (DMSO-D6) 2.2 (s, 3H), 5.2 (s, 2H), 6.7 (br, 2H), 7.1 (m, 4H), 7.3 (m, 4H), 10.04 (n, 1H).

b) 4-[(5-Chlorothien-2-yl)methoxy]phenyl acetone

Prepared by the method of Example 2 (b) from 2-chloromethyl-5-chlorothiophene and 4-hydroxyphenyl acetone.

MS (ES) 281 (M+H)⁺.

EXAMPLE 5

2-[(Aminocarbonyl)amino]methyl-5-4-[2-(2.2.6.6-tetramethylpiperidine-1-yl)ethoxy]phenyl}-3-thiophenecarboxamide a) The title compound was prepared from 2-amino-4-methyl-5-{4-[2-(2,2,6,6-tetramethylpiperidin-1-yl)ethoxy]phenyl}-3-thiophenecarboxamide by the method of Example 1 (b).

MS (ES) 459 (M+H)⁺. $^1$H NMR (DMSO-D6) 1.02 (s, 12H), 1.58–1.30 (m, 6H), 2.23 (s, 3H), 3.84 (t, 2H), 2.82 (t, 2H), 6.71 (bs, 2H), 6.96 (d, 2H), 7.23 (d, 2H), 7.26 (bs, 2H), 10.04 (s, 1H).

b) 2-Amino-4-methyl-5-{4-[2-(2,2,6,6-tetramethylpiperidin-1-yl)ethoxy]phenyl}-3-thioiphenecarboxamide Prepared from 4-[2-(2,2,6,6-tetramethylpiperidin-1-yl)ethoxy]phenyl acetone by the method of Example 1 (a).

MS (ES) 416 (M+H)⁺. $^1$H NMR (DMSO-D6) 1.02 (s, 12H), 1.30–1.41 (m, 4H), 1.45–1.55 (m, 2H), 2.19 (s, 3H), 2.80 (t, 2H), 3.83 (t, 2H), 6.75 (b, 2H), 6.84 (s, 2H), 6.93 (d, 2H), 7.18 (d, 2H).

c) 4-[2-(2,2,6,6-Tetramethylpiperidine-1-yl)ethoxy]phenyl acetone

Prepared from 2-(2,2,6,6-tetramethylpiperidin-1-yl)ethyl chloride and 4-hydroxyphenylacetone in a similar manner to Example 2 (b).

MS (ES) 318 (M+H)⁺. $^1$H NMR (DMSO-D6) 1.05 (s, 12H), 1.35–1.49 (m, 4H), 1.49–1.61 (m, 2H), 2.13 (s, 3H), 2.86 (t, 2H), 3.61 (s, 2H), 3.85 (t, 2H), 6.85 (d, 2H), 7.09 (d, 2H).

EXAMPLE 6

2-[(Aminocarbonyl)amino]-4-methyl-5-(4-[(thiazol-4-yl)methoxy]phenyl)-3-thiophenecarboxamide a) The title compound was prepared from 2-amino-4-methyl-5-(4-[(thiazol-4-yl)methoxy]phenyl)-3-thiophenecarboxamide by the method of Example 1.

MS (ES) 389 (MH)⁺. $^1$H NMR (DMSO-D6) 300 MHz δ 2.23 (s, 3H), 5.23 (s, 2H), 6.70 (s, 2H), 7.09 (d, 2H), 7.27 (d, 2H), 7.0–7.5 (bs, 3H), 7.79 (s, 1H), 9.11 (s, 1H).

b) 2-Amino-4-methyl-5-(4-[(thiazol-4-yl)methoxy]phenyl)-3-thiophenecarboxamide

Prepared from 4-[(thiazol-4-yl)methoxy]phenyl acetone by the method of Example 1.

MS (ES) 329 (M−NH3)⁺. $^1$H NMR (DMSO-D6) 300 MHz δ 2.20 (s, 3H), 5.22 (s, 2H), 6.77 (s, 2H), 6.85 (s, 2H), 7.05 (d, 2H), 7.20 (d, 2H), 7.77 (s, 1H), 9.11 (s, 1H)., c) 4-[(Thiazol-4-yl)methoxy]phenyl acetone Prepared from 4-chloromethylthiazole and 4-hydroxyphenylacetone by the method of Example 1.

MS (ES) 248 (MH)⁺. $^1$H NMR (DMSO-D6) 300 MHz δ 2.13 (s, 3H), 3.63 (s, 2H), 5.26 (s, 2H), 6.79 (d, 2H), 7.12 (d, 2H), 7.38 (s, 1H), 8.83 (s, 1H).

EXAMPLE 7

2-[(Aminocarbonyl)amino]-4-methyl-5-(4-[(1,2,5-thiadiazol-3-yl)methoxy]phenyl)-3-thiophenecarboxamide a) The title compound was prepared from 2-amino-4-methyl-5-(4-[(1,2,5-thiadiazol-3-yl)methoxy]phenyl)-3-thiophenecarboxamide by the method of Example 1.

MS (ES) 388 M$^-$. $^1$H NMR (DMSO-D6) 300 MHz δ 2.22 (s, 3H), 5.46 (s, 2H), 7.10 (d, 2H), 7.12 (bs, 2H), 7.23 (s, 2H), 7.30 (d, 2H), 8.97 (s, 1H).

b) 2-Amino-4-methyl-5-(4-[(1,2,5-thiadiazol-3-yl)methoxy]phenyl)-3-thiophenocarboxamide Prepared from 4-[(1,2,5-thiadiazol-3-yl)methoxy]phenyl acetone by the method of Example 1.

MS (ES) 347 M$^+$. $^1$H NMR (DMSO-D6) 300 MHz δ 2.20 (s, 3H), 5.45 (s, 2H), 6.76 (s, 2H), 7.08 (d, 2H), 7.23 (d, 2H), 8.95 (s, 1H).

c) 4-[(1,2,5-Thiadiazol-3-yl)methoxy]phenyl acetone

Prepared from 3-bromomethyl-1,2,5-thiadiazole and 4-hydroxyphenylacetone by the method of Example 1.

MS (ES) 249 (MH)$^+$. $^1$H NMR CDCl$_3$ 300 MHz δ 2.15 (s, 3H), 3.63 (s, 2H), 5.36 (s, 2H), 6.96 (d, 2H), 7.14 (d, 2H), 8.68 (s, 1H).

EXAMPLE 8

2-[(Aminocarbonyl)amino]-4-methyl-5-(4-[(1-methylperhydroazepin-3-yl)oxy]phenyl)-3-thiophenecarboxamide a) The title compound was prepared from 2-amino-4-methyl-5-(4-[(1-methylperhydroazepin-3-yl)oxy]phenyl)-3-thiophenecarboxamide by the method of Example 1.

MS (ES) 403 (MH)$^+$. $^1$H NMR (DMSO-D6) 300 MHz δ 1.62 (m, 1H), 1.72 (m, 2H), 2.00 (m, 1H), 2.35–2.60 (m, 3H), 2.70 (m, 2H), 2.90 (m, 1H), 4.56 (m, 1H), 6.70 (s, 2H), 6.95 (d, 2H), 7.24 (bs, 2H; d, 2H), 10.04(s, 1H).

b) 2-Amino-4-methyl-5-(4-[(1-methylperhydroazepin-3-yl)oxy]phenyl)-3-thiophenecarboxamide Prepared from 4-[(1-methylperhydroazepin-3-yl)oxy]phenyl acetone by the method of Example 1.

MS (ES) 360 (MH)$^+$. $^1$H NMR CDCl$_3$ 300 MHz δ 2.03 (m, 2H), 2.12 (m, 2H), 2.56 (m, 1H), 2.70 (m, 3H), 2.90 (m, 2H), 4.50 (m, 1H), 5.53 (s, 2H), 6.20 (s, 2H), 6.89 (d, 2H), 7.22 (d, 2H).

c) 4-[(1-Methylperhydroazepin-3-yl)oxy]phenyl acetone

Prepared from 1-methyl-2-chloromethylpiperidine and 4-hydroxyphenylacetone by the method of Example 1 to give a mixture (50:50) of the above product and 4-([1-methyl-piperidin-2-yl]methoxy)phenyl acetone.

MS (ES) 262 (MH)$^+$.

EXAMPLE 9

2-[(Aminocarbonyl)amino]-5-[6-(pyrrolidin-1-yl)pyridin-3-yl]-3-thiophenecarboxamide a) 2-Amino-3-thiophenecarboxamide A suspension of 2,5-dihydroxy-1,4-dithiane (25 g) and cyanoacetamide (19.3 g) in ethanol (120 ml) was stirred and heated to 50° C. Triethylamine (9.2 ml) was added over 15 minutes and the mixture was stirred at 50° C. for a further 2 h. After cooling in ice, the solid was filtered off and dried (21.4 g).

MS (ES) 143 (M+H)$^+$.

b) 2-[(Aminocarbonyl)amino]-3-thiophenecarboxamide

2-Amino-3-thiophenecarboxamide (0.44 g) was suspended in acetonitrile (25 ml) and trichloroacetylisocyanate (0.2 ml) added dropwise with stirring over 10 minutes. Stirring was continued for a further 3 h at room temperature and then a solution of ammonia in methanol (10 ml of a 2M solution) was added and stirring continued for a further 2 h. The solvent was evaporated and the residue treated with water. The resultant solid was filtered off and washed with more water. Trituration with ether gave the title urea (0.2 g).

MS (ES) 186 (M+H)$^+$.

c) 2-[(Aminocarbonyl)amino]-5-bromo-3-thiophenecarboxamide

2-[(Aminocarbonyl)amino]-3-thiophenecarboxamide (1.0 g) was dissolved in acetic acid (20 ml) and a solution of bromine (0.35 ml) in acetic acid (5 ml) was added over 5 minutes with rapid stirring. The mixture was stirred for 90 minutes and then added to water (50 ml). The product was filtered off and washed with water and dried under vacuum (0.55 g).

MS (ES) 262/264 (M–H)$^-$. $^1$H NMR (DMSO-D6) 7.15 (m, 1H), 7.35 (m, 1H), 7.8 (s, 1H), 7.9 (m, 1H), 10.63 (brs, 1H).

d) 5-Iodo-2-pyrrolidin-1-yl pyridine

Pyrrolidine (1.74 ml) was added to 2-chloro-5-iodopyridine (1 g) in dimethylacetamide (5 ml) and the solution heated at 120° C. for 4 h. After cooling, the reaction mixture was poured into water (60 ml) and the solid precipitate collected by filtration. Recrystallisation from ethyl acetate gave the product as off-white needles (0.33 g); the remaining material was adsorbed onto silica and purified by column chromatography eluting with 0 to 3% ethyl acetate in hexane to give a white solid (0.65 g).

MS (ES) 275 (M+H)$^+$. $^1$H NMR (DMSO-D6) 1.84–1.98 (m, 4H), 3.24–3.37 (m, 4H), 6.33 (d, 1H), 7.67 (dd, 1H), 8.16 (d, 1H).

e) 2-[(Aminocarbonyl)amino]-5-[6-(pyrrolidin-1-yl)pyridin-3-yl]-3-thiophenecarboxamide 2-Pyrrolidinyl-5-iodopyridine (0.778 g) was stirred in tetrahydrofuran (20 ml) under argon. Triisopropylborate (1.31 ml) was added the solution was cooled to –78° C. n-Butyl lithium (2.66 ml, 1.6M solution in hexane) was added dropwise. The reaction mixture was stirred at –78° C. for 5 minutes then allowed to warm to room temperature and stirred for a further 30 minutes. The mixture was then evaporated to dryness. 1,2-Dimethoxyethane (20 ml) was added to the residue and purged with a stream of argon.

2-[(Aminocarbonyl)amino]-5-bromo-3-thiophenecarboxamide (0.250 g) was then added followed by saturated aqueous sodium hydrogen carbonate (7 ml) and Pd(PPh$_3$)$_4$ (100 mg). The mixture was heated at 90° C. under argon for 18 h. After cooling, the solvent was removed in vacuo and the residue taken up in 2M aqueous sodium hydroxide (30 ml) and 10% methanol in dichloromethane (40 ml). The layers were separated and the organic phase extracted with a further portion of 2M aqueous sodium hydroxide (20 ml). The solid remaining undissolved at the interface was collected by filtration, Washed with water and dichloromethane and dried to give the product as a pale brown solid (0.219 g).

MS (ES) 332 (M+H)$^+$. $^1$H NMR (DMSO-D6) 1.83–2.01 (m, 4H), 3.28–3.46 (m, 4H), 6.47 (d, 1H), 6.87 (bs, 2H), 7.23 (bs, 1H), 7.43 (s, 1H), 7.58 (bs, 1H), 7.58 (dd, 1H), 8.20 (d, 1H), 10.91 (s, 1H).

EXAMPLE 10

2-[(Aminocarbonyl)amino]-5-[6-(2,2-difluoroethoxy)pyridin-3-yl]-3-thiophenecarboxamide a) 5-Bromo-2-(2,2-difluoroethoxy)pyridine (0.541 g) was stirred in (10 ml) under argon. Triisopropylborate (1.05 ml) was added and the solution was cooled to −78° C. Butyl lithium (2.13 ml, 1.6M solution in hexane) was added dropwise. The mixture was then allowed to warm to room temperature and stirring continued for 1 h. The tetrahydrofuran was removed in vacuo, dimethoxyethane (12 ml) was added and the mixture was purged with argon. 2-[(Aminocarbonyl)amino]-5-bromo-3-thiophenecarboxamide was added, followed by sodium hydrogen carbonate (3.5 ml of a saturated aqueous solution) and $Pd(PPh_3)_4$ (100 mg). The mixture was heated at 90° C. for 6 h under argon, then allowed to cool and stirred at room temperature for 18 h. The solvent was removed in vacuo and the residue taken up in 2M aqueous sodium hydroxide (30 ml) and 10% methanol in dichloromethane (40 ml). The layers were separated and the organic phase washed with a further portion of 2M aqueous sodium hydroxide (20 ml). The combined aqueous layers were washed with dichloromethane (40 ml), then filtered and the filtrate neutralised with 6M aqueous hydrochloric acid. The resultant precipitate was collected by filtration, washed with water and dried to give the product as a pale brown solid (146 mg).

MS (ES) 343(M+H)$^+$. $^1$H NMR (DMSO-D6) 4.57 (td, 2H), 6.38 (tt, 1H), 6.94 (bs, 2H), 6.96 (d, 1H), 7.30 (bs, 1H), 7.63 (bs, 1H), 7.67 (s, 1H), 7.87 (dd, 1H), 8.30 (d, 1H), 10.97 (s, 1H).

b) 5-Bromo-2-(2,2-difluoroethoxy)pyridine 2,2-Difluoroethanol (0.40 ml) was added dropwise to a suspension of sodium hydride (0.270 g) in dimethylformamide (5 ml) cooled in an ice-bath under argon. The mixture was stirred at room temperature for 40 minutes, then re-cooled in an ice-bath. A solution of 2,5-dibromopyridine (1 g) in dimethylformamide (5 ml) was added. The solution was then heated at 65° C. under argon for 18 h, allowed to cool and diluted with water (50 ml). The aqueous phase was extracted three times with ethyl acetate. The combined extracts were washed with water, brine, dried over magnesium sulphate, filtered and evaporated. The product was purified by column chromatography eluting with hexane to give a colourless oil (0.946 g).

MS (CI) 238 (M+H)$^+$. $^1$H NMR (DMSO-D6) 4.50 (td, 2H), 6.10 (tt, 1H), 6.74 (d, 1H), 7.70 (dd, 1H), 8.18 (d, 1H).

EXAMPLE 11

2-[(Aminocarbonyl)amino]-5-[6-(piperidin-1-yl)pyridin-3-yl]-3-thiophenecarboxamide a) The title compound was prepared from 5-iodo-2-piperidinylpyridine in a similar manner to Example 10 (a).

MS (ES) 346 (M+H)$^+$. $^1$HNMR (DMSO-D6) 1.44–1.66 (m, 6H), 3.44–3.58 (m, 4H), 6.84 (d, 1H), 6.90 (bs, 2H), 7.24 (bs, 1H), 7.47 (s, 1H), 7.56 (bs, 1H), 7.60 (dd, 1H), 8.23 (d, 1H), 10.92 (s, 1H).

b) 5-Iodo-2-piperidinylpyridine

Prepared from 2-chloro-5-iodopyridine and piperidine by the method of Example 9 (d).

MS (ES) 289 (M+H)$^+$. $^1$H NMR (DMSO-D6) 1.43–1.64 (m, 6H), 3.41–3.52 (m, 4H), 6.69 (d, 1H), 7.68 (dd, 1H), 8.20 (d, 1H).

EXAMPLE 12

2-[(Aminocarbonyl)amino]-5-[6-(cyclopentyloxy)pyridin-3-yl]-3-thiophenecarboxamide a) The title compound was prepared from 5-bromo-2-(cyclopentyloxy)pyridine in a similar manner to Example 10 (a).

MS (ES) 347 (M+H)$^+$. $^1$H NMR (DMSO-D6) 1.46–1.78 (m, 6H), 1.83–2.02 (m, 2H), 5.30–5.40 (m, 1H), 6.78 (d, 1H), 6.93 (bs, 2H), 7.29 (bs, 1H), 7.60 (bs, 1H), 7.60 (s, 1H), 7.76 (dd, 1H), 8.25 (d, 1H), 10.95 (s, 1H).

b) 5-Bromo-2-(cyclopentyloxy)pyridine

Prepared from 2,5-dibromopyridine and cyclopentanol by the method of Example 10 (b).

MS (EI) 241 (M)$^+$. $^1$H NMR (DMSO-D6) 1.54–2.05 (m, 8H), 5.28–5.37 (m, 1H), 6.58 (d, 1H), 7.60 (dd, 1H), 8.17 (d, 1H).

EXAMPLE 13

2-[(Aminocarbonyl)amino]-5-[6-(4-ethanesulfonylpiperazin-1-yl)pyridin-3-yl]-3-thiophenecarboxamide a) The title compound was prepared from 5-bromo-2-(4-ethanesulphonylpiperazin-1-yl) pyridine in a similar manner to Example 9 (e).

MS (ES) 439 (M+H)$^+$. $^1$H NMR (DMSO-D6) 1.21 (t, 3H), 3.07 (q, 2H), 3.18–3.30 (m, 4H), 3.53–3.66 (m, 4H), 6.90 (bs, 2H), 6.94 (d, 1H), 7.30 (bs, 1H), 7.54 (s, 1H), 7.60 (bs, 1H), 7.68 (dd, 1H), 8.25 (d, 1H), 10.94 (s, 1H).

b) 5-Bromo-2-(4-ethanesulfonylpiperazin-1-yl)pyridine 2,5-Dibromopyridine (1 g) was heated in dimethylacetamide (2.5 ml) with ethanesulfonylpiperazine (0.752 g) and diisopropylethylamine (1.84 ml) at 120° C. for 18 h. After cooling, the reaction mixture was poured into water (30 ml) and the precipitated solid was collected by filtration. The product was purified by column chromatography eluting with dichloromethane (0.50 g).

MS (ES) 334 (M+H)$^+$. $^1$H NMR (DMSO-D6) 1.40 (t, 3H), 2.98 (q, 2H), 3.35–3.43 (m, 4H), 3.57–3.66 (m, 4H), 6.56 (d, 1H), 7.56 (dd, 1H), 8.21 (d, 1H).

EXAMPLE 14

2-[(Aminocarbonyl)amino]-5-[6-[(tetrahydrofuran-2-yl)methoxy]pyridin-3-yl]-3-thiophenecarboxamide a) The title compound was prepared from 5-bromo-2-[(tetrahydrofuran-2-yl)methoxy]pyridine in a similar manner to Example 10 (a).

MS (ES) 363 (M+H)$^+$. $^1$H NMR (DMSO-D6) 1.55–2.05 (m, 4H), 3.59–3.82 (m, 2H), 4.07–4.30 (m, 3H), 6.85 (d, 1H), 6.94 (bs, 2H), 7.29 (bs, 1H), 7.60 (bs, 1H), 7.60 (s, 1H), 7.80 (dd, 1H), 8.25 (d, 1H), 10.96 (s, 1H).

b) 5-Bromo-2-[(tetrahydrofuran-2-yl)methoxy]pyridine

Prepared from 2,5-dibromopyridine and tetrahydrofuran-2-methanol by the method of Example 10 (b).

MS (CI) 258 (M+H)$^+$. $^1$H NMR (DMSO-D6) 1.63–2.12 (m, 4H), 3.77–3.98 (m, 2H), 4.14–4.38 (m, 3H), 6.71 (d, 1H), 7.63 (dd, 1H), 8.15 (d, 1H).

EXAMPLE 15

2-[(Aminocarbonyl)amino]-5-{3-[6-(furan-2-yl-methoxy)]-pyridine}-3-thiophenecarboxamide a) The title compound was prepared from 5-bromo-2-(furan-2-ylmethoxy)-pyridine in a similar manner to Example 10 (a).

MS (ES) 359 (M+H)$^+$. $^1$H NMR (DMSO-D6) 5.30 (s, 2H), 6.44 (m, 1H), 6.55 (d, 1H), 6.87 (d, 1H), 6.94 (bs, 2H), 7.29 (bs, 1H), 7.62 (bs, 1H), 7.62 (s, 1H), 7.67 (d, 1H), 7.82 (dd, 1H), 8.30 (d, 1H), 10.96 (s, 1H).

b) 5-Bromo-2-(furan-2-ylmethoxy)-pyridine

Prepared from 2,5-dibromopyridine and 2-furanmethanol by the method of Example 10 (b).

MS (EI) 253 (M)$^+$. $^1$H NMR (DMSO-D6) 5.27 (s, 2H), 6.44 (t, 1H), 6.53 (d, 1H), 6.84 (d, 1H), 7.67 (s, 1H), 7.89 (dd, 1H), 8.29 (d, 1H).

EXAMPLE 16

2-[(Aminocarbonyl amino]-5-{3-[6-(4-acetyl)piper-azin-1-yl]-pridine}-3-thiophenecarboxamide a) The title compound was prepared from 1-[4-(5-bromo-pyridin-2-yl)piperazin-1-yl]ethanone in a similar manner to Example 10 (a) but using t-butyl lithium (2 eq.) in place of n-butyl lithium.

MS (ES) 389 (M+H)$^+$. $^1$H NMR (DMSO-D6) 2.03 (s, 3H), 3.43–3.61 (m, 8H), 6.90 (bs, 2H), 6.90 (d, 1H), 7.26 (bs, 1H), 7.52 (s, 1H), 7.60 (bs, 1H), 7.67 (dd, 1H), 8.27 (d, 1H), 10.93 (s, 1H).

b) 1-[4-(5-Bromo-pyridin-2-yl)piperazin-1-yl]ethanone

Prepared from 2,5-dibromopyridine and 1-acetylpiperazine by the method of Example 13 (b).

MS (ES) 284 (M+H)$^+$. $^1$H NMR (DMSO-D6) 2.13 (s, 3H), 3.43–3.50 (m, 2H), 3.52–3.64 (m, 4H), 3.68–3.78 (m, 2H), 6.54 (d, 1H), 7.56 (dd, 1H), 8.20 (d, 1H).

EXAMPLE 17

(R)-2-[(Aminocarbonyl)amino]-5-{3-[6-(tetrahydrofuran-3-yloxy]-pyridine}-3-thioiphenecarboxamide a) The title compound was prepared from (R)-5-bromo-2-(tetrahydrofuran-3-yloxy)-pyridine in a similar manner to Example 10 (a).

MS (ES) 349 (M+H)$^+$. $^1$H NMR (DMSO-D6) 1.90–2.04 (m, 1H), 2.13–2.30 (m, 1H), 3.68–3.95 (m, 4H), 5.45–5.54 (m, 1H), 6.85 (d, 1H), 6.94 (bs, 2H), 7.30 (bs, 1H), 7.60 (bs, 1H), 7.60 (s, 1H), 7.80 (dd, 1H), 8.25 (d, 1H), 10.95 (s, 1H).

b) (R)-5-Bromo-2-(tetrahydrofuran-3-yloxy)-pyridine

Prepared from 2,5-dibromopyridine and (R)-3-hydroxytetrahydrofuran by the method of Example 10 (b).

MS (ES) 244 (M+H)$^+$. $^1$H NMR (DMSO-D6) 2.03–2.33 (m, 2H), 3.83–4.07 (m, 4H), 5.46–5.54 (m, 1H), 6.65 (d, 1H), 7.63 (dd, 1H), 8.16 (d, 1H).

EXAMPLE 18

2-[(Aminocarbonyl)amino]-5-{3-[6-(1-isopropyl-pyrrolidin-3-yloxy)]-pyridine}-3-thiophenecarboxamide a) The title compound was prepared from 5-bromo-2-(1-isopropyl-pyrrolidin-3-yloxy)-pyridine in a similar manner to Example 10 (a).

MS (ES) 390 (M+H)$^+$. $^1$H NMR (DMSO-D6) 0.99 (d, 3H), 1.02 (d, 3H), 1.69–1.87 (m, 1H), 2.15–2.94 (m, 6H), 5.28–5.38 (m, 1H), 6.83 (d, 1H), 7.94 (bs, 2H), 7.29 (bs, 1H), 7.60 (bs, 1H), 7.60 (s, 1H), 7.77 (dd, 1H), 8.25 (d, 1H), 10.95 (s, 1H).

b) 5-Bromo-2-(1-isopropyl-pyrrolidin-3-yloxy)-pyridine

Prepared from 2,5-dibromopyridine and 1-isopropylpyrrolidin-3-ol by the method of Example 10 (b).

MS (ES) 285 (M+H)$^+$. $^1$H NMR (DMSO-D6) 1.10 (d, 3H), 1.12 (d, 3H), 1.88–2.02 (m, 1H), 2.25–2.53 (m, 3H), 2.80–2.96 (m, 3H), 5.32–5.43 (m, 1H), 6.64 (d, 1H), 7.60 (dd, 1H), 8.15 (d, 1H).

EXAMPLE 19

2-[(Aminocarbonyl)amino]-5-{3-[6-(1-t-butyloxy-carbonyl-piperidin-4-yloxy)]-pyridine}-3-thiophenecarboxamide a) The title compound was prepared from 2-(1-t-butyloxycarbonyl-piperidin-4-yloxy)-5-bromopyridine in a similar manner to Example 10 (a).

MS (ES) 462 (M+H)$^+$. $^1$H NMR (DMSO-D6) 1.39 (s, 9H), 1.46–1.62 (m, 2H), 1.87–2.00 (m, 2H), 3.08–3.25 (m, 2H), 3.61–3.73 (m, 2H), 5.10–5.23 (m, 1H), 6.84 (d, 1H), 6.94 (bs, 2H), 7.29 (bs, 1H), 7.60 (bs, 1H), 7.60 (s, 1H), 7.80 (dd, 1H), 8.25 (d, 1H), 10.96 (s, 1H).

b) 2-[1-(t-Butyloxycarbonyl)-piperidin-4-yloxy]-5-bromopyridine

Prepared from 2,5-dibromopyridine and 1-t-butyloxycarbonylpiperidin-4-ol by the method of Example 10 (b).

MS (CI) 357 (M+H)$^+$. $^1$H NMR (DMSO-D6) 1.48 (s, 9H), 1.62–1.78 (m, 2H), 1.89–2.02 (m, 2H), 3.20–3.34 (m, 2H), 3.68–3.83 (m, 2H), 5.10–5.21 (m, 1H), 6.62 (d, 1H), 7.63 (dd, 1H), 8.14 (d, 1H).

EXAMPLE 20

2-[(Aminocarbonyl)amino]-5-{3-[6-(piperidin-4-yloxy)]-pyridine}-3-thiophenecarboxamide 2-[(Aminocarbonyl)amino]-5-{3-[6-(1-t-butyloxycarbonyl-piperidin-4-yloxy)-pyridine}-3-thiophenecarboxamide (65 mg) was stirred in dichloromethane (3 ml). Trifluoroacetic acid (3 ml) was added and stirring continued at room temperature for 1.5 h. Volatile materials were removed in vacuo, the residue was re-dissolved in dichloromethane and the solution added to saturated aqueous sodium hydrogen carbonate (3 ml). The dichloromethane was removed in vacuo and the solid product collected by filtration, washed with water and dried (28 mg).

MS (ES) 362 (M+H)$^+$. $^1$H NMR (DMSO-D6) 1.42–1.58 (m, 2H), 1.87–2.00 (m, 2H), 2.51–2.69 (m, 2H), 2.90–3.03 (m, 2H), 4.95–5.10 (m, 1H), 6.81 (d, 1H), 6.92 (bs, 2H), 7.28 (bs, 1H), 7.57 (bs, 1H), 7.57 (s, 1H), 7.77 (dd, 1H), 8.23 (d, 1H).

EXAMPLE 21

2-[(Aminocarbonyl)amino]-5-{3-[6-(1-(2-methoxy-ethyl)-piperidin-4-yloxy)]-pyridine}-3-thiophenecarboxamide a) The title compound was prepared from 5-bromo-2-(1-methoxyethylpiperidin-4-yloxy)-pyridine in a similar manner to Example 10 (a).

MS (ES) 420 (M+H)$^+$. $^1$H NMR (DMSO-D6) 1.57–1.74 (m, 2H), 1.95–2.01 (m, 2H), 2.23–2.40 (m, 2H), 2.40–2.60 (m, 2H), 2.64–2.85 (m, 2H), 3.22 (s, 3H), 3.43 (t, 2H), 4.92–5.05 (bs, 1H), 6.81 (d, 1H), 6.93 (bs, 2H), 7.28 (bs, 1H), 7.60 (bs, 1H), 7.60 (s, 1H), 7.77 (dd, 1H), 8.24 (d, 1H), 10.95 (s, 1H).

b) 5-Bromo-2-(1-methoxyethylpiperidin-4-yloxy)-pyridine

5-Bromo-2-(piperidin-4-yloxy)pyridine trifluoroacetate (0.86 g) was stirred with potassium carbonate (0.838 g) in dimethylacetamide (5 ml). Bromoethyl methyl ether (0.342 ml) was is added and the mixture was heated at 80° C. for 20 minutes. After cooling the mixture was poured into water (30 ml) and extracted three times with ether. The combined extracts were washed with water, dried over magnesium sulfate, filtered and evaporated. The residue was purified by column chromatography eluting with 0 to 2% 2M methanolic ammonia in dichloromethane to give the product as a colourless oil (0.71 g).

MS (ES) 315 (M+H)$^+$. $^1$H NMR (DMSO-D6) 1.74–1.90 (m, 2H), 1.96–2.10 (m, 2H), 2.28–2.43 (m, 2H), 2.60 (t, 2H), 2.73–2.86 (m, 2H), 3.36 (s, 3H), 3.52 (t, 2H), 4.94–5.06 (m, 1H), 6.62 (d, 1H), 7.60 (dd, 1H), 8.14 (d, 1H).

c) 5-Bromo-2-(piperidin-4-yloxy)pyridine trifluoroacetate

2-[1-(t-Butyloxycarbonyl)-piperidin-4-yloxy]-5-bromopyridine was stirred in dichloromethane (8 ml). Trifluoroacetic acid (5 ml) was added and stirring continued at room temperature for 1.5 h. Volatile materials were removed in vacuo and the residue was triturated with ether and hexane, then collected by filtration to give the product as a white solid (0.86 g).

MS (ES) 257 (M+H)$^+$. $^1$H NMR (DMSO-D6) 2.06–2.32 (m, 4H), 3.12–3.27 (m, 2H), 3.27–3.47 (m, 2H), 5.25–5.38 (m, 1H), 6.68 (d, 1H), 7.69 (dd, 1H), 8.16 (dd, 1H), 9.42 (bs, 1H), 9.57 (bs, 1H).

EXAMPLE 22

2[(Aminocarbonyl)amino]-5-{3-[6-(N-methanesulphonyl-piperidin-4-yloxy]-pyridine}-3-thiophenecarboxamide 2-[(N-Methanesulphonyl)piperidinyl-4-oxy]-5-bromopyridine (0.335 g) was dissolved in tetrahydrofuran (10 ml) and cooled to −78° C. Triisopropyl borate (0.46 ml) was added followed by dropwise addition of n-butyl lithium (1.0 ml, 1.6M solution in hexane). The reaction mixture was allowed to warm to room temperature and stirred for 1 h. The solvent was then evaporated off and the residue dissolved in a mixture of 1,2-dimethoxyethane (8 ml) and water (1 ml) and purged with a stream of argon. 2-[(Aminocarbonyl)amino]-5-bromo-3-thiophenecarboxamide (0.137 g) was then added followed by sodium carbonate (30 mg) and Pd(PPh$_3$)$_4$ (100 mg). The mixture was heated at 90° C. under argon for 6 h. The reaction was cooled, filtered and evaporated to dryness. The residue was partitioned between 3N aqueous sodium carbonate and dichloromethane and the solid interlayer was filtered off. The crude product was washed with water and then with a 10% methanol in dichloromethane mixture. The solid was chromatographed on silica using 10% methanol in dichloromethane as eluent to give the required product (20 mg).

MS (ES) 440 (M+H)$^+$. $^1$H NMR (DMSO-D6) 1.8 (m, 2H), 2.0 (m, 2H), 2.9 (s, 3H), 3.1 (m, 2H), 3.4 (m, 2H), 5.15 (m, 1H), 6.8 (d, 1H), 6.95 (m, 2H), 7.2 (m, 1H), 7.6 (s, 1H), 7.65 (m, 1H), 7.8 (d, 1H), 8.2 (s, 1H), 10.96 (m, 1H).

The preparation of the starting material was achieved as follows:

a) 2-(Piperidine-4-oxy)-5-bromopyridine

Prepared from 2,5-dibromopyridine and 4-hydroxypiperidine by the method of Example 10 (b).

$^1$H NMR (CDCl$_3$) 1.6 (m, 2H), 2.1 (m, 2H), 2.8 (m, 2H), 3.2 (m, 2H), 5.0 (m, 1H), 6.6 (m, 1H), 7.6 (m, 1H), 8.15 (m, 1H).

b) 2-[(N-methanesulphonyl)piperidinyl-4-oxy]-5-bromopyridine

A solution of 2-(piperidinyl-4-oxy)-5-bromopyridine (4.4 g) and triethylamine (7.2 ml) in dichloromethane (150 ml) was cooled in an ice bath under argon and a solution of mesyl chloride (1.9 ml) in dichloromethane (50 ml) was added dropwise with stirring. After the addition was complete the solution was stirred for a further 18 h at room temperature. The mixture was diluted with more dichloromethane and washed with water then brine and dried (sodium sulphate). The solvent was evaporated off and the residue washed with isohexane and the solid product was filtered off (3.8 g).

MS (ES) 335 (M+H)$^+$. $^1$H NMR (DMSO-D6) 1.7 (m, 2H), 2.0 (m, 2H), 2.9 (s, 3H), 3.1 (m, 2H), 3.35 (m, 2H), 5.1 (m, 1H), 6.8 (m, 1H), 7.9 (m, 1H), 8.3 (m, 1H).

EXAMPLE 23

2-[(Aminocarbonyl)amino]-5-{3-[6-(4,4-difluoropiperidin-1-yl)pyridine}-3-thiophenecarboxamide a) The title compound was prepared from 5-bromo-2-(4,4-difluoro-piperidin-1-yl)pyridine in a similar manner to Example 9 (e).

MS (ES) 346 (M+H)$^+$. $^1$H NMR (DMSO-D6) 1.44–1.66 (m, 6H), 3.44–3.58 (m, 4H), 6.84 (d, 1H), 6.90 (bs, 2H), 7.24 (bs, 1H), 7.47 (s, 1H), 7.56 (bs, 1H), 7.60 (dd, 1H), 8.23 (d, 1H), 10.92 (s, 1H).

b) 5-Bromo-2-(4.4-difluoro-piperidin-1-yl)pyridine 2,5-Dibromopyridine (1.30 g) was heated with 4,4-difluoropiperidine (2 g) in dimethylacetamide (4 ml) at 120° C. for 24 h, then at 150° C. for 8 h. The solution was allowed to cool, then poured into water (30 ml). The aqueous phase was extracted with ether (×3) and the combined extracts washed with water, dried over magnesium sulfate, filtered and evaporated. Purification by column chromatography gave the product as a colourless oil (0.70 g).

MS (ES) 277 (M+H)$^+$. $^1$H NMR (DMSO-D6) 1.85–2.10 (m, 4H), 3.63–3.75 (m, 4H), 6.60 (d, 1H), 7.55 (dd, 1H), 8.18 (d, 1H).

EXAMPLE 24

2-[(Aminocarbonyl)amino]-5-{3-[6-(pyrrolidin-1-yl)-5-methyl]pyridine}-3-thiophenecarboxamide a) The title compound was prepared from 5-iodo-3-methyl-2-(pyrrolidin-1-yl)-pyridine in a similar manner to Example 9 (e).

MS (ES) 346 (M+H)$^+$. $^1$H NMR (DMSO-D6) 1.76–1.92 (m, 4H), 2.31 (s, 3H), 3.40–3.52 (m, 4H), 6.89 (bs, 2H), 7.25 (bs, 1H), 7.43 (d, 1H), 7.47 (s, 1H), 7.58 (bs, 1H), 8.07 (d, 1H), 10.92 (s, 1H).

b) 5-Iodo-3-methyl-2-(pyrrolidin-1-yl)-pyridine

Prepared from 2-bromo-5-iodo-3-methylpyridine (*J. Org. Chem.* 1995, 60 (10), 5358) in a similar manner to Example 9 (d).

MS (ES) 289 (M+H)⁺. ¹H NMR (DMSO-D6) 1.85–1.97 (m, 4H), 2.27 (s, 3H), 3.44–3.56 (m, 4H), 7.48 (d, 1H), 8.15 (d, 1H).

EXAMPLE 25

2-[(Aminocarbonyl)amino]-5-{3-[6-(thien-2-ylmethoxy)]pyridine}-3-thiophenecarboxamide a) The title compound was prepared from 2-(thien-2-ylmethoxy)-5-bromopyridine by the method of Example 22.

MS (ES) 375 (M+H)⁺. ¹H NMR (DMSO-D6) 5.5 (s, 2H), 6.95 (m, 4H), 7.2 (s, 1H), 7.25 (m, 1H), 7.5 (m, 1H), 7.6 (m, 2H), 7.8 (m, 1H), 8.3 (s, 1H), 10.96 (brs, 1H).

b) 2-(Thien-2-ylmethoxy)-5-bromopyridine

Prepared from 2,5-dibromopyridine and thiophen-2-methanol by the method of Example 10 (b).

¹H NMR (DMSO-D6) 5.5 (s, 2H), 6.65 (m, 1H), 7.0 (m, 1H), 7.1 (m, 1H), 7.3 (m, 1H), 7.6 (m, 1H), 8.2 (m, 1H).

EXAMPLE 26

2-[(Aminocarbonyl)amino]-5-{3-[6-(cyclopentylmethoxy)]pyridine}-3-thiophenecarboxamide a) The title compound was prepared from 2-cyclopentylmethoxy-5-bromopyridine by the method of Example 22.

MS (ES) 361 (M+H)⁺. ¹H NMR (DMSO-D6) 1.3 (m, 2H), 1.6 (m, 4H), 1.8 (m, 2H), 2.3 (m, 1H), 4.1 (d, 2H), 6.8 (d, 1H), 6.95 (m, 2H), 7.3 (brs, 1H), 7.6 (m, 2H), 7.8 (m, 1H), 8.25 (m, 1H), 10.96 (brs, 1H).

b) 2-Cyclopentylmethoxy-5-bromopyridine

Prepared from 2,5-dibromopyridine and cyclopentylmethanol by the method of Example 10 (b).

MS (ES) 256 (M+H)⁺.

EXAMPLE 27

2-[(Aminocarbonyl)amino]-5-[3-(6-benzyloxy)pyridine]-3-thiophenecarboxamide a) The title compound was prepared from 2-benzyloxy-5-bromopyridine by the method of Example 22.

MS (ES) 369 (M+H)⁺. ¹H NMR (DMSO-D6) 5.4 (s, 2H), 6.9 (d, 1H), 6.95 (m, 2H), 7.35 (m, 4H), 7.4 (m, 2H), 7.6 (m, 2H), 7.8 (m, 1H), 8.3 (m, 1H), 10.96 (brs, 1H).

b) 2-Benzyloxy-5-bromopyridine

Prepared from 2,5-dibromopyridine and benzyl alcohol by the method of Example 10 (b).

MS (ES) 264 (M+H)⁺.

EXAMPLE 28

2-[(Aminocarbonyl)amino]-5-{3-[6-(tetrahydrofuran-3-yloxy)]pyridine}-3-thiophenecarboxamide a) The title compound was prepared from 2-(tetrahydrofuran-3-yloxy)-5-bromopyridine by the method of Example 22.

MS (ES) 349 (M+H)⁺. ¹H NMR (DMSO-D6) 2.0 (m, 1H), 2.2 (m, 1H), 3.8 (m, 4H), 5.5 (m; 1H), 6.8 (m, 1H), 6.95 (brs, 2H), 7.3 (m, 1H), 0.6 (m, 2H), 7.8 (m, 1H), 8.25 (s, 1H), 10.96 (brs, 1H).

b) 2-(Tetrahydrofuran-3-yloxy)-5-bromopyridine

Prepared from 2,5-dibromopyridine and 3-hydroxytetrahydrofuran by the method of Example 10 (b). ¹H NMR (DMSO-D6) 2.0 (m, 1H), 2.2 (m, 1H), 3.8 (m, 4H), 5.4 (m, 1H), 6.8 (d, 1H), 7.8 (m, 1H), 8.2 (m, 1H).

EXAMPLE 29

2-[(Aminocarbonyl)amino]-5-{3-[6-(tetrahydrofuran-3-ylmethoxy)]pyridine}-3-thiophenecarboxamide a) The title compound was prepared from 2-(tetrahydrofuran-3-ylmethoxy)-5-bromopyridine by the method of Example 22.

MS (ES) 363 (M+H)⁺. ¹H NMR (DMSO-D6) 1.6 (m, 1H), 2.0 (m, 1H), 2.6 (m, 1H), 3.5 (m, 1H), 3.6 (m, 1H), 3.8 (m, 2H), 4.2 (m, 2H), 6.8 (d, 1H), 6.95 (m, 2H), 7.3 (brs, 1H), 7.6 (m, 2H), 7.8 (m, 1H), 8.25 (m, 1H), 10.96 (brs, 1H).

b) 2-(Tetrahydrofuran-3-ylmethoxy)-5-bromopyridine

Prepared from 2,5-dibromopyridine and tetrahydrofuran-3-methanol by the method of Example 10 (b).

¹H NMR (DMSO-D6) 1.6 (m, 1H), 2.0 (m, 1H), 2.6 (m, 1H), 3.5 (m, 1H), 3.6 (m, 1H), 3.7 (m, 2H), 4.2 (m, 2H), 6.8 (d, 1H), 7.8 (m, 1H), 8.2 (s, 1H).

EXAMPLE 30

2-[(Aminocarbonyl)amino]-5-{3-[6-(cyclopropylmethoxy)]pyridine}-3-thiophenecarboxamide a) The title compound was prepared from 2-cyclopropylmethoxy-5-bromopyridine by the method of Example 22.

MS (ES) 333 (M+H)⁺. ¹H NMR (DMSO-D6) 0.25 (m, 2H), 0.35 (m, 2H), 1.25 (m, 1H), 4.05 (d, 2H), 6.85 (d, 1H), 6.9 (m, 2H), 7.25 (m, 1H), 7.6 (m, 2H), 7.75 (m, 1H), 8.25 (m, 1H), 10.93 (brs, 1H).

b) 2-(Cyclopropylmethoxy)-5-bromopyridine

Prepared from 2,5-dibromopyridine and cyclopropylmethanol by the method of Example 10 (b).

¹H NMR (DMSO-D6) 0.2 (m, 2H), 0.4 (m, 2H), 1.2 (m, 1H), 4.0 (d, 2H), 6.8 (d, 1H), 7.8 (m, 1H), 8.2 (d, 1H).

EXAMPLE 31

(S)-2-[(Aminocarbonyl)amino]-5-{3-[6-(tetrahydrofuran-3-yloxy)]pyridine}-3-thiophenecarboxamide a) The title compound was prepared from (S)-2-(tetrahydrofuran-3-yloxy)-5-bromopyridine by the method of Example 22.

MS (ES) 349 (M+H)⁺. ¹H NMR (DMSO-D6) 2.0 (m, 1H), 2.2 (m, 1H), 3.8 (m, 4H), 5.5 (m, 1H), 6.8 (d, 1H), 6.95 (m, 2H), 7.3 (brs, 1H), 7.6 (m, 2H), 7.8 (m, 1H); 8.25 (m, 1H), 10.96 (brs, 1H).

b) (S)-2-(Tetrahydrofuran-3-yloxy)-5-bromopyridine

Prepared from 2,5-dibromopyridine and S-3-hydroxytetrahydrofuran by the method of Example 10 (b).

¹H NMR (DMSO-D6) 2.0 (m, 1H), 2.2 (m, 1H), 3.8 (m, 4H), 5.4 (m, 1H), 6.8 (d, 1H), 7.8 (m, 1H), 8.2 (d, 1H).

EXAMPLE 32

2-[(Aminocarbonyl)amino]-5-{3-[6-(tetrahydropyran-4-yloxy)pyridine}-3-thiophenecarboxamide a) The title compound was prepared from 2-(tetrahydropyran-4-yloxy)-5-bromopyridine by the method of Example 22.

MS (ES) 363 (M+H)⁺. ¹H NMR (DMSO-D6) 1.6 (m, 2H), 2.0 (m, 2H), 3.5 (m, 2H), 3.8 (m, 2H), 5.2 (m, 1H), 6.8 (m, 1H), 6.95 (brs, 2H), 7.3 (m, 1H), 7.6 (m, 2H), 7.8 (m, 1H), 8.2 (d, 1H), 10.96 (brs, 1H).

b) 2-(Tetrahydropyran-4-yloxy)-5-bromopridine

Prepared from 2,5-dibromopyridine and tetrahydropyran-4-ol by the method of Example 10 (b).

MS (ES) 258 (M+H)$^+$.

EXAMPLE 33

2-[(Aminocarbonyl)amino]-5-{3-[6-(tetrahydrothiopyran-3-yloxy)]pyridine}-3-thiophenecarboxamide a) The title compound was prepared from 2-(tetrahydrothiopyran-3-yloxy)-5-bromopyridine by the method of Example 22.

MS (ES) 379 (M+H)$^+$. $^1$H NMR (DMSO-D6) 1.6 (m, 1H), 1.8 (m, 1H), 2.05 (m, 2H), 2.6 (m, 3H), 2.9 (m, 1H), 5.1 (m, 1H), 6.8 (m, 1H), 6.9 (brs, 2H), 7.3 (m, 1H), 7.6 (m, 2H), 7.8 (m, 1H), 8.25 (d, 1H), 10.96 (brs, 1H).

b) 2-(Tetrahydrothiopyran-3-yloxy)-5-bromopyridine

Prepared from 2,5-dibromopyridine and tetrahydrothiopyran-3-ol by the method of Example 10 (b).

$^1$H NMR (DMSO-D6) 1.5 (m, 1H), 1.8 (m, 2H), 2.1 (m, 2H), 2.45 (m, 1H), 2.6 (m, 1H), 2.8 (m, 1H), 5.0 (m, 1H), 6.8 (d, 1H), 7.8 (m, 1H), 8.2 (d, 1H).

EXAMPLE 34

2-[(Aminocarbonyl)amino]-5-{3-[6-(1-isopropylazetidin-3-yloxy)]pyridine)-3-thiophenecarboxamide a) The title compound was prepared from 2-(1-isopropylazetidin-3-ol)-5-bromopyridine by the method of Example 22.

MS (ES) 376 (M+H)$^+$. $^1$H NMR (DMSO-D6) 0.85 (d, 6H), 2.3 (m, 1H), 2.9 (m, 2H), 3.6 (m, 2H), 5.05 (m, 1H), 6.8 (m, 1H), 6.9 (brs, 2H), 7.3 (m, 1H), 7.6 (m, 2H), 7.8 (m, 1H), 8.2 (d, 1H), 10.96 (brs, 1H).

b) 2-(1-Isolpropylazetidin-3-ol)-5-bromopyridine

Prepared from 2,5-dibromopyridine and 1-isopropylazetidin-3-ol (J. Heterocycl. Chem. 1987, 24, 255–259) by the method of Example 10 (b).

$^1$H NMR (DMSO-D6) 0.8 (d, 6H), 2.25 (m, 1H), 2.9 (m, 2H), 3.6 (m, 2H), 5.0 (m, 1H), 6.8 (d, 1H), 7.9 (m, 1H), 8.2 (d, 1H).

EXAMPLE 35

2-[(Aminocarbonyl amino]-5-{3-[6-(benzyloxy-2-ethoxy)]pyridine}-3-thiophenecarboxamide a) The title compound was prepared from 2-(benzyloxy-2-ethoxy)-5-bromopyridine by the method of Example 22.

MS (ES) 413 (M+H)$^+$. $^1$H NMR (DMSO-D6) 3.75 (m, 2H), 4.4 (m, 2H), 4.55 (s, 2H), 6.85 (m, 1H), 6.9 (m, 2H), 7.3 (m, 1H), 7.6 (m, 2H), 7.8 (m, 1H), 8.25 (m, 1H), 10.96 (brs, 1H).

b) 2-(Benzyloxyethoxy)-5-bromopyridine

Prepared from 2,5-dibromopyridine and benzyloxy-2-ethanol by the method of Example 10 (b).

MS (ES) 308 (M+H)$^+$.

EXAMPLE 36

2-[(Aminocarbonyl)amino]-5-{3-[6-(N-methylpiperidin-3-yloxy)]pyridine)-3-thiophenecarboxamide a) The title compound was prepared from 2-(N-methylpiperidin-3-yloxy)-5-bromopyridine by the method of Example 22.

MS (ES) 376 (M+H)$^+$. $^1$H NMR (DMSO-D6) 1.4 (m, 1H), 1.5 (m, 1H), 1.7 (m, 1H), 2.0 (m, 3H), 2.15 (s, 3H), 2.8 (m, 2H), 5.0 (m, 1H), 6.8 (d, 1H), 6.95 (m, 2H), 7.3 (m, 1H) 7.6 (m, 2H), 7.8 (m, 1H), 8.25 (m, 1H), 10.96 (brs, 1H).

b) 2-(N-Methylpiperidin-3-yloxy)-5-bromopyridine

Prepared from 2,5-dibromopyridine and N-methylpiperidin-3-ol by the method of Example 10 (b).

$^1$H NMR (DMSO-D6) 1.4 (m, 1H), 1.5 (m, 1H), 1.7 (m, 1H), 1.9 (m, 1H), 2.0 (m, 3H), 2.15 (m, 3H), 2.8 (m, 1H), 4.95 (m, 1H), 6.8 (d, 1H), 7.8 (m, 1H), 8.2 (d, 1H).

EXAMPLE 37

2-[(Aminocarbonyl)amino]-5-{3-[6-(2-(1-pyrrolidin-2-one)ethoxy)]pyridine}-3-thiophenecarboxamide a) The title compound was prepared from 2-(2-(1-pyrrolidin-2-one)ethoxy)-5-bromopyridine by the method of Example 22.

MS (ES) 390 (M+H)$^+$. $^1$H NMR (DMSO-D6) 0.8 (m, 2H), 1.9 (m, 2H), 2.2 (m, 2H), 3.55 (m, 2H), 4.4 (m, 2H), 6.8 (m, 1H), 6.99 (m, 2H), 7.3 (m, 1H), 7.6 (m, 2H), 7.8 (m, 1H), 8.3 (m, 1H), 10.96 (m, 1H).

b) 2-(2-(1-Pyrrolidin-2-one)ethoxy)-5-bromopyridine

Prepared by the method of Example 10 (b) using 2,5-dibromopyridine and 1-(2-hydroxyethyl)-pyrrolidin-2-one.

MS (ES) 285(M+H)$^+$. $^1$H NMR (DMSO-D6) 2.0 (q, 2H), 2.37 (t, 2H), 3.5 (t, 2H), 3.67 (t, 2H), 4.43 (t, 2H), 6.65 (d, 1H), 7.64 (q, 1H), 8.16 (d, 1H).

EXAMPLE 38

2-[(Aminocarbonyl)amino]-5-3-(6-(morpholin-4-yl))pyridine]-3-thiophenecarboxamide a) A mixture of 5-iodo-2-morpholinopyridine (1.26 g), bis(pinacolato)diboron (1.16 g), potassium acetate (1.28 g) and PdCl$_2$(dppf) (40 mg) in dimethylacetamide (15 ml) was flushed with argon was heated at 80° C. for 4 h, and then allowed to cool. 2-[(Aminocarbonyl)amino]-5-bromo-3-thiophenecarboxamide (0.287 g) was added, followed by a further portion of PdCl$_2$(dppf) and 2M aqueous sodium hydrogen carbonate (8 ml). The mixture was heated at 90 C for 18 h, then allowed to cool to room temperature and stirred for a further 48 h. The solvent was removed in vacuo and the residue taken up in 2M aqueous sodium hydroxide (30 ml) and dichloromethane (30 ml). The layers were separated and the organic phase was washed with a further portion of 2M aqueous sodium hydroxide (20 ml). The combined aqueous layers were then washed with further dichloromethane (30 ml). The aqueous phase was filtered to remove a small amount of insoluble material and the filtrate then neutralised with 6M hydrochloric acid. The precipitated product was then collected by filtration and washed with water. The crude product was triturated with a mixture of methanol and ether, filtered and dried to give the product as a brown solid (112 mg).

MS (ES) 348 (M+H)+. 1H NMR (DMSO-D6) 400 MHz 3.40–3.60 (m, 4H), 3.60–3.80 (m, 4H), 6.54 (bs, 2H), 6.85 (d, 1H), 7.09 (bs, 2H), 7.46 (s, 1H), 7.67 (dd, 1H), 8.32 (d, 1H), 10.86 (s, 1H).

b) 4-(5-Iodo-pyridin-2-yl)morpholine

Prepared from 2-chloro-5-iodopyridine and morpholine by the method of Example 9 (d).

MS (ES) 291 (M+H)+. 1H NMR (DMSO-D6) 3.34–3.45 (m, 4H), 3.61–3.72 (m, 4H), 6.72 (d, 1H), 7.77 (dd, 1H), 8.22 (d, 1H).

EXAMPLE 39

2-[(Aminocarbonyl amino]-5-[3-[6-(4-methylpiperazin-1-yl)]pyridine)-3-thiophenecarboxamide a) The title compound was prepared from 1-(5-bromopyridin-2-yl)-4-methylpiperazine in a similar manner to Example 38.

MS (ES) 361 (M+H)+. 1H NMR (DMSO-D6) 400 MHz 2.10–2.40 (s, 3H), 2.40–2.65 (m, 4H), 3.44–3.80 (m, 4H), 6.56 (bs, 2H), 6.84 (d, 1H), 7.12 (bs, 2H), 7.47 (s, 1H), 7.66 (d, 1H), 8.30 (s, 1H), 10.85 (s, 1H).

b) 1-(5-Bromo-pyridin-2-yl)-4-methylpiperazine

Prepared from 2,5-dibromopyridine and 4-methylpiperazine in a similar manner to Example 9(d).

MS (ES) 256 (M+H)+. 1H NMR (DMSO-D6) 2.18 (s, 3H), 2.30–2.40 (m, 4H), 3.36–3.50 (m, 4H), 6.79 (d, 1H), 7.64 (dd, 1H), 8.13 (d, 1H).

EXAMPLE 40

2-[(Aminocarbonyl)amino]-5-(4-[1,3,4-oxadiazol-2-yl]-2-phenyl)-3-thiophenecarboxamide A solution of 2-[(aminocarbonyl)amino]-5-bromo-3-thiophenecarboxamide (0.26 g), sodium carbonate (0.23 g), and 4-[1,3,4-oxadiazol-2-yl]phenyl boronic acid (0.38 g) in 1,2-dimethoxyethane (10 ml) and water (1 ml) was purged with argon for 10 minutes. Tetrakis(triphenylphosphine)palladium (0.2 g) was then added and the mixture refluxed with stirring for 8 h. After cooling, the mixture was filtered and the resulting solid was washed with 2N sodium hydroxide solution, then with water, and finally methanol, to give the required product (0.1 g).

MS (CI) 330 (M+H)+. 1H NMR (DMSO-D6) 7.0 (m, 2H), 7.35 (m, 1H), 7.7 (m, 3H), 7.9 (s, 1H), 8.0 (m, 2H), 9.3 (s, 1H), 11.04 (m, 1H).

4-[1,3,4-Oxadiazol-2-yl]phenyl boronic acid was prepared as described in Ger. Offen. DE 19857765.

EXAMPLE 41

2-[(Aminocarbonyl)amino]-5-(4-cyclopropylmethoxyphenyl)-3-thiophenecarboxamide

The title compound was prepared in a similar manner to Example 40 but using 4-(cyclopropylmethoxy)-phenyl boronic acid.

MS (S) 332 (M+H)+. 1H NMR (DMSO-D6) 0.3 (m, 2H), 0.6 (m, 2H), 1.25 (m, 1H), 3.9 (d, 2H), 6.9 (m, 2H), 6.95 (d, 1H), 7.25 (m, 1H), 7.4 (d, 1H), 7.65 (m, 1H), 10.94 (brs, 1H).

EXAMPLE 42

2-[(Aminocarbonyl)amino]-5-[3-(1,3-thiazol-4-ylmethoxy)phenyl]thiophene-3-carboxamide a) The title compound was prepared from 4-[(3-bromophenoxy)methyl]-1,3-thiazole in a similar manner to Example 9 (e) except that the crude solid obtained was purified by preparative HPLC to give a brown solid (15 mg).

LCMS (ES) 375 (M+H)+. 1HNMR (DMSO-D6), 5.27 (s, 2H), 6.92 (m, 3H), 7.10 (m, 1H), 7.20 (s, 1H), 7.30 (m, 2H), 7.64 (bs, 1H), 7.80 (m, 2H), 9.14 (s, 1H), 11.00 (s, 1H).

b) 4-[(3-Bromophenoxy)methyl]-1,3-thiazole 4-(Chloromethyl)thiazole hydrochloride (3.0 g), 3-bromophenol (2.77 g) and potassium carbonate (7.30 g) were heated in dimethylformamide at 60° C., with stirring, for 18 h. The mixture was partitioned between diethyl ether (50 ml) and water (50 ml) and the aqueous phase was extracted further with ether (50 ml). The combined organics were washed with 2M aqueous sodium hydroxide (100 ml) and water (100 ml), dried (magnesium sulphate) and concentrated in vacuo to give the product as a yellow crystalline solid (3.82 g).

MS (ES) 270/272 (M+H)+. 1H NMR (DMSO-D6) 5.21 (s, 2H), 7.02 (m, 1H), 7.12 (m, 1H), 7.22 (m, 2H), 7.78 (s, 1H), 9.10 (s, 1H).

EXAMPLE 43

2-[(Aminocarbonyl)amino]-5-[4-(morpholin-4-ylmethyl)phenyl]thiophene-3-carboxamide a) The title compound was prepared from N-(4-bromobenzyl)morpholine in a similar manner to Example 9 (e) except that the compound was isolated by neutralisation of the basic aqueous phase followed by filtration, washing with water and drying of resulting precipitate to give a cream solid (97 mg).

MS (ES) 361 (M+H)+. 1H NMR (DMSO-D6) 2.32 (t, 4H) 3.40 (s, 2H), 3.55 (t, 4H), 6.90 (bs, 2H), 7.25 (m, 3H), 7.45 (d, 2H), 7.62 (bs, 1H), 7.65 (s, 1H), 10.97 (s, 1H).

b) N-(4-Bromobenzyl)morpholine

4-Bromobenzyl bromide (2.0 g) and morpholine (1.39 ml) were stirred in dimethylformamide (25 ml) for 18 h. The mixture was partitioned between diethyl ether (50 ml) and water (80 ml). The aqueous phase was extracted further with ether (50 ml) and the combined organics were washed with water (80 ml), dried (magnesium sulphate) and evaporated. The residue was purified by column chromatography, eluting with a gradient of ethyl acetate/iso-hexane; 0/100 to 50/50, to give the product as a white crystalline solid (1.44 g).

MS (ES) 256/258 (M+H)+. 1H NMR (DMSO-D6) 2.30 (t, 4H), 3.40 (s, 2H), 3.55 (t, 4H), 7.22 (d, 2H), 7.48 (d, 2H).

EXAMPLE 44

2-[(Aminocarbonyl)amino]-5-(5-[2-(N-morpholinyl)]pyrimidinyl)-3-thiophenecarboxamide a) The title compound was prepared from 2-(N-morpholino)-5-bromopyrimidine by the method of Example 9 (e).

MS (ES) 349 (M+H)+. 1H NMR (DMSO-D6) 3.7 (m, 8H), 6.95 (br, 2H), 7.3 (br, 1H), 7.55 (s, 1H), 7.6 (br, 1H), 8.5 (s, 2H), 10.94 (brs, 1H).

b) 2-(N-Morpholino)-5-bromopyrimidine

A solution of 2-chloro-5-bromopyrimidine (1.0 g) and morpholine (1.12 ml) in dimethoxyacetamide (8 ml) was heated and stirred at 150° C. for 6 h. After cooling, the reaction mixture was added to water and the solid was filtered off and washed with water.

The solid was dissolved in ethyl acetate, washed with brine and the solvent phase was dried (magnesium sulphate). On evaporation a solid was obtained (1.2 g).

MS (ES) 244/246 (M+H)$^+$.

EXAMPLE 45

2-[(Aminocarbonyl)amino]-5-(5-[2-(N-piperidinyl)]pyrimidinyl)-3-thiophenecarboxamide a) The title compound was prepared from 2-(N-piperidinyl)-5-bromopyrimidine by the method of Example 9 (e).

MS (ES) 347 (M+H)$^+$. $^1$H NMR (DMSO-D6) 1.5 (m, 4H), 1.6 (m, 2H), 3.7 (m, 4H), 7.3 (m, 1H), 7.55 (s, 1H), 7.6 (m, 3H), 8.45 (s, 2H), 10.95 (brs, 1H).

b) 2-(N-Piperidinyl)-5-bromopyrimidine

Prepared from 2-chloro-5-bromopyrimidine and piperidine by the method of Example 44 (b).

MS (ES) 242/244 (M+H)$^+$.

EXAMPLE 46

2-[(Aminocarbonyl)amino]-5-(5-[2-(N-pyrrolidinyl]pyrimidinyl)-3-thiophenecarboxamide a) The title compound was prepared from 2-(N-pyrrolidinyl)-5-bromopyrimidine by the method of Example 9 (e).

MS (ES) 333 (M+H)$^+$. $^1$H NMR (DMSO-D6) 1.9 (m, 4H), 3.5 (m, 4H), 6.9 (m, 2H), 7.3 (m, 1H), 7.45 (s, 1H), 7.6 (m, 1H), 8.45 (s, 2H), 10.94 (brs, 1H).

b) 2-(N-Pyrrolidinyl)-5-bromopyrimidine

Prepared from 2-chloro-5-bromopyrimidine and pyrrolidine by the method of Example 44 (b).

MS (ES) 228/230 (M+H)$^+$.

EXAMPLE 47

2-[(Aminocarbonyl)amino]-5-(5-[2-{4-(t-butyloxycarbonyl)piperazin-1-yl}]pyrimidinyl)-3-thiophenecarboxamide a) The title compound was prepared from 5-bromo-2-[4-(t-butyloxycarbonyl)piperazin-1-yl]pyrimidine by the method of Example 9 (e).

MS (ES) 448 (MH)$^+$. $^1$H NMR (DMSO-D6) 300 MHz δ 1.41 (s, 9H), 3.40 (t, 4H), 3.73 (t, 4H), 6.93 (s, 2H), 7.29 (s, 1H), 7.54 (s, 1H), 7.59 (s, 1H), 8.50 (s, 2H), 10.95 (s, 1H).

b) 5-Bromo-2-[4-(t-butyloxycarbonyl)piperazin-1-yl]pyrimidine

Prepared from 1-t-butoxycarbonylpiperazine by the method of Example 44 (b).

MS (ES) 343,345 (MH)$^+$. $^1$H NMR (DMSO-D6) 300 MHz δ 1.40 (s, 9H), 3.37 (m, 4H), 3.67 (m, 4H), 8.45 (s, 2H).

EXAMPLE 48

2-[(Aminocarbonyl)amino]-5-(-5-[2-{4H-piperazin-1-yl}]pyrimidinyl)-3-thiophenecarboxamide A mixture of 2-[(aminocarbonyl)amino]-5-(5-[2-{4-(t-butyloxycarbonyl)piperazin-1-yl}]pyrimidinyl)-3-thiophenecarboxamide (120 mg), triethylsilane (1 ml) and dichloromethane (2 ml) was treated with trifluoroacetic acid (2 ml) and stirred at ambient temperature for 1 h. After evaporation to dryness, trituration of the resultant oil with ether gave a solid. This was dissolved in water, filtered and the pH adjusted to 7 to give the product (56 mg) as a yellow solid.

MS (ES) 348 (MH)$^+$. $^1$H NMR (DMSO-D6)300 MHz δ 2.72 (t, 4H), 3.66 (t, 4H), 6.92 (s, 2H), 7.27 (s, 1H), 7.51 (s, 1H), 7.58 (s, 1H), 8.47 (s, 2H), 10.94 (s, 1H).

EXAMPLE 49

2-[(Aminocarbonyl)amino]-5-(5-[2-(4-methylpiperazin-1-yl}]pyrimidinyl)-3-thiophenecarboxamide a) The title compound was prepared from 5-bromo-2-[4-methylpiperazin-1-yl]pyrimidine by the method of Example 10 (a).

MS (ES) 362 (MH)$^+$. $^1$H NMR (DMSO-D6) 300 MHz δ 2.21 (s, 3H), 2.38 (t, 4H), 3.72 (t, 4H), 6.92 (s, 2H), 7.28 (s, 1H), 7.54 (s, 1H), 7.59 (s, 1H), 8.48 (s, 2H), 10.95 (s, 1H).

b) 5-Bromo-2-[4-methylpiperazin-1-yl]pyrimidine

Prepared from 1-methylpiperazine by the method of Example 44 (b).

MS (ES) 257, 259(MH)$^+$. $^1$H NMR (DMSO-D6) 300 MHz δ 2.18 (3H, s), 2.32 (4H, t), 3.67 (4H, t), 8.42 (2H, s).

EXAMPLE 50

2-[(Aminocarbonyl)amino]-5-(5-[2-(3-dimethylaminopyrrolidin-1-yl)]pyrimidinyl)-3-thiophenecarboxamide a) The title compound was prepared from 5-bromo-2-[3-dimethylaminopyrrolidin-1-yl]pyrimidine by the method of Example 10 (a).

MS (ES) 376(MH)$^+$. $^1$H NMR (DMSO-D6) 300 MHz δ 2.15 (1H, m), 2.33 (1H, m), 2.67 (6H, s), 3.47 (1H, m), 3.60 (1H, m), 3.76 (2H, m), 3.94 (1H, m), 6.93 (2H, s), 7.29 (1H, s), 7.56 (1H, s), 7.62 (1H, s), 8.51 (2H, s), 10.95 (1H, s).

b) 5-Bromo-2-[3-dimethylaminopyrrolidin-1-yl]pyrimidine

Prepared from 3-dimethylaminopyrrolidine by the method of Example 44 (b).

MS (ES) 271,273 (MH)$^+$. $^1$H NMR (DMSO-D6) 300 MHz δ 1.77 (1H, m), 2.10 (1H, m), 2.16 (6H, s), 2.74 (1H, m), 3.13 (1H, m), 3.36 (1H, m) 3.62 (1H, m), 3.70 (1H, m), 8.40 (2H, s).

EXAMPLE 51

2-[(Aminocarbonyl)amino]-5-(5-{2-2(S)-aminocarbonylpyrrolidin-1-yl}]pyrimidinyl)-3-thiophenecarboxamide a) The title compound was prepared from 5-bromo-2-{2-(S)aminocarbonylpyrrolidin-1-yl}pyrimidine by the method of Example 10 (a).

MS (ES) 376 (MH)$^+$. $^1$H NMR (DMSO-D6) 300 MHz δ 1.93 (3H, m), 2.21 (1H, m), 3.54 (1H, m), 3.67 (1H, m), 4.37

(1H, d), 6.84 (1H, s), 6.91 (2H, s), 7.29 (1H, s), 7.32 (1H, s), 7.52 (1H, s), 7.61 (1H, s), 8.45 (2H, s), 10.94 (1H, s).

b) 5-Bromo-2-{2-(S)aminocarbonylpyrrolidin-1-yl}pyrimidine

Prepared from L-proline amide by the method of Example 44 (b).

MS (ES) 271,273 (MH)$^+$. $^1$H NMR (DMSO-D6) 300 MHz δ 1.91 (3H, m), 2.18 (1H, m), 3.48 (1H, m), 3.59 (1H, m), 4.30 (1H, m), 6.84 (1H, s), 7.30 (1H, s), 8.41 (2H, s).

EXAMPLE 52

2-[(Aminocarbonyl)amino]-5-(5-[2-(4-acetylpiperazin-1-yl}]pyrimidinyl)-3-thiophenecarboxamide a) The title compound was prepared from 5-bromo-2-{4-acetylpiperazin-1-yl}pyrimidine by the method of Example 9 (e).

MS (ES) 390 (MH)$^+$. $^1$H NMR (DMSO-D6) 300 MHz δ 2.03 (3H, s), 3.51 (4H, t), 3.75 (4H, m), 6.92 (2H, s), 7.28 (1H, s), 7.50 (1H, s), 7.54 (1H, s), 8.51 (2H, s), 10.95 (1H, s).

b) 5-Bromo-2-{4-acetylpiperazin-1-yl}pyrimidine

Prepared from 1-acetylpiperazine by the method of Example 44 (b).

MS (ES) 285,287 (MH)$^+$. $^1$H NMR (DMSO-D6) 300 MHz δ 2.02 (3H, s), 3.50 (4H, dd), 3.69 (4H, m), 8.46 (2H, s).

EXAMPLE 53

2-[(Aminocarbonyl)amino]-5-(5-{2-[4,4-difluoropiperidin-1-yl]}pyrimidinyl)-3-thiophenecarboxamide a) The title compound was prepared from 5-bromo-2-[4,4-difluoropiperidin-1-yl]pyrimidine by the method of Example 9 (e).

MS (ES) 383 (m)$^+$. $^1$H NMR (DMSO-D6) 300 MHz δ 1.97 (4H, m), 3.85 (4H, t), 7.22 (1H, s), 8.41 (2H, s).

b) 5-Bromo-2-[4,4-difluoropiperidin-1-yl]pyrimidine

Prepared from 4,4-difluoropiperidine by the method of Example 44 (b).

MS (ES) 278,280 (MH)$^+$. $^1$H NMR (DMSO-D6) 300 MHz δ 1.97 (4H, m), 3.84 (4H, t), 8.47 (2H, s).

EXAMPLE 54

2-[(Aminocarbonyl)amino]-5-(5-{2-[3,3-difluoropyrrolidin-1-yl]}pyrimidinyl)-3-thiophenecarboxamide a) The title compound was prepared from 5-bromo-2-[3,3-difluoropyrrolidin-1-yl]pyrimidine by the method of Example 9 (e).

MS (ES) 369 (MH)$^+$. $^1$H NMR (DMSO-D6) 300 MHz δ 2.56 (2H, m), 3.74 (2H, t), 3.91 (2H, t), 6.94 (2H, s), 7.29 (1H, s), 7.54 (1H, s), 7.59 (1H, s), 8.53 (2H, s), 10.95 (1H, s).

b) 5-Bromo-2-[3,3-difluoropyrrolidin-1-yl]pyrimidine

Prepared from 3,3-difluoropyrrolidine by the method of Example 44 (b).

MS (ES) 264, 266 (MH)$^+$. $^1$H NMR (DMSO-D6) δ 2.52 (2H, m), 3.68 (2H, t), 3.85 (2H, t), 8.50 (2H, s).

EXAMPLE 55

2-[(Aminocarbonyl)amino]-5-{2-(5-N-morpholinomethyl)thienyl}-3-thiophenecarboxamide a) The title compound was prepared from 4-(5-bromothien-2-ylmethyl)morpholine in a similar manner to Example 9 (e) except that further purification was achieved using column chromatography eluting with methanol in dichloromethane mixtures.

MS (ES) 365 (M−H)$^-$. $^1$H NMR (DMSO-D6) 2.45 (m, 4H), 3.6 (m, 4H), 3.7 (s, 2H), 6.85 (d, 1H), 6.9 (d, 1H), 6.95 (bs, 2H), 7.45 (s, 1H), 7.7 (bs, 1H), 11.0 (s, 1H).

b) 4-(5-Bromothien-2-ylmethyl)morpholine

Morpholine (0.96 g) was added portionwise to a solution of 2-bromothiophene carboxaldehyde (1.195 g) in tetrahydrofuran (50 ml). After stirring at room temperature for 5 minutes, sodium triacetoxyborohydride (3.18 g) was added and the mixture stirred at room temperature for a further 3 h. The mixture was added to saturated aqueous sodium bicarbonate (100 ml) and extracted twice with ethyl acetate. The combined extracts were evapourated to dryness. The product was purified by column chromatography eluting with ethyl acetate in hexane mixtures to give a yellow oil (2.414 g).

MS (ES) 263 (M+H)$^+$. $^1$H NMR (DMSO-D6) 2.4 (t, 4H) 3.6 (t, 4H) 3.65 (s, 2H), 6.8 (d, 1H), 7.05 (d, 1H).

EXAMPLE 56

2-[(Aminocarbonyl)amino]-5-{2-benzyloxyphenyl}-3-thiophenecarboxamide a) The title compound was prepared from 2-bromophenylbenzyl ether in a similar manner to Example 9 (e).

MS (ES) 366 (M−H)$^-$. $^1$H NMR (DMSO-D6) 5.3 (s, 2H), 6.85 (bs, 2H), 7.35–7.2 (m, 6H), 7.7–7.4 (m, 5H), 7.75 (s, 1H), 11.0 (s, 1H).

b) 2-Bromophenylbenzyl ether

Potassium carbonate (9.12 g) was suspended in dimethylformamide (25 ml) and 2-bromophenol (3.46 g) was added portionwise. Benzyl bromide (3.76 g) was added and the mixture heated to 60° C. for 4 h. After cooling the mixture was added to water (250 ml) and extracted three times with diethyl ether. The organic layer was separated and washed with 2M sodium hydroxide solution (100 ml) before drying over sodium sulphate. After filtration, evaporation yielded (5.13 g) as a colourless oil.

MS (ES) 262 (M−H)$^-$. $^1$H NMR (DMSO-D6) 5.2 (s, 2H), 6.9 (td, 1H), 7.2 (dd, 1H), 7.32 (m, 1H), 7.35 (m, 1H), 7.42 (m, 2H), 7.49 (m, 2H), 7.6 (dd, 1H).

EXAMPLE 57

2-[(Aminocarbonyl)amino]-5-{2-(4-fluorophenylmethoxy)phenyl}-3-thiophenecarboxamide a) The title compound was prepared from 2-(4-fluorophenylmethoxy)bromobenzene in a similar manner to Example 9 (e).

MS (ES) 384 (M−H)$^-$. $^1$H NMR (DMSO-D6) 5.25 (s, 2H), 6.85 (bs, 2H), 7.05 (t, 1H), 7.25–7.2 (m, 4H), 7.7 (bs, 1H), 7.75–7.6 (m, 4H), 7.8 (s, 1H), 10.9 (s, 1H).

b) 2-(4-Fluorophenylmethoxy)bromobenzene

Prepared from 4-fluorobenzylbromide in a similar manner to Example 56 (b).

MS (ES) 280 (M–H)⁻. ¹H NMR (DMSO-D6) 5.15 (s, 2H), 6.9 (td, 1H), 7.23 (m, 2H), 7.25 (m, 1H), 7.35 (td, 1H), 7.54 (m, 1H), 7.6 (dd, 1H).

EXAMPLE 58

2-[(Aminocarbonyl)amino]-5-{2-(2-[4-fluorophenyl]ethoxy)phenyl}-3-thiophenecarboxamide a) The title compound was prepared from 2-(2-[4-fluorophenyl]ethoxy)bromobenzene in a similar manner to Example 9 (e).

MS (ES) 398 (M–H)⁻. ¹H NMR (DMSO-D6) 3.3 (t, 2H), 4.25 (t, 2H), 6.9 (bs, 2H), 7.0 (td, 1H), 7.1 (m, 3H), 7.2 (m, 2H), 7.5 (m, 2H), 7.7 (m, 2H), 7.75 (s, 1H), 10.9 (s, 1H).

b) 2-(2-[4-Fluorophenyl]ethoxy)bromobenzene

2-Bromophenol (3.46 g) was mixed with tetrahydrofuran (60 ml) and triphenylphosphine (6.3 g) was added along with 4-fluorophenethyl alcohol (4.2 g). The mixture was cooled in an ice bath before dropwise addition of diisopropyl azodicarboxylate (4.85 g). The mixture was allowed to warm to room temperature over 18 h. The mixture was evaporated and diethyl ether (100 ml) was added. Stirring was continued for 3 h, the mixture was filtered and the filtrate was evaporated. The product was purified by column chromatography eluting with ethyl acetate/hexane mixtures to give a yellow oil (4.47 g).

MS (ES) 294 (M–H)⁻. ¹H NMR (DMSO-D6) 3.05 (t, 2H), 4.2 (t, 2H), 6.9 (td, 1H), 7.1 (m, 3H), 7.3 (td, 1H), 7.4 (m, 2H), 7.55 (dd, 1H).

EXAMPLE 59

2-[(Aminocarbonyl)amino]-5-{2-(2-[4-chlorophenyl]ethoxy)phenyl}-3-thiophenecarboxamide a) The title compound was prepared from 2-(2-[4-chlorophenyl]ethoxy)bromobenzene in a similar manner to Example 9 (e).

MS (ES) 414 (M–H)⁻. ¹H NMR (DMSO-D6) 3.2 (t, 2H), 4.25 (t, 2H), 6.85 (bs, 2H), 7.0 (td, 1H), 7.1 (dd, 1H), 7.2 (m, 4H), 7.5 (d, 2H), 7.65 (m, 2H), 7.75 (s, 1H), 11.0 (s, 1H).

b) 2-(2-[4-Chlorophenyl]ethoxy)bromobenzene

Prepared from 4-chlorophenethyl alcohol in a similar manner to Example 58 (b).

MS (ES) 310 (M–H)⁻. ¹H NMR (DMSO-D6) 3.05 (t, 2H), 4.3 (t, 2H), 6.85 (td, 1H), 7.45 (m, 5H), 7.55 (dd, 1H).

EXAMPLE 60

2-[(Aminocarbonyl)amino]-5-{2-(2-phenylethoxy)phenyl}-3-thiophenecarboxamide a) The title compound was prepared from 2-(2-phenylethoxy)bromobenzene in a similar manner to Example 9 (e).

MS (ES) 380 (M–H)⁻. ¹H NMR (DMSO-D6) 3.2 (t, 2H), 4.3 (t, 2H), 6.8 (sb, 2H), 7.0 (td, 1H), 7.1 (dd, 1H), 7.25 (m, 2H), 7.45–7.25 (m, 5H), 7.7 (m, 2H), 7.75 (s, 1H), 11.0 (s, 1H).

b) 2-(2-Phenylethoxy)bromobenzene

Prepared from phenethyl alcohol in a similar manner to Example 58 (b).

MS (ES) 276 (M–H)⁻. ¹H NMR (DMSO-D6) 3.1 (t, 2H), 4.2 (t, 2H), 6.9 (td, 1H), 7.15 (dd, 1H), 7.5–7.2 (m, 6H), 7.55 (dd, 1H).

EXAMPLE 61

2-[(Aminocarbonyl)amino]-5-[4-chlorophenylmethoxy)phenyl]-3-thiophenecarboxamide a) The title compound was prepared from 2-(4-chlorophenylmethoxy)bromobenzene in a similar manner to Example 9 (e).

MS (ES) 400 (M–H)⁻. ¹HNMR (DMSO-D6) 5.25 (s, 2H), 6.9 (bs, 2H), 7.0 (m, 1H), 7.1 (m, 1H), 7.2 (m, 2H), 7.4 (d, 2H), 7.6 (d, 2H), 7.65 (m, 2H), 7.8 (s, 1H), 11.0 (s, 1H).

b) 2-(4-Chlorophenylmethoxy)bromobenzene

Prepared from 4-chlorobenzyl bromide in a similar manner to Example 56 (b).

MS (ES) 296 (M–H)⁻. ¹H NMR (DMSO-D6) 5.2 (s, 2H), 7.2 (dd, 1H), 7.35 (td, 1H), 7.5 (m, 4H), 7.6 (dd, 1H).

EXAMPLE 62

2-[(Aminocarbonyl)amino]-5-{2-[2-(N-morpholinyl)]ethylthio)phenyl}-3-thiophenecarboxamide a) The title compound was prepared from 4-[2-(2-bromophenylthio)ethyl]morpholine in a similar manner to Example 9 (e).

MS (ES) 407 (M+H)⁺. ¹H NMR (DMSO-D6) 1.8 (m, 4H), 2.5 (partially obscured by DMSO), 3.0 (t, 2H), 3.45 (m, 4H), 6.9 (bs, 2H), 7.2 (m, 2H), 7.35 (m, 2H), 7.4 (m, 2H), 7.6 (bs, 1H), 11.0 (s, 1H).

b) 4-[2-(2-Bromophenylthio)ethyl]morpholine

Potassium carbonate (10.95 g) and 2-chloroethylmorpholine hydrochloride (5.9 g) were mixed with dimethylformamide (50 ml) and 2-bromothiophenol was added before the mixture was heated to 100° C. for 3 days. The mixture was allowed to cool before water (500 ml) was added. The product was extracted into diethyl ether (×3). The combined extracts were dried over sodium sulphate and filtered before evaporation. The product was purified by column chromatography eluting with ethyl acetate/hexane mixtures to give a red/brown oil (6.024 g).

MS (ES) 303 (M+H)⁺. ¹H NMR (DMSO-D6) 2.5 (m, 4H), 2.7 (t 2H), 3.05 (t, 2H), 3.75 (m, 4H), 7.05 (m, 1H), 7.25–7.2 (m, 2H), 7.7 (dd, 1H).

EXAMPLE 63

2-[(Aminocarbonyl)amino]-5-{2-[2-(N-pyrrolidinyl)]ethylthio)phenyl}-3-thiophenecarboxamide a) The title compound was prepared from 1-[2-(2-bromophenylthio)ethyl]pyrrolidine in a similar manner to Example 9 (e).

MS (ES) 391 (M+H)⁺. ¹H NMR (DMSO-D6) 1.6 (m, 4H), 2.4 (m, 4H), 2.6 (t, 2H), 3.0 (t, 2H), 6.9 (bs, 2H), 7.2 (m, 2H), 7.4–7.3 (m, 4H), 7.6 (bs, 1H), 11.0 (s, 1H).

b) 1-[2-(2-Bromophenylthio)ethyl]pyrrolidine
Prepared using 2-chloroethylpyrrolidine hydrochloride (5.36 g) in a similar manner to Example 62 (b).
MS (ES) 287 (M+H)$^+$. $^1$H NMR (DMSO-D6) 1.6 (m, 4H), 2.5 (partially obscured by DMSO), 2.7 (t, 2H), 3.05 (t, 2H), 7.05 (m, 1H), 7.35 (m, 2H), 7.6 (dd, 1H).

EXAMPLE 64

2-[(Aminocarbonyl)amino]-5-{2-[2-(N-piperidinyl)]ethylthio)phenyl}-3-thiophenecarboxamide a) The title compound was prepared from 1-[2-(2-bromophenylthio)ethyl]piperidine in a similar manner to Example 9 (e).
MS (ES) 403 (M+H)$^+$. $^1$H NMR (DMSO-D6) 1.3 (m, 2H), 1.4 (m, 4H), 2.3 (m, 4H), 2.5 (partially obscured by DMSO), 3.0 (t, 2H), 7.0 (bs, 2H), 7.1 (bs, 1H), 7.5–7.2 (m, 4H), 7.5 (s, 1H), 7.7 (bs, 1H), 11.0 (s, 1H).
b) 1-[2-(2-Bromophenylthio)ethyl]piperidine
Prepared using 2-chloroethylpiperidine hydrochloride (5.36 g) in a similar manner to Example 62 (b).
MS (ES) 287 (M+H)$^+$. $^1$H NMR (DMSO-D6) 1.4 (m, 2H), 1.5 (m, 4H), 2.4 (m, 4H), 2.6 (t, 2H), 3.1 (t, 2H), 7.1 (m, 1H), 7.4 (m, 2H), 7.6 (dd, 1H).

EXAMPLE 65

2-[(Aminocarbonyl)amino]-5-[4-(pyrrolidinyl)phenyl]-3-thiophenecarboxamide a) The title compound was prepared from 1-(4-iodophenyl)pyrrolidine in a similar manner to Example 10 (a).
MS (ES) 330 (M)$^+$. $^1$H NMR (DMSO-D6, 300 MHz) 1.90–1.98 (m, 4H), 3.18–3.25 (m, 4H), 6.55 (d, 2H), 6.83 (bs, 2H), 7.20 (bs, 1H), 7.35 (d, 2H), 7.40 (s, 1H), 7.60 (bs, 1H), 10.89 (s, 1H).
b) 1-(4-Iodophenyl) pyrrolidine
Iodine (6.09 g) was added slowly to a stirred solution of phenylpyrrolidine (3.21 g) and sodium bicarbonate (2.75 g) in water (30 ml). The reaction was stirred for 1 h and then left to stand overnight. The solid was isolated by filtration, dissolved in ethanol (506 ml) and discoloured with aqueous sodium thiosulfate. The product was then isolated by filtration and recrystalised from ethanol to give the desired product as a brown/red powder (1.17 g).
MS (EI) 273 (M)$^+$. $^1$H NMR (DMSO-D6) 1.94 (t, 2H), 3.18 (t, 2H), 6.36 (d, 2H), 7.38 (d, 2H).

EXAMPLE 66

2-[(Aminocarbonyl)amino]-5-[4-(piperidinyl)phenyl-3-thiophenecarboxamide a) The title compound was prepared from 1-(4-iodophenyl)piperidine in a similar manner to Example 10 (a).
MS (ES) 345 (M+H)$^+$. $^1$H NMR (DMSO-D6) 300 MHz 1.50–1.65 (m, 6H), 3.15–3.25 (m, 4H), 6.80–6.95 (m, 3H), 7.20 (bs, 1H), 7.35 (d, 2H), 7.50 (s, 1H), 7.65 (d, 2H), 10.91 (s, 1H).
b) 1-(Iodophenyl)piperidine
Prepared from phenylpiperidine in a similar manner to Example 65 (b).
MS (ES) 288 (M+H)$^+$. $^1$H NMR (DMSO-D6) 300 MHz 1.45–1.65 (m, 6H), 3.05–3.15 (m, 4H), 6.75 (d, 2H), 7.45 (d, 2H).

EXAMPLE 67

2-[(Aminocarbonyl)amino]-5-[4-(N-imidazolyl)phenyl]-3-thiophenecarboxamide a) The title compound was prepared from N-(bromophenyl)-1H-imidazole in a similar manner to Example 10 (a).
MS (ES) 328 (M+H)$^+$. $^1$HNMR (DMSO-D6) 300 MHz 6.95 (bs, 1H), 7.10 (s, 1H), 7.30 bs, 1H), 7.58–7.82 (m, 8H), 8.24 (s, 1 h), 11.00 (s, 1H).

EXAMPLE 68

2-[(Aminocarbonyl)amino]-5-[6-{(1-methylpyrrolidine-2-on-4-yl)methoxy}pyridin-3-yl]-3-thiophenecarboxamide a) The title compound was prepared from 5-bromo-2-{(1-methylpyrrolidine-2-on-4-yl)methoxy}pyridine in a similar manner to Example 9 (e).
MS (ES) 390 (M+H)$^+$, 388 (M−H)$^-$. $^1$H NMR (DMSO-D6) 11.10 (s, 1H), 8.30 (d, 1H), 7.85 (m, 1H), 7.60 (bs, 1H), 7.40 (s, 1H), 7.30 (bs, 1H), 6.90 (d, 1H), 6.80–7.20 (bs, 2H), 4.25–4.45 (m, 2H), 3.20–3.60 (m, 2H), 2.10–2.60 (m, 6H).
b) 5-Bromo-2-{(1-methylpyrrolidine-2-on-4-yl)methoxy}pyridine
Prepared from 2,5-dibromopyridine and 4-hydroxymethyl-1-methylpyrrolidine-2-one by the method of Example 10 (b).
MS (ES) 285.1 (M+H)$^+$. $^1$H NMR (CDCl$_3$) 8.16 (d, 1H), 7.64 (dd, 1H), 6.65 (d, 1H), 4.20–4.35 (m, 2H), 3.52 (dd, 1H), 3.26 (dd, 1H), 2.85 (m, 1H), 2.86 (s, 3H), 2.59 (dd, 1H), 2.31 (dd, 1H).

EXAMPLE 69

2-[(Aminocarbonyl)amino]-5 {4-[2-(2-methoxyethoxy)ethoxy]-phenyl}-3-thiophenecarboxamide a) The title compound was prepared from 4-bromo-[2-(2-methoxyethoxy)ethoxy]-benzene in a similar manner to Example 9 (e).
MS (ES) 380 (M+H)$^+$. $^1$H NMR (DMSO-D6) 10.93 (s, 1H), 7.60 (bs, 1H), 7.53 (s, 1H), 7.40 d, 2H), 7.13 (bs, 1H), 6.93 (d, 2H), 6.40 (bs, 2H), 4.08 (m, 2H), 3.72 (m, 2H), 3.56 (m, 2H), 3.46 (m, 2H), 3.30 (s, 3H), 3.25 (s, 3H).
b) 4-Bromo-[2-(2-methoxyethoxy)ethoxy]-benzene
Prepared by the method of M. Ouchi et al, J. Org. Chem., 52, 2420–7, 1987 from 4-bromophenol and 2-(2-methoxyethoxy)ethyl tosylate.
MS (ES) 276 (M+H)$^+$. $^1$H NMR (CDCl$_3$) 7.35 (d, 2H), 67.79 (d, 2H), 4.10 (d, 2H), 3.84 (t, 2H), 3.71 (t, 2H), 3.56 (t, 2H), 3.40 (s, 3H).

EXAMPLE 70

2-[(Aminocarbonyl)amino]-5-{4-[2-(cyclopropylmethoxy)ethoxy]phenyl}-3-thiophenecarboxamide a) The title compound was prepared from 4-(2-[cyclopropylmethoxy]ethoxy)-bromobenzene by the method of Example 22 except that the crude solid was purified by preparative hplc.
MS (ES) 375 (M+H)$^+$. $^1$H NMR (DMSO-D6) 0.15 (m, 2H), 0.45 (m, 2H), 1.0 (m, 1H), 3.35 (m, 2H), 3.7 (m, 2H), 4.1 (m, 2H), 6.9 (br, 2H), 6.95 (d, 2H), 7.25 (m, 1H), 7.4 (d, 2H), 7.55 (s, 1H), 7.65 (m, 1H), 10.95 (brs, 1H).

b) 4-(2-[cyclopropylmethoxy]ethoxy)-bromobenzene

Prepared by the method of Example 10 (b) using 2-(4-bromophenoxyl)ethanol and cyclopropylmethyl bromide.

$^1$H NMR (DMSO-D6) 0.15 (m, 2H), 0.45 (m, 2H), 1.0 (m, 1H), 3.35 (m, 2H), 3.75 (m, 2H), 4.1 (m, 2H), 6.95 (d, 2H), 7.45 (d, 2H).

EXAMPLE 71

2-[(Aminocarbonyl)amino]-5-[6-(2,2-dimethyl-3-pyrrolidinylpropoxy)pyridin-3-yl]-3-thiophenecarboxamide a) The title compound was prepared from 2-(2,2-dimethyl-3-pyrrolidinylpropoxy)-5-bromopyridine by the method as Example 22 except that the crude solid was purified by preparative hplc.

MS (ES) 418 (M+H)$^+$. $^1$H NMR (DMSO-D6) 0.95 (s, 6H), 1.65 (m, 4H), 3.3 (s, 2H), 3.5 (m, 4H), 4.0 (s, 2H), 6.85 (d, 1H), 6.95 (br, 2H), 7.25 (br, 1H), 7.6 (br, 2H), 7.8 (m, 1H), 8.25 (m, 1H), 10.95 (br, 1H).

b) 2-(2,2-Dimethyl-3-pyrrolidinylpropoxy)-5-bromopyridine

Prepared by the method of Example 10 (b) using 2,5-dibromopyridine and 2,2-dimethyl-1-pyrrolidinylpropanol.

MS (ES) 314 (M+H)$^+$.

EXAMPLE 72

2-[(Aminocarbonyl)amino]-5-{3-chloro-4-(tetrahydrofuran-2-ylmethoxy)phenyl}-3-thiophenecarboxamide a) The title compound was prepared from 3-chloro-4-(tetrahydrofuran-2-ylmethoxy)-bromobenzene by the method of Example 22.

MS (ES) 396 (M+H)$^+$. $^1$H NMR (DMSO-D6) 1.85 (m, 4H), 3.6–3.8 (m, 2H), 4.0 (m, 2H), 4.15 (m, 1H), 6.9 (m, 2H), 7.15 (d, 1H), 7.2 (m, 1H), 7.35 (d, 1H), 7.5 (s, 1H), 7.6 (m, 2H), 10.94 (brs, 1H).

b) 3-Chloro-4-(tetrahydrofuran-2-ylmethoxy)bromobenzene.

Prepared by the method of Example 42 (b) using 2-chloro-4-bromophenol and tetrahydrofurfuryl bromide.

$^1$H NMR (DMSO-D6) 1.7–1.9 (m, 4H), 3.7 (m, 2H), 4.0 (m, 2H), 4.15 (m, 1H), 7.1 (d, 1H), 7.4 (m, 1H), 7.6 (d, 1H).

EXAMPLE 73

2-[(Aminocarbonyl)amino]-5-{4-(tetrahydrofuran-2-ylmethoxy)phenyl}-3-thiophenecarboxamide a) The title compound was prepared from 4-(tetrahydrofuran-2-ylmethoxy)-bromobenzene by the method of Example 22 except that the crude solid was purified by preparative hplc.

MS (ES) 362 (M+H)$^+$. $^1$H NMR (DMSO-D6) 1.65–2.0 (m, 4H), 3.7 (m, 2H), 3.95 (m, 2H), 4.15 (m, 1H), 6.85 (m, 2H), 6.95 (d, 2H), 7.2 (m, 1H), 7.4 (d, 2H), 7.55 (s, 1H), 7.6 (m, 1H), 10.92 (s, 1H).

b) 4-(Tetrahydrofuran-2-ylmethoxy)-bromobenzene

Prepared by the method of Example 42 (b) using 4-bromophenol and tetrahydrofurfuryl bromide.

MS (ES) 255 (M−H)$^−$. $^1$H NMR (DMSO-D6) 1.6–1.95 (m, 4H), 3.7 (m, 2H), 3.9 (m, 2H), 4.1 (m, 1H), 6.9 (d, 2H), 7.4 (d, 2H).

EXAMPLE 74

2-[(Aminocarbonyl)amino]-5-[(6-cyclopropylmethylthio)pyridin-3-yl]-3-thiophenecarboxamide a) The title compound was prepared from 5-bromo-2-cyclopropylmethylthio-pyridine in a similar manner to Example 10.

MS (ES) 349 (M+H)$^+$. $^1$H NNMR (DMSO-D6) 0.27–0.38 (m, 2H), 0.49–0.62 (m, 2H), 1.04–1.21 (m, 1H), 3.12 (d, 2H), 7.00 (bs, 1H), 7.33 (d, 1H), 7.34 (bs, 1H), 7.69 (bs, 1H), 7.75 (dd, 1H), 7.78 (s, 1H), 8.59 (d, 1H), 11.03 (s, 1H).

b) 5-Bromo-2-cyclopropylmethylthio-pyridine

Prepared from 2,5-dibromopyridine and cyclopropylmethane thiol by the method of Example 10 (b).

MS (EI) 244 (M)$^{+1}$H NMR (DMSO-D6) 0.25–0.34 (m, 2H), 0.54–0.62 (m, 2H), 1.02–1.22 (m, 1H), 3.09 (d, 2H), 7.07 (d, 1H), 7.56 (dd, 1H), 8.45 (d, 1H).

EXAMPLE 75

2-[(Aminocarbonyl)amino]-5 {4-[2-(2-methoxyethoxy)ethoxy]-3-methylphenyl}-3-thiophenecarboxamide a) The title compound was prepared from 4-bromo-[2-(2-methoxyethoxy)ethoxy]-2-methylbenzene in a similar manner to Example 9 (e).

MS (ES) 394 (M+H)$^+$. $^1$H NMR (DMSO-D6) 10.92 (s, 1H), 7.60 (bs, 1H), 7.52 (s, 1H), 7.21–7.30, (m, 2H), 7.21 (bs, 1H), 6.94 (d, 1H), 6.89 (bs, 2H), 4.10 (m, 2H), 3.72 (m, 2H), 3.59 (m, 2H), 3.44 (m, 2H), 3.23 (s, 3H), 2.15 (s, 3H).

b) 4-Bromo-[2-(2-methoxyethoxy)ethoxy]-2-methylbenzene

Prepared by the method of Example 42 (b) from 4-bromo-2-methylphenol and 2-(2-methoxyethoxy)ethyl tosylate.

MS (EI) 288 (M$^+$). $^1$H NMR (CDCl$_3$) 7.10–7.18 (m, (2H), 6.68 (d, 1H), 4.09 (t, 2H), 3.87 (t, 2H), 3.71 (m, 2H), 3.55 (t, 2H), 3.38 (s, 3H), 2.20 (s, 3H).

EXAMPLE 76

2-[(Aminocarbonyl)amino]-5-{3-chloro-4-[2-(2-methoxyethoxy)ethoxy]phenyl}-3-thiophenecarboxamide a) The title compound was prepared from 4-bromo-2-chloro-[2-(2-methoxyethoxy)ethoxy]benzene in a similar manner to Example 9 (e).

MS (ES) 414 (M+H)$^+$. $^1$H NMR (DMSO-D6) 10.94 (s, 1H), 7.66 (s, 1H), 7.59 (bs, 1H), 7.52 (d, 1H), 7.36, (m, 1H), 7.28 (bs, 1H), 7.16 (d, 1H), 6.93 (bs, 2H), 4.18 (m, 2H), 3.76 (m, 2H), 3.60 (m, 2H), 3.44 (m, 2H), 3.23 (s, 3H).

b) 4-Bromo-2-chloro-[2-(2-methoxyethoxy)ethoxy]benzene

Prepared from 4-bromo-2-chlorophenol and 2-(2-methoxyethoxy)ethyl tosylate by the method of Example 42 (b).

MS (EI) 310 (M$^+$). $^1$H NMR (CDCl$_3$) 7.49 (d, 1H), 7.24–7.32 (m, 2H), 6.81 (d, 1H), 4.17 (t, 2H), 3.89 (t, 2H), 3.73 (t, 2H), 3.56 (t, 2H), 3.39 (s, 3H).

EXAMPLE 77

2-[(Aminocarbonyl)amino]-5-[2-(4-methylpiperazinylmethyl)phenyl]-3-thiophenecarboxamide a) 2-[(Aminocarbonyl)amino]-5-[2-formylphenyl]-3-thiophenecarboxamide (0.1 g) and sodium tri-acetoxy borohydride (0.1 g) were mixed with tetrahydrofuran (10 ml). N-Methylpiperazine (0.04 g) was added and the mixture stirred at room temperature for 18 h. Separation was achieved using cation exchange chromatography eluting with ammonia/methanol/dichloromethane mixtures. This gave the title compound (0.07 g).

MS (ES) 374 (M+H)$^+$. $^1$H NMR (DMSO-D6) 2.2 (s, 3H), 2.35 (m, 4H), 3.3 (m, 4H), 3.5 (s 2H), 6.8 (bs, 2H), 7.2–7.5 (m, 6H), 7.7 (bs 1H), 11.0 (s, 1H).

b) 2-[(Aminocarbonyl)amino]-5-[2-formylphenyl]-3-thiophenecarboxamide

Prepared from 2-formylphenyl boronic acid in a similar manner to Example 9 (e).

MS (ES) 290 (M+H)$^+$. $^1$H NMR (DMSO-D6) 7.0 (bs, 2H), 7.35 (bs, 1H), 7.4 (s, 1H), 7.5 (td, 1H), 7.6 (dd, 1H), 7.7 (td, 1H), 7.8 (bs, 1H), 7.9 (dd, 1H), 10.1 (s, 1H), 11.1 (s, 1H).

EXAMPLE 78

2-[(Aminocarbonyl)amino]-5-[2-(4-isopropylpiperazinylmethyl)phenyl-3-thiophenecarboxamide The title compound was prepared from N-isopropylpiperazine in a similar manner to Example 77 (a).

MS (ES) 401 (M+H)$^+$. $^1$H NMR (DMSO-D6) 1.0 (d, 6H), 2.3–2.4 (m, 8H), 3.5 (s 2H), 6.9 (bs, 2H), 7.25–7.4 (m, 5H), 7.45 (m, 1H), 7.65 (bs 1H), 11.0 (s, 1H).

EXAMPLE 79

2-[(Aminocarbonyl)amino]-5-[2-(4-t-butyloxycarbonylpiperazinylmethyl)phenyl]-3-thiophenecarboxamide The title compound was prepared from N-t-butyloxycarbonylpiperazine in a similar manner to Example 77 (a).

MS (ES) 460 (M+H)$^+$. $^1$H NMR (DMSO-D6) 1.4 (d, 9H), 2.3 (m, 4H), 3.5 (s 2H), 6.9 (bs, 2H), 7.2–7.5 (m, 6H), 7.65 (bs 1H), 11.0 (s, 1H).

EXAMPLE 80

2-[(Aminocarbonyl)amino]-5-[4-(pyrrolidinylmethyl)phenyl]thiophene-3-carboxamide a) The title compound was prepared from 1-(4-bromobenzyl)pyrrolidine in a similar manner to Example 10 (a).

LCMS (ES) 345 (M+H)$^+$. $^1$H NMR (DMSO-D6) 1.70 (s, 4H), 2.53 (s, 4H+DMSO), 3.62 (s, 2H), 6.90 (s, 2H), 7.25 (m, 1H), 7.30 (d, 2H), 7.45 (d, 2H), 7.62 (m, 1H), 7.69 (s, 1H), 10.97 (s, 1H).

b) 1-(4-Bromobenzyl)pyrrolidine

Prepared in a similar manner to Example 43 (b) but using pyrrolidine.

MS (ES) 240/242 (M+H)$^+$. $^1$H NMR (DMSO-D6) 1.65 (m, 4H), 2.38 (m, 4H), 3.50 (s, 2H), 7.22 (m, 2H), 7.45 (m, 2H).

EXAMPLE 81

2-[(Aminocarbonyl)amino]-5-[2-(2-(4,4-difluoropiperidin-1-yl)ethoxy)phenyl]-3-thiophenecarboxamide a) The title compound was prepared from 4,4-difluoro-(2-(2-bromophenoxy)ethyl)piperidine in a similar manner to Example 9 (e).

MS (ES) 425 (M+H)$^+$. $^1$H NMR (DMSO-D6) 1.9 (m, 4H), 2.7 (m, 4H), 2.9 (t, 2H), 4.2 (t, 2H), 6.9 (bs, 2H), 7.0 (t, 1H), 7.1 (d, 1H), 7.2 (m, 2H), 7.6 (m, 2H), 7.75 (s, 1H), 11.0 (s, 1H).

b) 4,4-Difluoro-(2-(2-bromophenoxy)ethyl)piperidine 2-(2-Bromophenoxy)ethyl tosylate (1.86 g), 4,4-difluoropiperidine (0.73 g) and potassium carbonate (0.97 g) were mixed with dimethylformamide (30 ml) and heated to 60° C. for 18 h. The mixture was cooled and added to water (300 ml). The mixture was extracted with diethyl ether (×3), dried and evaporated. Purification was achieved using cation exchange chromatography eluting with ammonia/methanol/dichloromethane mixtures yielding, 4-difluoro-(2-(2-bromophenoxy)ethyl)piperidine (0.77 g).

MS (ES) 321 (M+H)$^+$. $^1$H NMR (DMSO-D6) 1.8–2.1 (m, 4H), 2.7 (m, 4H), 2.8 (t, 2H), 4.1 (t, 2H), 6.9 (td, 1H), 7.1 (dd, 1H), 7.3 (td, 1H), 7.55 (dd, 1H).

c) 2-(2-Bromophenoxy)ethyl tosylate 2-(2-Bromophenoxy)ethanol (17.4 g) was dissolved in dichloromethane (250 ml) and cooled to 0° C. Triethylamine (9.7 g) was added along with tosyl chloride (18.3 g). The mixture was stirred for 2 h, then added to water (500 ml). The organics were washed twice with 2N hydrochloric acid and dried. Separation was achieved using silica chromatography eluting with hexane/ethyl acetate mixtures. This gave 2-(2-bromophenoxy)ethyl tosylate (14.4 g).

$^1$H NMR (DMSO-D6) 2.4 (s, 2H), 4.3 (t, 2H), 4.35 (t, 2H), 6.9 (td, 1H), 7.0 (dd, 1H), 7.3 (td, 1H), 7.5 (d, 2H), 7.6 (dd, 1H), 7.8 (d, 2H).

d) 2-(2-Bromophenoxy)ethanol

Potassium carbonate (23.8 g) and 2-bromophenol (14.9 g) were mixed with dimethylformamide (150 ml). 2-Bromoethanol (12.9 g) was added and the mixture heated to 50° C. for 18 h. The mixture was cooled and added to water (1500 ml). The product was extracted into diethyl ether (×3) and washed twice with dilute sodium hydroxide solution. Evaporation gave 2-(2-bromophenoxy)ethanol (17.4 g).

$^1$H NMR (DMSO-D6) 3.75 (m, 2H), 4.0 (t, 2H), 4.9 (t, 1H), 6.8 (t, 1H), 7.1 (d, 1H), 7.3 (d, 1H), 7.55 (d, 1H).

EXAMPLE 82

2-[(Aminocarbonyl)amino]-5-[2-(2-(3,3-difluoropyrrolidin-1-yl)ethoxy)phenyl]-3-thiophenecarboxamide a) The title compound was prepared from 3,3-difluoro-(2-(2-bromophenoxy)ethyl)pyrrolidine in a similar manner to Example 9 (e).

MS (ES) 411 (M+H)$^+$. $^1$H NMR (DMSO-D6) 2.2 (m, 2H), 2.9 (t, 2H), 3.0 (m, 4H), 4.2, (t, 2H), 6.9 (bs, 2H), 7.0 (t, 1H), 7.15 (d, 1H), 7.2 (m, 2H), 7.6 (m, 2H), 7.8 (s, 1H), 11.0 (s, 1H).

b) 3,3-Difluoro-(2-(2-bromophenoxy)ethyl)pyrrolidine

Prepared from 3,3-difluoropyrrolidine in a similar manner to Example 81 (a).

MS (ES) 307 (M+H)$^+$. $^1$H NMR (DMSO-D6) 2.2 (m, 2H), 2.9 (m, 4H), 3.1 (t, 2H), 4.1, (t, 2H), 6.9 (td, 1H), 7.1 (dd, 1H), 7.3 (td, 1H), 7.6 (dd, 1H).

EXAMPLE 83

3-[(Aminocarbonyl)amino]-5-[4-(morpholin-4-ylmethyl)phenyl]thiophene-2-carboxamide a) The title compound was prepared from 3-amino-5-[4-(morpholin-4-ylmethyl)phenyl]thiophene-2-carboxamide in a similar manner to Example 9(b).

MS (ES) 361 (M+H)$^+$. $^1$H NMR (DMSO-D6) 2.35 (m, 4H), 3.5 (s, 2H), 3.55 (m, 4H), 6.55 (brs, 2H), 7.4 (m, 3H), 7.55 (d, 2H), 8.2 (s, 1H), 10.03 (brs, 1H).

b) 3-[4-(Morpholin-4-ylmethyl)phenyl]-3-oxopropanenitrile (i) To a solution of methyl 4-bromomethylbenzoate (14.75 g) in dimethylformamide (50 ml), cooled to 5° C., was added rapidly morpholine (13.8 ml). The mixture was stirred at room temperature for 2 h. The mixture was partitioned between diethyl ether and water.

The organic layer was washed with water, dried (MgSO$_4$), evaporated and purified by column chromatography eluting with ethyl acetate/iso-hexane (20:80) to give methyl 4(morpholin-4-ylmethyl)benzoate (14.13 g) as an oil.

(ii) To a solution of acetonitrile (1.35 ml) in tetrahydrofuran (80 ml), cooled to 5° C., was added sodium hydride (0.94 g, 60% dispersion in oil). The mixture was stirred for 30 minutes before the addition of a solution of methyl 4-(morpholin-4-ylmethyl)benzoate (5.53 g) in tetrahydrofuran (20 ml). The resulting mixture was heated to 70° C. for 5 h. The mixture was cooled, quenched with saturated ammonium chloride (20 ml) and extracted with ethyl acetate. The organic extracts were dried (MgSO$_4$) and evaporated to give a gum which was purified by column chromatography eluting with a 20–100% ethyl acetate/iso-hexane gradient to give 3-[4-(morpholin-4-ylmethyl)phenyl]-3-oxopropanenitrile (0.97 g).

MS (ES) 245 (M+H)$^+$. $^1$H NMR (CDCl$_3$) 2.45 (m, 4H), 3.55 (s, 2H), 3.7 (m, 4H), 4.05 (s, 2H), 7.5 (d, 2H), 7.9 (d, 2H).

c) cis/trans-2-Cyano-1-[4-(morpholin-4-ylmethyl)phenyl]ethenyl 4-methylbenzene sulphonate To a solution of 3-[4-(morpholin-4-ylmethyl)phenyl]-3-oxopropanenitrile (0.96 g) in tetrahydrofuran (12 ml) was added sodium hydride (190 mg, 60% dispersion in oil) and the resulting mixture was stirred at room temperature for 1 h. A solution of p-toluenesulphonyl chloride (0.9 g) in tetrahydrofuran (20 ml) was added and the resulting mixture was stirred at room temperature for 3 h. The reaction was quenched with water and extracted with ethyl acetate. The organic extracts were dried (MgSO$_4$) and evaporated to give a gum, which was purified by column chromatography eluting with ethyl acetate/isohexane (50:50) to give a cis/trans mixture of 2-cyano-1-[4-(morpholin-4-ylmethyl)phenyl] ethenyl 4-methylbenzenesulphonate (0.94 g) as an oil.

MS (ES) 399 (M+H)$^+$.

d) cis/trans-2-({2-Cyano-1-[4-(morpholin-4-ylmethyl)phenyl]ethenyl}thio)acetamide To a solution of the above cis/trans mixture of 2-cyano-1-[4-(morpholin-4-ylmethyl)phenyl] ethenyl 4-methylbenzenesulphonate (940 mg) in acetonitrile (20 ml) was added freshly prepared thioacetamide (430 mg) followed by triethylamine (0.75 ml). The resulting mixture was stirred at room temperature for 18 h. Further amounts of thioacetamide (660 mg) and triethylamine (1.5 ml) were added and the resulting mixture was stirred for a further 3 h. The mixture was evaporated and the resulting gum was purified by column chromatography eluting with a 1–8% methanol/dichloromethane gradient to give a cis/trans mixture of 2-({2-cyano-1-[4-(morpholin-4-ylmethyl)phenyl]ethenyl}thio)acetamide (712 mg) as a gum.

MS (ES) 318 (M+H)$^+$.

e) 3-Amino-5-[4-(morpholin-4-ylmethyl)phenyl]thiophene-2-carboxamide

To a suspension of cis/trans-2-({2-cyano-1-[4-(morpholin-4-ylmethyl)phenyl]ethenyl}thio) acetamide (705 mg) in tetrahydrofuran (15 ml) was added potassium t-butoxide (250 mg) and the resulting mixture was stirred at room temperature for 18 h. The mixture was poured into 50% brine and extracted with ethyl acetate. The organic layer was dried (MgSO$_4$) and evaporated to give a gum, which was purified by column chromatography eluting with a 1–8% methanol/dichloromethane gradient to give 3-amino-5-[4-(morpholin-4-ylmethyl)phenyl]-thiophene-2-carboxamide (161 mg).

MS (ES) 318 (M+H)$^+$. $^1$H NMR (DMSO-D6) 2.35 (m, 4H), 3.5 (s, 2H), 3.6 (m, 4H), 6.45 (s, 2H), 6.85 (s, 2H), 6.9 (s, 1H), 7.35 (d, 2H), 7.5 (d, 2H).

EXAMPLE 84

3-[(Aminocarbonyl)amino]-5-[4-(cis-2,6-dimethylmorpholin-4-ylmethyl)phenyl]thiophene-2-carboxamide a) The title compound was prepared from 3-amino-5-[4-(cis-2,6-dimethylmorpholin-4-ylmethyl)phenyl]thiophene-2-carboxamide in a similar manner to Example 9 (b).

MS (ES) 389 (M+H)$^+$. $^1$H NMR (DMSO-D6) 1.0 (d, 6H), 1.65 (t, 2H), 2.7 (d, 2H), 3.45 (s, 2H), 3.75 (m, 2H), 6.6 (brs, 2H), 7.35 (d+s, 4H), 7.55 (d, 2H), 8.2 (s, 1H), 10.03 (brs, 1H).

b) 3-Amino-5-[4-(cis-2,6-dimethylmorpholin-4-ylmethyl)phenyl]thiophene-2-carboxamide Prepared in a similar manner to Example 83 (b-e) using cis 2,6-dimethylmorpholine.

MS (ES) 346 (M+H)$^+$. $^1$H NMR (DMSO-D6) 1.1 (d, 6H), 1.8 (t, 2H), 2.7 (d, 2H), 3.5 (s, 2H), 3.7 (m, 2H), 5.2 (s, 2H), 5.7 (s, 2H), 6.8 (s, 1H), 7.35 (d, 2H), 7.5 (d, 2H).

EXAMPLE 85

2-[(Aminocarbonyl)amino]-5-[4-(cis-2,6-dimethylmorpholin-4-ylmethyl)phenyl]thiophene-3-carboxamide a) The title compound was prepared from N-(4-bromobenzyl)-cis-2,6-dimethylmorpholine in a similar manner to Example 10 (a).

MS (ES) 389 (M+H)$^+$. $^1$H NMR (DMSO-D6) 1.0 (d, 6H), 1.65 (t, 2H), 2.7 (m, 2H), 3.4 (s, 2H), 3.55 (m, 2H), 7.0 (brs, 2H), 7.3 (m, 3H), 7.5 (d, 2H), 7.7 (s, 1H), 7.7 (brs, 1H), 11.0 (s, 1H).

b) N-(4-Bromobenzyl)-cis-2,6-dimethylmorpholine

The compound was prepared in a similar manner to Example 43 (b).

MS (ES) 284, 286 (M+H)$^+$. $^1$H NMR (CDCl$_3$) 1.15 (d, 6H), 1.7 (t, 2H), 2.65 (d, 2H), 3.4 (s, 2H), 3.7 (m, 2H), 7.2 (d, 2H), 7.45 (d, 2H).

EXAMPLE 86

2-[(Aminocarbonyl)amino]-5-[(6-{4-morpholino}methyl pyridin-3-yl]thiophene-3-carboxamide a) The title compound was prepared from 5-bromo-2-[(4-morpholino)methyl]pyridine in a similar manner to Example 9(e).

MS (ES) 362 (M+H)$^+$. $^1$H NMR (DMSO-D6) 2.4 (m, 4H), 3.6 (s, 2H), 3.6 (m, 4H), 7.0 (brs, 2H), 7.3 (brs, 1H), 7.45 (d, 1H), 7.7 (brs, 1H), 7.8 (s, 1H), 7.85 (dd, 1H), 8.65 (d, 1H), 11.0 (brs, 1H).

b) 5-Bromo-2-[(4-morpholino)methyl]pyridine

To a solution of 5-bromopyridine-2-carboxaldehyde (0.88 g) in anhydrous dichloroethane (20 ml) was added morpholine (0.48 ml), followed by glacial acetic acid (0.29 ml) and sodium triacetoxyborohydride (1.49 g). The resulting mixture was stirred at room temperature for 2 h. The mixture was quenched with saturated sodium bicarbonate (20 ml) and stirred for 30 minutes. The mixture was extracted with ethyl acetate, dried (MgSO$_4$) and evaporated to give a gum, which was purified by column chromatography eluting with ethyl acetate/iso-hexane (1:1) to give a colourless oil (1.035 g).

MS (ES) 257,259 (M+H)$^+$. $^1$H NMR (CDCl$_3$) 2.5 (m, 4H), 3.6 (s, 2H), 3.7 (m, 4H), 7.35 (d, 1H), 7.75 (dd, 1H), 8.6 (d, 1H).

EXAMPLE 87

2-[(Aminocarbonyl)amino]-5-[4-(8-oxa-3-azabicyclo[3.2.1]oct-3-ylmethyl)phenyl]thiophene-3-carboxamide a) The title compound was prepared from 3-(4-bromobenzyl)-8-oxa-3-azabicyclo[3.2.1]octane in a similar manner to Example 9(e).

MS (ES) 387 (M+H)$^+$. $^1$H NMR (DMSO-D6) 1.7 (m, 2H), 1.85 (m, 2H), 2.15 (m, 2H), 3.3–3.45 (m, 4H), 4.15 (d, 2H), 6.95 (brs, 2H), 7.3 (d, 2H), 7.3 (brs, 1H), 7.5 (d, 2H), 7.7 (brs+s, 2H), 10.95 (brs, 1H).

b) 3-(4-Bromobenzyl)-8-oxa-3-azabicyclo[3.2.1]octane

This compound was prepared in a similar manner to example 43(b) but using 8-oxa-3-azabicyclo[3.2.1]octane.

MS (ES) 282 (M+H)$^+$. $^1$H NMR (CDCl$_3$) 1.9 (m, 2H), 1.95 (m, 2H), 2.3 (d, 2H), 2.5 (d, 2H), 3.4 (s, 2H), 4.3 (m, 2H), 7.2 (d, 2H), 7.4 (d, 2H).

EXAMPLE 88

2-[(Aminocarbonyl)amino]-5-[3-(morpholin-4-ylmethyl)$_4$ isobutoxyphenyl]thiophene-3-carboxamide a) The title compound was prepared from 4-(5-bromo-2-isobutoxybenzyl)morpholine in a similar manner to Example 9(e).

MS (ES) 433 (M+H)$^+$. $^1$H NMR (DMSO-D6) 1.0 (d, 6H), 2.05 (m, 1H), 2.4 (m, 4H), 3.5 (s, 2H), 3.55 (m, 4H), 3.75 (d, 2H), 6.9 (brs, 2H), 7.0 (d, 1H), 7.2 (brs, 1H), 7.35 (dd, 1H), 7.45 (d, 1H), 7.55 (s, 1H), 7.7 (brs, 1H), 10.9 (brs, 1H).

b) 4-(5-Bromo-2-isobutoxybenzyl)morpholine

To a solution of 5-bromo-2-isobutoxybenzaldehyde (2.46 g) in 1,2-dichloroethane (40 ml) was added morpholine (0.96 ml) and acetic acid (0.57 ml). The mixture was stirred for 30 minutes before the addition of sodium triacetoxyborohydride (3.04 g). The resulting mixture was stirred at room temperature for 3 h. The reaction was quenched with saturated sodium bicarbonate (30 ml) and stirred for 30 minutes before extraction with ethyl acetate.

The organic extracts were dried (MgSO$_4$) and evaporated to give an oil, which was purified by column chromatography eluting with ethyl acetate/iso-hexane (20:80) to give 4-(5-bromo-2-isobutoxybenzyl)morpholine (2.88 g) as an oil.

MS (ES) 328 (M+H)$^+$. $^1$H NMR (CDCl$_3$) 1.05 (d, 6H), 2.1 (m, 1H), 2.5 (m, 4H), 3.5 (s, 2H), 3.7 (m, 6H), 6.7 (d, 1H), 7.3 (m, 1H), 7.5 (m, 1H).

c) 5-Bromo-2-isobutoxybenzaldehyde

To a solution of 5-bromo-2-hydroxybenzaldehyde (7.63 g) in dimethylformamide (40 ml) was added anhydrous potassium carbonate (15.7 g) followed by 1-bromo-2-methylpropane (6.2 ml). The resulting mixture was heated to 70° C. for 18 h. The mixture was partitioned between water and ethyl acetate. The organic layer was washed with 2N sodium hydroxide, dried (MgSO$_4$) and evaporated to give an oil which was purified by column chromatography eluting with ethyl acetate/iso-hexane (10:90) to give 5-bromo-2-isobutoxybenzaldehyde (9.52 g) as an oil.

MS (ES) 256 (M+H)$^+$. $^1$H NMR (CDCl$_3$) 1.1 (d, 6H), 2.2 (m, 1H), 3.85 (d, 2H), 6.9 (d, 1H), 7.6 (dd, 1H), 7.9 (d, 1H), 10.45 (brs, 1H).

EXAMPLE 89

2-[(Aminocarbonyl)amino]-5-[3-(morpholin-4-ylmethyl)phenyl]thiophene-3-carboxamide The title compound was prepared from N-(3-bromobenzyl)morpholine in a similar manner to Example 43 except that the product was adsorbed on to reverse phase silica and eluted with water/acetonitrile/trifluoroacetic acid to give a cream solid (120 mg).

MS (ES) 361 (M+H)$^+$. $^1$H NMR (DMSO-D6) 2.37 (brs, 4H), 3.47 (s, 2H), 3.59 (brs, 4H), 6.99 (brs, 2H), 7.17 (d, 1H), 7.34 (t+brs, 2H), 7.42 (d, 1H), 7.47 (s, 1H), 7.74 (s, 2H), 11.02 (s, 1H).

EXAMPLE 90

2-[(Aminocarbonyl)amino]-5-(4-{[2-(methoxymethyl)morpholin-4-yl]methyl}phenyl)thiophene-3-carboxamide The title compound was prepared from 4-(4-bromobenzyl)-2-(methoxymethyl)morpholine (0.7 g) in a similar manner to Example 43 to give the product as a light brown solid (28 mg).

MS (ES) 405 (M+H)$^+$. $^1$H NMR (DMSO-D6) 1.80 (t, 1H), 2.04 (m, 1H), 2.64 (m, 2H), 3.19 (s, 3H), 3.20–3.40 (m, 2H), 3.40–3.57 (m, 4H), 3.74 (d, 1H), 6.92 (brs, 2H), 7.26 (brs, 1H), 7.29 (d, 2H), 7.47 (d, 2H), 7.68 (brs, 1H), 7.70 (s, 1H), 10.97 (s, 1H).

4-(4-Bromobenzyl)-2-(methoxymethyl)morpholine 2-(Methoxymethyl)morpholine (1 g), anhydrous potassium carbonate (2.1 g), 1-bromo-4-(bromomethyl)benzene (1.91 g) and dimethylformamide (30 ml) were stirred at ambient temperature for 48 h, evaporated, and the residue purified by column chromatography using a gradient of ether/isohexane; 0/100 to 100/0, 1/9 MeOH/dichloromethane and finally 2M ammonia in methanol to give the product as a solid (0.7 g).

MS (ES) 300 (M+H)+. 1H NMR (CDCl3) 1.89 (t, 1H), 2.11 (m, 1H), 2.58 (m, 2H), 3.28 (s, 3H), 3.30 (m, 2H), 3.37 (s, 2H), 3.60 (m, 2H), 3.81 (m, 1H), 7.12 (d, 2H), 7.36 (d, 2H).

EXAMPLE 91

2-(Aminocarbonyl)amino]-5-[3-fluoro-4-(morpholin-4-ylmethyl)phenyl]thiophene-3-carboxamide a) 4-(4-Bromo-2-fluorobenzyl)morpholine (1.2 g) was stirred in tetrahydrofuran (25 ml) under argon and the mixture cooled to −70° C. n-Butyl lithium (4.1 ml, 1.6M solution in hexane) was added dropwise over 20 minutes and the mixture was stirred for a further 30 minutes at −70° C. Triisopropylborate (1.52 ml) was then added in one portion and the reaction mixture was allowed to warm to room temperature over 2 h, then concentrated in vacuo. 1,2-Dimethoxyethane (45 ml) was added to the residue and the mixture was purged with a stream of argon. 2-[(Aminocarbonyl)amino]-5-bromo-3-thiophenecarboxamide (0.385 g) was then added, followed by saturated aqueous sodium hydrogen carbonate (5 ml) and Pd(PPh3)4 (100 mg). The mixture was stirred at 85° C. under argon for 18 h. After cooling, the solvent was removed in vacuo and the residue was partitioned between 2M aqueous sodium hydroxide (50 ml) and dichloromethane (50 ml). The aqueous layer was extracted further with dichloromethane (50 ml) and the compound was isolated by neutralisation of the basic aqueous phase, followed by filtration, washing with water and drying of the resulting precipitate to give the product as a brown solid (370 mg).

MS (ES) 379 (M+H)+. 1H NMR (DMSO-D6) 2.38 (t, 4H) 3.50 (s, 2H), 3.55 (t, 4H), 6.95 (brs, 2H), 7.25 (s, 1H), 7.30 (d, 2H), 7.39 (t, 1H), 7.62 (brs, 1H), 7.79 (s, 1H), 10.98 (brs, 1H).

b) 4-(4-Bromo-2-fluorobenzyl)morpholine

4-Bromo-2-fluorobenzyl bromide (3.0 g) and morpholine (2.15 ml) were stirred in dimethylformamide (30 ml) at ambient temperature for 18 h. The mixture was partitioned between diethyl ether (80 ml) and water (80 ml). The aqueous phase was extracted further with diethyl ether (80 ml) and the combined organic phases were dried (magnesium sulfate) and concentrated in vacuo. The residue was purified by column chromatography, eluting with a gradient of 0–30% ethyl acetate/iso-hexane to give the product as a colourless oil (2.92 g).

MS (ES) 274 (M+H)+. 1H NMR (DMSO-D6) 2.35 (t, 4H), 3.48 (s, 2H), 3.55 (t, 4H), 7.38 (q, 2H), 7.49 (d, 1H).

EXAMPLE 92

2-[(Aminocarbonyl)amino]-5-[3-chloro-4-(morpholin-4-methyl)phenyl]thiophene-3-carboxamide a) The title compound was prepared from 4-(4-bromo-2-chlorobenzyl)morpholine in a similar manner to Example 91 (a) to give a brown solid (270 mg).

MS (ES) 395 (M+H)+. 1H NMR (DMSO-D6) 2.40 (m, 4H) 3.51 (s, 2H), 3.57 (m, 4H), 6.97 (brs, 2H), 7.30 (brs, 1H), 7.43 (d, 1H), 7.48 (d, 1H), 7.55 (s, 1H), 7.62 (brs, 1H), 7.80 (s, 1H), 10.97 (s, 1H).

b) 4-(4-Bromo-2-chlorobenzyl)morpholine

The title compound was prepared from 4-bromo-1-(bromomethyl)-2-chlorobenzene in a similar manner to Example 91 (b) except that the residue was purified by column chromatography, eluting with a gradient of 0–20% ethyl acetate/iso-hexane to give the product as a colourless oil (1.20 g).

MS (ES) 290 (M+H)+. 1H NMR (DMSO-D6) 2.40 (t, 4H), 3.50 (s, 2H), 3.57 (t, 4H), 7.42 (d, 1H), 7.53 (d, 1H), 7.69 (s, 1H).

c) 4-Bromo-1-(bromomethyl)-2-chlorobenzene

4-Bromo-2-chlorotoluene (7.02 g) and N-bromosuccinimide (6.07 g) was stirred in chlorobenzene (50 ml) under ultraviolet light at 100° C. for 18 h. The reaction mixture was filtered and the filtrate was concentrated in vacuo. The residue was purified by medium-pressure liquid chromatography, eluting with iso-hexane, to give a colourless oil (2.65 g).

MS (EI) 282 M+. 1H NMR (DMSO-D6) 4.70 (s, 2H), 7.58 (s, 2H), 7.78 (s, 1H).

EXAMPLE 93

2-[(Aminocarbonyl)amino]-5-{4-[(4,4-difluoropiperidin-1-yl)methyl]phenyl}thiophene-3-carboxamide a) 4,4-Difluoro-1-(4-bromobenzyl)piperidine (0.81 g) was stirred in tetrahydrofuran (20 ml) under argon, and the mixture cooled to −65° C. n-Butyl lithium (2.66 ml, 1.6M solution in hexane) was added dropwise over 20 minutes and the mixture was stirred for a further 30 minutes at −65° C. Triisopropylborate (1.31 ml) was then added in one portion and the reaction mixture was allowed to warm to room temperature over 2 h., then concentrated in vacuo. 1,2-Dimethoxyethane (25 ml) was added to the residue and mixture was purged with a stream of argon. 2-[(Aminocarbonyl)amino]-5-bromo-3-thiophenecarboxamide (0.250 g) was then added followed by saturated aqueous sodium hydrogen carbonate (5 ml) and Pd(PPh3)4 (100 mg). The mixture was stirred at 80° C. under argon for 18 h. After cooling, the solvent was removed in vacuo and the residue was partitioned between 2M. aqueous sodium hydroxide (15 ml) and dichloromethane (15 ml). The solid remaining undissolved at the interface was collected by filtration, washed with water and dichloromethane and dried to give the product as a grey solid (0.243 g).

LCMS (ES) 395 (M+H)+. 1H NMR (DMSO-D6) 1.90 (m, 4H), 2.50 (m, obscured), 3.50 (s, 2H), 6.90 (s, 2H), 7.25 (m, 3H), 7.42 (d, 2H), 7.62 (s, 1H), 7.68 (s, 1H), 10.97 (s, 1H).

b) 4,4-Difluoro-1-(4-bromobenzyl)piperidine

4-Bromobenzyl bromide (1.55 g) and 4,4-difluoropiperidine (1.50 g) were stirred in dimethylformamide (30 ml) for 18 h. The mixture was partitioned between diethyl ether (40 ml) and water (40 ml). The aqueous phase was extracted further with ether (40 ml) and the combined organic phases were washed with water (50 ml), dried (MgSO4) and concentrated in vacuo to give the product as a white crystalline solid (1.57 g).

1H NMR (DMSO-D6) 1.90 (m, 4H), 2.45 (m, 4H obscured), 3.48 (s, 2H), 7.22 (d, 2H), 7.50 (d, 2H).

EXAMPLE 94

2-[(Aminocarbonyl)amino]-5-[4-(1-{piperidin-1-yl}ethyl)phenyl]thiophene-3-carboxamide a) The title compound was prepared from 1-[1-(4-bromophenyl)ethyl]piperidine in a similar manner to Example 93 (a) except that the compound was isolated by neutralisation of the basic aqueous phase with aqueous 6M HCl, followed by filtration, washing with water and drying of the resulting precipitate to give a light brown solid (307 mg).

MS (ES) 373 (M+H)+. $^1$H NMR (DMSO-D6) 1.35 (m, 5H), 1.50 (m, 4H), 2.45 (m, obscured), 3.55 (m, 1H), 6.60 (s, 2H), 7.12 (s, 2H), 7.30 (d, 2H), 7.45 (d, 2H), 7.60 (s, 1H), 10.90 (s, 1H).

b) 1-[1-(4-Bromophenyl)ethyl]piperidine

4-Bromoacetophenone (1.95 g), piperidine (0.97 ml) and titanium(IV) isopropoxide (3.64 ml) were stirred under argon at room temperature for 1 h. Ethanol (10 ml) was added, followed by sodium cyanoborohydride (0.41 g) and mixture stirred for 18 h. Water (2 ml) was then added and the mixture stirred for 20 minutes. The resulting inorganic precipitate was filtered off, washed with ethanol (20 ml) and the combined organic phase was concentrated in vacuo, redissolved in toluene and purified by Bondelute® chromatography, eluting with 0–20% ethyl acetate/iso-hexane to give the product as a pale yellow oil (1.07 g).

MS (ES) 268 (M+H)+. $^1$H NMR (DMSO-D6) 1.21 (d, 3H), 1.30 (m, 2H), 1.42 (m, 4H), 2.22 (m, 4l), 3.40 (q, 1H), 7.20 (d, 2H), 7.45 (d, 2H).

EXAMPLE 95

2-[(Aminocarbonyl)amino]-5-{4-[(1R)-1-morpholin-4-ylethyl]phenyl}thiophene-3-carboxamide a) The title compound was prepared from 4-[(1R)-1-(4-bromophenyl)ethyl]morpholine in a similar manner to Example 93 (a) except that the compound was isolated by neutralisation of the basic aqueous phase with aqueous 6M HCl, followed by filtration, washing with water and drying of the resulting precipitate to give a pale brown solid (278 mg).

MS (ES) 375 (M+H)+. $^1$H NMR (DMSO-D6) 1.22 (d, 3H), 2.25 (m, 2H), 2.40 (m, 2H), 3.30 (m, 1H), 3.50 (m, 4H), 6.90 (brs, 2H), 7.25 (m, 3H), 7.42 (d, 2H), 7.65 (m, 2H), 10.97 (s, 1H).

b) (1R)-4-[1-(4-Bromophenyl)ethyl]morpholine (R)-(+)-1-(4-Bromophenyl)ethylamine (0.98 g), 2,2'-dibromodiethyl ether (1.36 g) and diisopropylethylamine (2.5 ml) were stirred in dimethylformamide (20 ml) under argon at 100° C. for 18 h. The reaction mixture was allowed to cool to room temperature, then partitioned between diethyl ether (50 ml) and water (50 ml). The aqueous phase was extracted further with diethyl ether (50 ml) and the combined organic phases were washed with water (100 ml), dried (MgSO4), concentrated in vacuo, redissolved in toluene and purified by Bondelute® chromatography, eluting with 0–50% ethyl acetate/iso-hexane to give the product as a yellow oil (0.86 g).

LCMS (ES) 270 (M+H)+. $^1$H NMR (DMSO-D6) 1.21 (d, 3H), 2.20 (m, 2H), 2.38 (m, 2H), 3.30 (m, 1H), 3.50 (m, 4H), 7.22 (d, 2H), 7.48 (d, 2H).

EXAMPLE 96

2-[(Aminocarbonyl)amino]-5-(4-{4-(2-methoxyethoxy)piperazin-1-yl]methyl}phenyl)thiophene-3-carboxamide a) The title compound was prepared from 1-(4-bromobenzyl)-4-(2-methoxyethyl)piperazine in a similar manner to Example 93 (a) except that the compound was isolated by neutralisation of the basic aqueous phase with aqueous 6M HCl, followed by filtration, washing with water and drying of the resulting precipitate to give a light brown solid (271 mg).

MS (ES) 418 (M+H)+. $^1$H NMR (DMSO-D6) 2.25–2.50 (m, obscured), 3.20 (s, 3H), 3.40 (m, 4H), 6.90 (brs, 2H), 7.22 (m, 3H), 7.42 (d, 2H), 7.60 (brs, 1H), 7.63 (s, 1H), 10.96 (s, 1H).

b) 1-(4-Bromobenzyl)-4-(2-methoxyethoxy)piperazine

4-Bromobenzyl bromide (2.0 g) and 1-(2-methoxyethyl)piperazine (2.31 g) were stirred in dimethylformamide (30 ml) for 18 h. The mixture was partitioned between diethyl ether (30 ml) and water (30 ml). The aqueous phase was extracted further with ether (30 ml) and the combined organics were washed with water (50 ml), dried (MgSO4), concentrated in vacuo and purified by Bondelute® chromatography, eluting with 0–100% ethyl acetate/iso-hexane followed by 10–50% methanol/ethyl acetate to give the product as a yellow oil (1.61 g).

$^1$H NMR (DMSO-D6) 2.22–2.45 (m, 10H), 3.20 (s, 3H), 3.40 (m, 4H), 7.20 (m, 2H), 7.45 (m, 2H).

EXAMPLE 97

2-[(Aminocarbonyl)amino]-5-[4-(piperidin-1-ylmethyl)phenyl]thiophene-3-carboxamide a) The title compound was prepared from 1-(4-bromobenzyl)piperidine in a similar manner to Example 93 (a) except that the compound was isolated by neutralisation of the basic aqueous phase with aqueous 6M HCl, followed by filtration, washing with water and drying of the resulting precipitate to give a pale brown solid (182 mg).

LCMS (ES) 359 (M+H)+. $^1$H NMR (DMSO-D6) 1.40 (m, 2H), 1.50 (m, 4H), 2.42 (m, 4H), 3.50 (brs, 2H), 6.92 (m, 2H), 7.28 (m, 3H), 7.45 (m, 2H), 7.65 (m, 2H), 10.98 (brs, 1H).

b) 1-(4-Bromobenzyl)piperidine

This compound was prepared from piperidine in a similar manner to Example 96 (b), giving the compound as a clear oil (1.22 g).

MS (ES) 254 (M+H)+. $^1$H NMR (DMSO-D6) 1.35 (m, 2H), 1.45 (m, 4H), 2.22 (m, 4H), 3.38 (s, 2H), 7.20 (m, 2H), 7.43 (m, 2H).

EXAMPLE 98

2-[(Aminocarbonyl)amino]-5-{4-[(1S,4S-2-oxa-5-azabicyclo[2.2.1]hept-5-ylmethyl]phenyl}thiophene-3-carboxamide a) The title compound was prepared from (1S,4S)-5-(4-bromobenzyl)-2-oxa-5-azabicyclo[2.2.1]heptane in a similar manner to Example 93 (a), as a pale brown solid (180 mg).

LCMS (ES) 373 (M+H)+. $^1$H NMR (DMSO-D6) 1.58 (m, 1H), 1.80 (m, 1H), 2.40 (d, 1H), 2.70 (m, 1H), 3.40 (s, 1H), 3.50 (m, 1H), 3.65 (m, 2H), 3.90 (d, 1H), 4.32 (s, 1H), 6.90 (brs, 2H), 7.22 (m, 1H), 7.30 (d, 2H), 7.42 (d, 2H), 7.62 (m, 2H), 10.96 (brs, 1H).

b) (1S,4S)-5-(4-Bromobenzyl)-2-oxa-5-azabicyclo[2.2.1]heptane (1S,4S)-(+)-2-Aza-5-oxabicyclo[2.2.1]heptane hydrochloride (1.26 g), 4-bromobenzyl bromide (2.32 g) and triethylamine (3.88 ml) were stirred in dimethylformamide (30 nml) for 18 h. The mixture was partitioned between diethyl ether (60 ml) and water (60 ml) and the organic phase was washed further with water (60 ml), dried (MgSO4), concentrated in vacuo and purified by Bondelute® chromatography, eluting with 0–100% ethyl acetate/iso-hexane to give the product as an orange oil (1.91 g).

MS (ES) 267 (M)$^+$. $^1$H NMR (DMSO-D6) 1.57 (m, 1H), 1.78 (m, 1H), 2.18 (m, 1H), 2.65 (m, 1H), 3.40 (s, 1H), 3.50 (m, 1H), 3.62 (m, 2H), 3.90 (d, 1H), 4.30 (s, 1H), 7.25 (d, 2H), 7.43 (d, 2H).

EXAMPLE 99

5-{4-[4-Acetylpiperazin-1-yl)methyl]phenyl}-2-[(aminocarbonyl)amino]thiophene-3-carboxamide a) Bis-(pinacolato)diboron (1.23 g), potassium acetate (1.19 g) and dichloro[1,1'-bis-(diphenylphosphino)ferrocene]palladium(II) dichloromethane adduct (59 mg) were added to a solution of 1-acetyl-4-(4-bromobenzyl)piperazine (1.20 g) in dimethylacetamide (20 ml) whilst purging with argon and the mixture stirred at 80° C. for 16 h, then allowed to cool to ambient temperature and 2-[(aminocarbonyl)amino]-5-bromo-3-thiophenecarboxamide (213 mg), saturated aqueous sodium bicarbonate solution (5 ml) and dichloro[1,1'-bis-(diphenylphosphino)ferrocene]palladium (II) dichloromethane adduct (59 mg) were added and the mixture was stirred at 90° C. for 18 h. After cooling, the solvent was removed in vacuo and the residue was partitioned between 2M aqueous sodium hydroxide (20 ml) and dichloromethane (20 ml). The aqueous phase was then extracted further with dichloromethane (2×20 ml) and neutralised with aqueous 6M HCl. The resulting precipitate was filtered and purified using cation exchange chromatography eluting with ammonia/methanol/dichloromethane mixtures. This gave the title compound as a brown solid (17 mg).

LCMS (ES) 402 (M+H)$^+$. $^1$H NMR (DMSO-D6) 1.95 (s, 3H), 2.30 (m, 4H), 3.40 (m, 4H), 3.45 (s, 2H), 6.90 (brs, 2H), 7.25 (m, 3H), 7.42 (d, 2H), 7.62 (brs, 1H), 7.65 (s, 1H), 10.97 (brs, 1H).

b) 1-Acetyl-4-(4-bromobenzyl)piperazine

This compound was prepared from 1-acetylpiperazine in a similar manner to Example 96 (b), giving the compound as a yellow oil (1.23 g).

$^1$H NMR (DMSO-D6) 1.95 (s, 3H), 2.20–2.40 (m, 4H), 3.40 (m, 4H), 3.45 (s, 2H), 7.22 (m, 2H), 7.50 (m, 2H).

EXAMPLE 100

2-[(Aminocarbonyl)amino]-5-[4-(1,4-oxazepan-4-ylmethyl)phenyl]thiophene-3-carboxamide a) The title compound was prepared from 4-(4-bromobenzyl)-1-oxazepane in a similar manner to Example 93 (a) except that the compound was isolated by neutralisation of the basic aqueous phase with aqueous 6M HCl, followed by filtration, washing with water and drying of the resulting precipitate to give a dark brown solid (341 mg).

MS (ES) 375 (M+H)$^+$. $^1$H NMR (DMSO-D6) 1.80 (m, 2H), 2.60 (m, 4H), 3.58 (m, 4H), 3.65 (t, 2H), 6.90 (brs, 2H), 7.25 (brs, 1H), 7.30 (d, 2H), 7.45 (d, 2H), 7.65 (m, 2H), 10.97 (brs, 1H).

b) 4-(Bromobenzyl)-1,4-oxazepane

The compound was prepared from homomorpholine hydrochloride in a similar manner to Example 98 (b) to give the product as a yellow oil (4.51 g).

$^1$H NMR (DMSO-D6) 1.75 (m, 2H), 2.60 (m, 4H), 3.55 (m, 4H), 3.65 (m, 2H), 7.25 (d, 2H), 7.46 (d, 2H).

EXAMPLE 101

(1S)-2-((Aminocarbonyl)amino)-5-(4-(1-{morpholin-4-yl}ethyl)phenyl)thiophene-3-carboxamide.

a) The compound was made from (1S)-4-(1-(4-bromophenyl)ethyl)morpholine (1.6 g) in a similar manner to Example 10 (a) except that the triisopropyl borate was added after the butyl lithium solution in the first step; the solvent for the second step was dimethoxyethane/water (10:1) and solid sodium hydrogen carbonate was used and final purification was by preparative hplc to yield the product as a cream solid (530 mg).

MS (ES) 373 (M–H)$^-$. $^1$H NMR (DMSO-D6) 1.27 (d, 3H), 2.21–2.3 (m, 2H), 2.33–2.44 (m, 2H), 3.22–3.38 (m, 5H), 6.93 (brs, 2H), 7.21–7.32 (m, 3H), 7.46 (d, 2H), 7.6–7.7 (m, 2H), 10.97 (brs, 1H).

b) (1S)-4-(1-(4-Bromophenyl)ethyl)morpholine (1S)-(−)-1-(4-Bromophenyl)ethylamine (2.4 g), 2,2'-dibromodiethylether (3.25 g) and N,N-diisopropylethylamine (6 ml) were heated to 100° C. in dimethylformamide (40 ml) for 18 h, allowed to cool and partitioned between water and ethyl acetate. The organic phase was dried (MgSO$_4$), evaporated under vacuum and purified by column chromatography using a 0–40% ethyl acetate/iso-hexane gradient. The product was obtained as a yellow oil (1.91 g).

MS (ES) 270 (M+H)$^+$. $^1$H NMR (CDCl$_3$) 1.3 (d, 3H), 2.26–2.38 (m, 2H), 2.4–2.51 (m, 2H), 3.16 (q, 1H), 3.59–3.6 (m, 4H), 7.19 (d, 2H), 7.42 (d, 2H).

EXAMPLE 102

2-((Aminocarbonyl)amino)-5-(4-(1-methyl-1-{morpholin-4-yl}ethyl)phenyl)thiophene-3-carboxamide a) The compound was made from 4-({1-(4-bromophenyl)-1-methyl}ethyl)morpholine (150 mg) in a similar manner to Example 10(a) except that the triisopropyl borate was added after the butyl lithium solution in the first step, the solvent for the second step was dimethoxyethane/water (10:1) and solid sodium hydrogen carbonate was used and final purification was by preparative hplc to yield the product as a cream solid (6 mg).

MS (ES) 387 (M–H)$^-$. $^1$H NMR (DMSO-D6) 1.35 (s, 6H), 2.35–2.43 (m, 4H), 3.51–3.6 (m, 4H), 6.95 (brs, 2H), 7.31 (brs, 1H), 7.45–7.55 (m, 4H), 7.65–7.55 (m, 2H), 11.01 (s, 1H).

b) 4-({1-(4-Bromophenyl)-1-methyl}ethyl)morpholine

The compound was made in a similar manner to Example 101 (b) using 1-(4-bromophenyl)-1-methylethylamine to yield the product as a yellow gum (150 mg).

MS (ES) 284 (M+H)$^+$. $^1$H NMR (CDCl$_3$) 1.3 (s, 6H), 2.36–2.47 (m, 4H), 3.57–3.69 (m, 4H), 7.32–7.42 (m, 4H).

1-(4-Bromophenyl)-1-methylethylamine

The title compound was prepared according to *J. Org. Chem.*, 1968, 33(12), 4515.

EXAMPLE 103

2-[(Aminocarbonyl)amino]-5-[4-((4-methylpiperazin-1-yl)methyl)phenyl]thiophene-3-carboxamide a) 2-[(Aminocarbonyl)amino]-5-(4-formylphenyl)thiophene-3-carboxamide 2-[(Aminocarbonyl)amino]-5-bromo-3-thiophenecarboxamide (11.75 g) was stirred in 1,2-dimethoxyethane (500 ml) and saturated aqueous sodium bicarbonate solution (100 ml), and 4-formylphenyl boronic acid (10 g) was added. The flask was flushed with argon, and tetrakis-(triphenylphosphine)palladium(0) (5.1 g) was then added. The reaction was stirred at 90° C. for 2 h, then cooled and evaporated under reduced pressure. The residue was treated with dichloromethane (200 ml) and 2N sodium hydroxide solution (100 ml), and stirred for twenty minutes. The resulting solid was then isolated by filtration, and purified by trituration with ethanol (100 ml), giving the product as a pale green solid (5.75 g).

MS (ES) 290 (M+H)$^+$. $^1$H NMR (DMSO-D6) 7.05 (s, 2H), 7.40 (s, 1H), 7.75 (m, 3H), 7.90 (d, 2H), 8.00 (s, 1H), 9.95 (s, 1H), 11.10 (s, 1H).

b) 2-[(Aminocarbonyl)amino]-5-[4-((4-methylpiperazin-1-yl)methyl)phenyl]-thiophene-3-carboxamide 2-[(Aminocarbonyl)amino]-5-(4-formylphenyl)-3-thiophenecarboxamide (100 mg) was stirred in a mixture of 1,2-dimethoxyethane (10 ml) and N,N-dimethylacetamide (5 ml). 1-Methyl piperazine (0.16 g) was added, followed by triethyl orthoformate (5 ml) and acetic acid (0.5 ml). The reaction was stirred at 80° C. for 20 minutes, and then polymer-supported cyanoborohydride (0.45 g) was added. The reaction was stirred at 80° C. for a further 2 h, and then polymer-supported isocyanate (0.5 g) was added. The resins were removed by filtration, and the filtrate was then passed through a 5 g SCX column, washing with methanol (25 ml). The product was eluted using 1M methanolic ammonia (45 ml), and this solution was then evaporated to dryness under reduced pressure and the residue purified by chromatography on silica, eluting with dichloromethane/methanol (9:1), to give the product as an off-white solid (16 mg).

MS (ES) 374 (M+H)$^+$. $^1$H NMR (DMSO-D6) 2.15 (m, 3H), 2.30 (m, 8H), 3.45 (s, 2H), 6.90 (s, 2H), 7.30 (m, 3H), 7.50 (d, 2H), 7.65 (m, 2H), 10.95 (s, 1H).

EXAMPLE 104

2-[(Aminocarbonyl)amino]-5-[4-((2-ethoxycarbonylpiperidin-1-yl)methyl)phenyl]-thiophene-3-carboxamide The title compound was prepared in a similar manner to Example 103 (b) but from 2-(ethoxycarbonyl)piperidine (CAS Registry No. 15862-72-3).

MS (ES) 431 (M+H)$^+$. $^1$H NMR (DMSO-D6) 1.20 (t, 3H), 1.30–1.55, (m, 4H), 1.70 (m, 2H), 2.15 (m, 1H), 2.80 (m, 1H), 3.15 (m, 1H), 3.40 (d, 1H), 3.65 (d, 1H), 4.15 (q, 2H), 6.90 (s, 2H), 7.30 (m, 3H), 7.45 (d, 2H), 7.65 (s, 1H), 7.70 (s, 1H), 11.00 (s, 1H).

EXAMPLE 105

2-[(Aminocarbonyl)amino]-5-[4-((3-diethylaminocarbonylpiperidin-1-yl)methyl)phenyl]-thiophene-3-carboxamide The title compound was prepared in a similar manner to Example 103 (b) but starting from 3-([N,N-diethyl]carboxamido)piperidine.

MS (ES) 458 (M+H)$^+$. $^1$H NMR (DMSO-D6) 0.95 (t, 3H), 1.05 (t, 3H), 1.35 (m, 1H), 1.45–1.65 (m, 3H), 1.85 (m, 1H), 2.00 (t, 1H), 2.70 (m, 2H), 2.80 (m, 1H), 3.25 (m, 4H), 3.45 (q, 2H), 6.90 (s, 2H), 7.30 (m, 3H), 7.45 (d, 2H), 7.65 (s, 1H), 7.70 (s, 1H), 11.00 (s, 1H).

EXAMPLE 106

2-[(Aminocarbonyl)amino]-5-[4-((3-hydroxypyrrolidine-1-yl)methyl)phenyl]thiophene-3-carboxamide 2-[(Aminocarbonyl)amino]-5-(4-formylphenyl)-3-thiophenecarboxamide (100 mg) was stirred in a mixture of 1,2-dimethoxyethane (10 ml) and N,N-dimethylacetamide (5 ml). 3-pyrrolidinol (0.15 g) was added, followed by trimethyl orthoformate (5 ml) and acetic acid (0.5 ml). The reaction was stirred at 80° C. for 20 minutes, and then polymer-supported cyanoborohydride (0.45 g) was added. The reaction was stirred at 80° C. for a further 2 h, and then polymer-supported benzaldehyde (0.5 g) was added. The resins were removed by filtration, and the filtrate was then passed through a 5 g SCX column, washing with methanol (25 ml). The product was eluted using 1M methanolic ammonia (45 ml), and this solution was then evaporated to dryness under reduced pressure. Purification by chromatography on silica, eluting with dichloromethane/methanol (9:1), gave the product as an off-white solid (30 mg).

MS (ES) 361 (M+H)$^+$. $^1$H NMR (DMSO-D6) 1.55 (m, 1H), 2.05 (m, 1H), 2.35 (m, 1H), 2.45 (m, 1H), 2.60 (m, 1H), 2.70 (m, 1H), 3.55 (m, 2H), 4.20 (m, 1H), 4.65 (m 1H), 6.90 (s, 2H), 7.30 (m, 3H), 7.50 (d, 2H), 7.70 (m, 2H), 10.95 (s, 1H).

EXAMPLE 107

2-[(Aminocarbonyl)amino]-5-[4-({(2-hydroxyethyl)piperazin-1-yl}methyl)phenyl]-thiophene-3-carboxamide The title compound was prepared in a similar manner to Example 106 but using 4-(2-hydroxyethyl)piperazine (CAS Registry No. 103-76-4).

MS (ES) 404 (M+H)$^+$. $^1$H NMR (DMSO-D6) 2.25–2.60 (m, 10H), 3.50 (, 4H), 4.35 (m, 1H), 6.90 (s, 2H), 7.30 (m, 3H), 7.45 (d, 2H), 7.70 (m, 2H), 10.95 (s, 1H).

EXAMPLE 108

2-[(Aminocarbonyl)amino]-4-methyl-5-{4-[4-morpholino]methylphenyl}-3-thiophenecarboxamide a) The title compound was prepared in a similar manner to Example 9 (e) but using 1-bromo-4-(4-morpholino)methylbenzene and 2-[(aminocarbonyl)amino]-5-bromo-4-methyl-3-thiophenecarboxamide. The crude solid was purified by cation exchange chromatography eluting with ammonia/dichloromethane/methanol mixtures.

MS (ES) 375 (M+H)$^+$. $^1$H NMR (DMSO-D6) 2.25 (s, 3H), 2.3 (s, 4H), 3.5 (s, 2H), 3.55 (m, 4H), 6.8 (s, 2H), 7.2–7.5 (m, 6H), 10.05 (s, 1H).

b) 2-[(Aminocarbonyl)amino]-4-methyl-3-thiophenecarboxamide

Prepared in a similar manner to Example 9 (b) except that tetrahydrofuran was used as solvent and the product was obtained by trituration with methanol.

MS (ES) 198 (M–H)$^-$, 200 (M+H)$^+$. $^1$H NMR (DMSO-D6) 2.2 (s, 3H), 6.35 (s, 1H), 6.65 (s, 2H), 6.8–8.3 (brs, 2H), 10.3 (s, 1H).

c) 2-[(Aminocarbonyl)amino]-5-bromo-4-methyl-3-thiophenecarboxamide

Prepared in a similar manner to Example 9 (c) except that the precipitated product was filtered off from the reaction and triturated with methanol.

MS (ES) 276, 278 (M−H)⁻, 278, 280 (M+H)⁺. ¹H NMR (DMSO-D6) 2.1 (s, 3H), 6.8 (s, 2H), 7.0–7.5 (brs, 2H), 10.15 (s, 1H).

EXAMPLE 109

2-[(Aminocarbonyl)amino]-5-[4-((4-h dihydroxypiperidin 1-yl)methyl)phenyl]thiophene-3-carboxamide a) 1-(4-Bromobenzyl)piperidin-4-ol 4-Bromobenzylbromide (3 g) was stirred with 4-hydroxypiperidine (1.21 g) and potassium carbonate (1.99 g) in dimethylacetamide (15 ml) at 50° C. for 3 h. The reaction mixture was then allowed to cool, poured into water (80 ml) and extracted with ethyl acetate (3×50 ml). The combined extracts were washed with water, dried (MgSO₄), filtered and evaporated. The residue was purified by column chromatography, eluting with a gradient of 0–3% methanol in dichloromethane, to afford the product as a viscous, colourless oil (2.02 g).

MS (ES) 270 (M+H)⁺. ¹H NMR (CDCl₃) 1.50–1.67 (m, 2H), 1.8–1.95 (m, 2H), 2.07–2.20 (m, 2H), 2.66–2.77 (m, 2H), 3.44 (s, 2H), 3.65–3.77 (m, 1H), 7.19 (d, 2H), 7.43 (d, 2H).

b) 2-[(Aminocarbonyl)amino]-5-[4-((4-hydroxypiperidin-1-yl)methyl)phenyl]thiophene-3-carboxamide The title compound was prepared from 1-(4-bromobenzyl)piperidin-4-ol in a similar manner to Example 38 (a), but was purified by preparative HPLC.

MS (ES) 375 (M+H)⁺. ¹H NMR (DMSO-D6) 1.30–1.45 (m, 2H), 1.60–1.75 (m, 2H), 1.94–2.08 (m, 2H), 2.58–2.70 (m, 2H), 3.30–3.50 (m, 2H), 4.49 (d, 1H), 6.92 (brs, 2H), 7.26 (d, 2H), 7.26 (brs, 1H), 7.44 (d, 2H), 7.65 (brs, 1H), 7.66 (s, 1H), 10.97 (s, 1H).

EXAMPLE 110

2-[(Aminocarbonyl)amino]-5-(2-piperazin-1-yl)phenyl)thiophene-3-carboxamide a) 1-(2-Bromophenyl)-4-(t-butyloxycarbonyl)piperazine 1,2-Dibromobenzene (2.56 ml) was stirred in toluene (100 ml) and the solution was purged with argon. 1-t-Butyloxycarbonylpiperazine (4.74 g), sodium t-butoxide (2.85 g), BINAP (95 mg) and palladium acetate (50 mg) were added. The reaction mixture was stirred at 80° C. under argon for 16 h, then allowed to cool. Insoluble material was removed by filtration and washed with toluene. The solvent was evaporated and the residue was purified by column chromatography, eluting with hexane, to give the product as a pale yellow oil (1.85 g).

MS (ES) 341 (M+H)⁺. ¹H NMR (CDCl₃) 1.50 (s, 9H), 2.90–3.04 (m, 4H), 3.55–3.65 (m, 4H), 6.92 (td, 1H), 7.01 (dd, 1H), 7.21–7.29 (m, 1H), 7.56 (dd, 1H).

b) 2-[(Aminocarbonyl)amino]-5-[2-(4-t-butyloxycarbonylpiperazin-1-yl)phenyl]thiophene-3-carboxamide The title compound was prepared from 1-(2-bromophenyl)-4-(t-butyloxycarbonyl)-piperazine in a similar manner to Example 9 (e), except that on work-up the reaction mixture was evaporated and the residue taken up in dichloromethane and 2M aqueous sodium hydroxide. The aqueous phase was washed with a further portion of dichloromethane and the combined organic layers were evaporated in vacuo then purified by cation exchange chromatography, eluting with 5–10% methanol in dichloromethane.

Fractions containing product were evaporated, the residue was triturated with ether and the solid product collected by filtration.

MS (ES) 446 (M+H)⁺. ¹H NMR (DMSO-D6) 1.40 (s, 9H), 2.72–2.83 (m, 4H), 3.47–3.57 (m, 4H), 6.80 (brs, 2H), 7.07–7.25 (m, 4H), 7.56 (d, 1H), 7.65 (brs, 1H), 7.75 (s, 1H), 10.90 (s, 1H).

c) 2-[(Aminocarbonyl)amino]-5-[2-(piperazin-1-yl)phenyl]thiophene-3-carboxamide

2-[(Aminocarbonyl)amino]-5-[2-(4-t-butyloxycarbonylpiperazin-1-yl)phenyl]thiophene-3-carboxamide (64 mg) was stirred in dichloromethane (4 ml). Trifluoroacetic acid (1 ml) was added and the solution was stirred at room temperature for 1 h. The volatile materials were removed in vacuo; the residue was diluted with water (2 ml) and basified with a few drops of aqueous ammonia. The precipitated product was collected by filtration and washed with water. The gummy solid obtained was dissolved in methanol, the solvent was evaporated and the residue triturated with a mixture of methanol and ether and then filtered to give the product as an off-white solid (20 mg).

MS (ES) 346 (M+H)⁺. ¹H NMR (DMSO-D6, 400 MHz) 2.75–2.85 (m, 4H), 2.95–3.05 (m, 4H), 6.80 (brs, 2H), 7.08–7.30 (m, 4H), 7.55 (d, 1H), 7.62 (brs, 1H), 7.72 (s, 1H), 10.91 (s, 1H).

EXAMPLE 111

2-[(Aminocarbonyl)amino]-5-[2-(4-methylpiperazin-1-yl)phenyl]thiophene-3-carboxamide a) 1-(2-Bromophenyl)-4-methylpiperazine The title compound was prepared from dibromobenzene and 1-methylpiperazine in a similar manner to Example 110 (a).

MS (ES) 255 (M+H)⁺. ¹H NMR (CDCl₃) 2.35 (s, 3H), 2.50–2.70 (m, 4H), 2.98–3.15 (m, 4H), 6.90 (td, 1H), 7.05 (dd, 1H), 7.26 (td, 1H), 7.55 (dd, 1H).

b) 2-[(Aminocarbonyl)amino]-5-[2-(4-methylpiperazin-1-yl)phenyl]thiophene-3-carboxamide The title compound was prepared from 1-(2-bromophenyl)-4-methylpiperazine in a similar manner to Example 9 (e), except that the product was purified by cation exchange chromatography, eluting with 0–10% of 2M ammonia/methanol in dichloromethane. Fractions containing product were evaporated, triturated with ether and the product was collected by filtration.

MS (ES) 360 (M+H)⁺. ¹H NMR (DMSO-D6) 2.20 (s, 3H), 2.45–2.58 (m, 4H), 3.30 (s, 4H), 6.81 (brs, 2H), 7.05–7.24 (m, 4H), 7.53 (d, 1H), 7.62 (brs, 1H), 7.70 (s, 1H), 10.90 (s, 1H).

EXAMPLE 112

2-[(Aminocarbonyl)amino]-5-{2-[3-methylamino)pyrrolidin-1-yl]phenyl}thiophene-3-carboxamide a) 1-(2-Bromophenyl)-[3-(N-t-butyloxycarbonyl-N-methylamino)]pyrrolidine The title compound was prepared from dibromobenzene and 3-(N-t-butyloxycarbonyl-N-methylamino)pyrrolidine as for Example 110 (a).

MS (ES) 355 (M+H)⁺. ¹H NMR (CDCl₃) 1.48 (s, 9H), 1.90–2.05 (m, 1H), 2.15–2.30 (m, 1H), 2.93 (s, 3H), 3.10–3.22 (m, 2H), 3.40–3.50 (m, 1H), 3.55 (dd, 1H), 4.80–4.95 (brm, 1H), 6.83 (td, 1H), 6.95 (dd, 1H), 7.22 (td, 1H), 7.52 (dd, 1H).

b) 2-[Aminocarbonyl)amino]-5-{2-[3-(N-t-butyloxycarbonyl-N-methylamino)pyrrolidin-1-yl]phenyl}thiophene-3-carboxamide The title compound was prepared from 1-(2-bromophenyl)-[3-(N-t-butyloxycarbonyl-N-methylamino)]pyrrolidine in a similar manner to Example 9 (e), except that on work-up the reaction mixture was evaporated to dryness, taken up in dichloromethane and 2M aqueous sodium hydroxide and the layers were separated. The organic phase was concentrated in vacuo and purified by cation exchange chromatography, eluting with a gradient of 0–4% 2M ammonia/methanol in dichloromethane. Fractions containing product were evaporated and the product triturated with ether and collected by filtration.

MS (ES) 460 (M+H)$^+$. $^1$H NMR (DMSO-D6) 1.38 (s, 9H), 1.79–2.09 (m, 2H), 2.70–3.18 (m, 4H), 2.75 (s, 3H), 4.65–4.80 (brm, 1H), 6.85 (brs, 2H), 6.95 (t, 1H), 7.05 (d, 1H), 7.13–7.24 (m, 2H), 7.34 (d, 1H), 7.46 (s, 1H), 7.60 (brs, 1H), 10.94 (s, 1H).

c) 2-[(Aminocarbonyl)amino]-5-{2-[3-methylamino)pyrrolidin-1-yl]phenyl}thiophene-3-carboxamide 2-[Aminocarbonyl)amino]-5-{2-[3-(N-t-butyloxycarbonyl-N-methylamino)pyrrolidin-1-yl]phenyl}thiophene-3-carboxamide (187 mg) was stirred in dichloromethane (2 ml). Trifluoroacetic acid (2 ml) was added dropwise and stirring continued at room temperature for 10 h. The volatile materials were evaporated in vacuo and the residue purified by cation exchange chromatography, eluting with a gradient of 0–10% 2M ammonia/methanol in dichloromethane. Fractions containing product were evaporated, triturated with ether and the product collected by filtration (88 mg).

MS (ES) 360 (M+H)$^+$. $^1$H NMR (DMSO-D6) 1.55–1.70 (m 1H), 1.95–2.10 (m, 1H), 2.21 (s, 3H), 2.74–23.10 (m, 4H), 3.95–4.10 (brm, 1H), 6.83 (brs, 2H), 6.90 (t, 1H), 6.99 (d, 1H), 7.10–7.22 (m, 2H), 7.30 (d, 1H), 7.42 (s, 1H), 7.60 (brs, 1H), 10.93 (brs, 1H).

EXAMPLE 113

2-[(Aminocarbonyl)amino]-5-[4-(cyclopentyloxy)-2-(2-piperidin-1-yl1 ethoxy)phenyl]thiophene-3-carboxamide a) The title compound was prepared from 1-{2-[2-bromo-5-(cyclopentyloxy)phenoxy]-ethyl}piperidine in a similar manner to Example 43 except that the residue was extracted with hot ethyl acetate (2×100 ml), evaporated to give a gum which was purified by column chromatography eluting with methanol/dichloromethane/0.88 ammonia 1/9/0.01. Further column chromatography eluting with a gradient using water/acetonitrile/trifluoroacetic acid gave on triturating with ammonia the product as a light brown solid (20 mg).

MS (ES) 473 (M+H)$^+$. $^1$H NMR (DMSO-D6) 1.34 (m, 2H), 1.45 (m, 4H), 1.57 (m, 2H), 1.69 (m, 4H), 1.90 (m, 2H), 2.44 (m, 4H), 2.74 (t, 2H), 4.11 (t, 2H), 4.84 (m, 1H), 6.52 (d, 1H), 6.58 (d, 1H), 6.77 (brs, 2H), 7.15 (brs, 1H), 7.42, (d, 1H), 7.54 (s+brs, 2H), 10.86 (s, 1H).

b) 1-[2-[2-Bromo-5-(cyclopentyloxy)phenoxy]ethyl)piperidine

4-Bromo-3-(2-{piperidin-1-yl}ethoxy)phenol (1.5 g), bromocyclopentane (0.59 ml) and anhydrous potassium carbonate (1.04 g) were stirred and heated at 80° C. in dimethylformamide for 18 h. The mixture was partitioned between ethyl acetate (100 ml) and water (70 ml). The aqueous was extracted further with ethyl acetate (100 ml) and the combined organics were washed with 2N sodium hydroxide solution (50 ml), water (50 ml), brine (50 ml), dried (MgSO$_4$) and evaporated to give the product as an oil (1.5 g).

MS (ES) 368 (M+H)$^+$. $^1$H NMR (CDCl$_3$) 1.38 (m, 2H), 1.54 (m, 4H), 1.68–1.86 (m, 8H), 2.50 (m, 4H), 2.77 (t, 2H), 4.05 (t, 2H), 4.63 (m, 1H), 6.29 (d, 1H), 6.37 (d, 1H), 7.29(d, 1H).

c) 4-Bromo-3-(2-{piperidin-1-yl}ethoxy)phenol

4-Bromo-3-(2-{piperidin-1-yl}ethoxy)phenyl 4-methylbenzenesulfonate (24.2 g), potassium hydroxide (16.1 g), water (96 ml) and ethanol (860 ml) were heated on the steam bath for 2 h. The pH was adjusted to 4 with concentrated hydrochloric acid, then to pH 7 with solid sodium bicarbonate. After evaporation to near dryness, water (200 ml) was added and the mixture was extracted with ethyl acetate (3×150 ml). The organic phase was washed with water, brine, dried (MgSO$_4$) and evaporated to give an oil (16.4 g).

MS (ES) 300 (M+H)$^+$. $^1$H NMR (CDCl$_3$) 1.47 (m, 2H), 1.64 (m, 4H), 2.66(m, 4H), 2.87 (t, 2H), 4.06 (t, 2H), 6.31 (m, 2H), 7.25 (d, 1H).

d) 4-Bromo-3-(2-{piperidin-1-yl}ethoxy)phenyl 4-methylbenzenesulfonate

4-Bromo-3-hydroxyphenyl 4-methylbenzenesulfonate (17.6 g), potassium carbonate (7.32 g), 1-(2 chloroethyl) piperidine hydrochloride (9.2 g) and acetone (300 ml) were stirred at reflux for 3 h, the reaction mixture filtered and evaporated to give the product as light brown foam (24.2 g).

MS (ES) 454 (M+H)$^+$. $^1$H NMR (CDCl$_3$) 1.38 (m, 2H), 1.53 (m, 4H), 2.38 (s, 3H), 2.45 (t, 4H), 2.71 (t, 2H), 3.94 (t, 2H), 6.35 (d, 1H), 6.51 (d, 1H), 7.25 (d, 2H), 7.32 (d, 1H), 7.64 (d, 2H). The structure was confirmed by n.O.e. experiments.

EXAMPLE 114

2-[(Aminocarbonyl)amino]-5-[2-(2-{piperidin-1-yl}ethoxy)-4-pyrrolidin-1-ylphenyl]thiophene-3-carboxamide a) The title compound was prepared from 1-[2-(2-bromo-5-pyrrolidin-1-ylphenoxy)ethyl]piperidine in a similar manner to Example 113 (a) except that the product was obtained by triturating with ether to give a light brown solid (20 mg).

MS (ES) 458 (M+H)$^+$. $^1$H NMR (DMSO-D6) 1.36 (m, 2H), 1.48 (m, 4H), 1.93 (m, 4H), 2.45 (m, 4H), 2.77 (t, 2H), 3.26 (m, 4H), 4.12 (t, 2H), 6.16 (m, 2H), 6.73 (brs, 2H), 7.12 (brs, 1H), 7.31 (d, 1H), 7.41 (s, 1H), 7.50 (brs, 1H), 10.82 (s, 1H).

b) 1-[2-(2-Bromo-5-pyrrolidin-1-ylphenoxy)ethyl]piperidine

4-Bromo-3-(2-{piperidin-1-yl}ethoxy)aniline (2.99 g), 1,4-dibromobutane (1.2 ml), diisopropylethylamine (4.18 ml) and toluene (15 ml) were stirred and heated at 110° C. for 18 h. When cool, water (20 ml) was added, and the mixture was extracted with ethyl acetate (2×30 ml). The combined organic phase was washed with water, brine, dried (MgSO$_4$) and evaporated to give the product as an orange-brown oil (2.25 g).

MS (ES) 353 (M+H)$^+$. $^1$H NMR (CDCl$_3$) 1.37 (m, 2H), 1.53 (m, 4H), 1.92 (m, 4H), 2.48 (t, 4H), 2.76 (t, 2H), 3.17 (t, 4H), 4.07 (t, 2H), 5.97 (dd, 1H), 6.03 (d, 1H), 7.19 (d, 1H).

c) 4-Bromo-3-(2-{piperidin-1-yl}ethoxy)aniline

N-[4-Bromo-3-(2-{piperidin-1-yl}ethoxy)phenyl]acetamide (17.48 g), 35% hydrochloric acid (100 ml) and water (100 ml) were heated at 95° C. for 2 h, evaporated to near dryness, water (100 ml) added and the pH adjusted to 8 with sodium carbonate. Extraction with dichloromethane (3×200 ml), the combined organic phase washed with water, brine, dried (MgSO$_4$) and evaporated to give the product as a solid (13.64 g).

MS (ES) 299 (M+1H). $^1$H NMR (CDCl$_3$) 1.38 (m, 2H), 1.53 (m, 4H), 2.48(m, 4H), 2.75 (t, 2H), 3.60 (brs, 2H), 4.02 (t, 2H), 6.10 (dd, 1H), 6.18 (d, 1H), 7.16 (d, 1H).

d) N-[4-Bromo-3-(2-{piperidin-1-yl}ethoxyphenyl]acetamide

N-(4-Bromo-3-hydroxyphenyl)acetamide (19.4 g), anhydrous potassium carbonate (25.6 g), 1-(2 chloroethyl)piperidine hydrochloride (15.78 g) and acetone (400 ml) were heated at reflux for 18 h, filtered and evaporated to dryness to give the product as a solid (17.48 g).

MS (ES) 341 (M+H)$^+$. $^1$H NMR (DMSO-D6) 1.36 (q, 2H), 1.48 (m, 4H), 2.02 (s, 3H), 2.45 (m, 4H), 2.67 (t, 2H), 4.04 (t, 2H), 7.07 (d, 1H), 7.43 (s+d, 2H), 10.02(s, 1H).

EXAMPLE 115

2-[(Aminocarbonyl)amino]-5-[4-piperidin-1-yl-2-(2-{piperidin-1-yl}ethoxyphenyl]thiophene-3-carboxamide a) The title compound was prepared from 1-[4-bromo-3-(2-{piperidin-1-yl}ethoxy)phenyl]piperidine in a similar manner to Example 114 (a) to give the product as a solid (20 mg).

MS (ES) 472 (M+H)$^+$. $^1$H NMR (DMSO-D6) 1.35 (m, 2H), 1.46 (m, 4H), 1.59 (m, 6H), 2.44 (m, 4H), 2.75 (t, 2H), 3.17 (m, 4H), 4.12 (t, 2H), 6.53 (dd, 1H), 6.57 (s, 1H), 6.75 (brs, 2H), 7.12 (brs, 1H), 7.36 (d, 1H), 7.49 (s, 1H), 7.51 (brs, 1H), 10.84 (s, 1H).

b) 1-[4-Bromo-3-(2-piperidin-1-ylethoxy)phenyl]piperidine

The title compound was prepared as in Example 114 (b) using 1,5-dibromopentane except that the oil obtained was purified by column chromatography eluting with methanol/dichloromethane 1:9 to give the product as an oil (2.1 g).

MS (ES) 367 (M+H)$^+$. $^1$H NMR (CDCl$_3$) 1.43 (m, 2H), 1.52 (m, 2H), 1.62 (m, 8H), 2.62 (m, 4H), 2.87 (t, 2H), 3.06 (m, 4H), 4.14 (t, 2H), 6.35 (dd, 1H), 6.43 (s, 1H), 7.24 (d, 1H).

EXAMPLE 116

2-[(Aminocarbonyl)amino]-5-[4-(morpholin-4-ylmethyl)-2-(2-{piperidin-1-yl}ethoxy)phenyl]thiophene-3-carboxamide a) The title compound was prepared from 4-[4-bromo-3-(2-{piperidin-1-yl}ethoxy)-benzyl]morpholine (1.95 g) in a similar manner to Example 43 to give a fawn solid (60 mg).

MS (ES) 488 (M+H)$^+$. $^1$H NMR (DMSO-D6) 1.36 (m, 2H), 1.48 (m, 4H), 2.33 (m, 4H), 2.42 (m, 4H), 2.63 (t, 2H), 3.43 (s, 2H), 3.56 (m, 4H), 4.06 (t, 2H), 6.85 (dd+brs, 3H), 7.02 (d, 1H), 7.21 (s+brs, 2H), 7.25 (d, 1H), 7.56 (brs, 1H), 10.91 (s, 1H).

b) 4-[4-Bromo-3-(2-piperidin-1-ylethoxy)benzyl]morpholine

The title compound was prepared from 2-bromo-5-(morpholin-4-ylmethyl)phenol (4.75 g) in a similar manner to Example 114 (d) except that the product was purified by column chromatography eluting with dichloromethane and 1:9 methanol/dichloromethane to give an oil (2.28 g).

MS (ES) 383 (M+H)$^+$. $^1$H NMR (CDCl$_3$) 1.37 (m, 2H), 1.54 (m, 4H), 2.44 (m, 8H), 2.68 (t, 2H), 3.47 (s, 2H), 3.65 (m, 4H), 4.01 (t, 2H), 6.61 (dd, 1H), 7.00 (d, 1H), 7.33 (d, 1H).

c) 2-Bromo-5-(morpholin-4-ylmethyl)phenol 3-(Morpholin-4-ylmethyl)phenol (9.65 g) in glacial acetic acid (60 ml) was treated over 2 h with bromine (2.88 ml) in acetic acid (8 ml), evaporated to near dryness, water (100 ml) added and basified with 0.880 ammonia, extracted with ethyl acetate, washed with water, brine, dried (MgSO$_4$) and evaporated to dryness to give an oil, which was purified by column chromatography eluting with 1:1 ether/isohexane to give the desired product as an oil (4.75 g).

MS (ES) 272 (M+H)$^+$. $^1$H NMR (CDCl$_3$) 2.47 (t, 4H), 3.47 (s, 2H), 3.67 (t, 4H), 6.54 (dd, 1H), 6.94 (d, 1H), 7.30 (d, 1H).

EXAMPLE 117

2-[(Aminocarbonyl)amino]-5-[4-(2-methoxyethoxy)-2-(2-piperidin-1-ylethoxy)phenyl]thiophene-3-carboxamide a) The title compound was prepared in a similar manner to Example 113 (a) from 1-{2-[2-bromo-5-(2-methoxyethoxy)phenoxy]ethyl}piperidine (1.35 g) except that the residue was purified by reversed phase chromatography eluting with water/acetonitrile/trifluoroacetic acid, then further column chromatography with methanol/dichloromethane/0.88 ammonia to give the product as a fawn solid (80 mg).

MS (ES) 463 (M+H)$^+$. $^1$H NMR (DMSO-D6) 1.35 (m, 2H), 1.47 (m, 4H), 2.45 (m, 4H), 2.77 (t, 2H); 3.30 (s, 3H), 3.64(m, 2H), 4.12 (m, 4H), 6.57 (dd, 1H), 6.66 (d, 1H), 6.79 (brs, 2H), 7.16 (brs, 1H), 7.44 (d, 1H), 7.55 (s+brs, 2H), 10.86 (s, 1H).

b) 1-{2-[2-Bromo-5-(2-methoxyethoxy)phenoxy]ethyl}piperidine

This was prepared in a similar manner to Example 113 (b) using 1-bromo-2-methoxyethane (0.52 ml) to give the product as an oil (1.35 g).

MS (ES) 358 (M+H)$^+$. $^1$H NMR (CDCl$_3$) 1.31 (m, 2H), 1.53 (m, 4H), 2.48 (t, 4H), 2.76 (t, 2H), 3.37 (s, 3H), 3.66 (t, 2H), 4.03 (dt, 4H), 6.33 (d, 1H), 6.47 (s, 1H), 7.30 (d, 1H).

EXAMPLE 118

2-[(Aminocarbonyl)amino]-5-[4-morpholin-4-yl-2-(2-piperidin-1-ylethoxy)phenyl]thiophene-3-carboxamide a) The title compound was prepared from 4-[4-bromo-3-(2-piperidin-1-ylethoxy)phenyl]morpholine (1.85 g) in a similar manner to Example 43 except that the product was purified by column chromatography eluting with methanol/dichloro-methane/0.880 ammonia 95:5:0.1 to give the product as a fawn solid (146 mg).

MS (ES) 474 (M+H)$^+$. $^1$H NMR (DMSO-D6) 1.35 (m, 2H), 1.46 (m, 4H), 2.44 (m, 4H), 2.75 (t, 2H), 3.14 (m, 4H), 3.71 (m, 4H), 4.13 (t, 2H), 6.55 (dd, 1H), 6.59 (d, 1H), 6.76 (brs, 2H), 7.15 (brs, 1H), 7.40 (d, 1H), 7.53 (brs+s, 2H), 10.85 (s, 1H).

b) 4-[4-Bromo-3-(2-piperidin-1-ylethoxy)phenyl]morpholine

The title compound was prepared in a similar manner to Example 114 (b) but using 1-bromo-2-(2-bromoethoxy) ethane (1.4 ml) to give the product as an oil (2.30 g).

MS (ES) 369 (M+H)⁺. ¹H NMR (CDCl₃) 1.38 (m, 2H), 1.54 (m, 4H), 2.50 (t, 4H), 2.77 (t, 2H), 3.05 (t, 4H), 3.77 (t, 4H), 4.07 (t, 2H), 6.31 (dd, 1H), 6.40 (d, 1H), 7.29 (d, 1H).

EXAMPLE 119

2-[(Aminocarbonyl)amino]-5-[2-(2-hydroxyethoxy)phenl thiophene-3-carboxamide

The title compound was prepared from [2-(2-bromophenoxy)ethoxy]-(tert-butyl)dimethylsilane (1.68 g) in a similar manner to Example 43 except that the dichloromethane extract was purified by column chromatography eluting with dichloromethane, then 1:9 methanol/dichloromethane, then further preparative HPLC to give the product as a solid on triturating with ether (142 mg).

MS (ES) 322 (M+H)⁺. ¹H NMR (DMSO-D6) 3.84 (q, 2H), 4.13 (t, 2H), 4.82 (t, 1H), 6.86 (brs, 2H), 7.00 (t, 1H), 7.12 (d, 1H), 7.22 (t+brs, 2H), 7.57 (d+brs, 2H), 7.80 (s, 1H), 10.95 (s, 1H).

b) [2-(2-Bromophenoxy)ethoxy](tert-butyl)dimethylsilane

2-Bromophenol (1.88 g), anhydrous potassium carbonate (1.51 g), (2-bromoethoxy)-(tert-butyl)dimethylsilane (2.61 g) and dimethylformamide (30 ml) were heated for 20 h at 90° C., cooled, poured into water (100 ml), extracted with ethyl acetate, the organic phase washed with water, brine, dried (MgSO₄) and evaporated to dryness. The residue was purified by column chromatography eluting with 1:9 ether/isohexane to give the product as a crystalline solid (1.68 g).

¹H NMR (CDCl₃) 0.04 (s, 6H), 0.84 (s, 9H), 3.95 (t, 2H), 4.03 (t, 2H), 6.75 (t, 1H), 6.86 (d, 1H), 7.17 (t, 1H), 7.45 (d, 1H).

EXAMPLE 120

(3R)-2-[(Aminocarbonyl)amino]-5-{2-tetrahydrofuran-3-yloxy]phenyl}-3-thiophenecarboxamide a) The title compound was prepared in a similar manner to Example 9 (e) but using R-3-(2-bromophenoxy)tetrahydrofuran.

MS (ES) 346 (M–H)⁻, 348 (M+H)⁺. ¹H NMR (DMSO-D6) 2.1–2.3 (m, 2H), 3.7–4.0 (m, 4H), 5.1 (m, 1H), 6.8 (brs, 2H), 6.9–7.1 (m, 2H), 7.2 (m, 2H), 7.6 (m, 2H), 7.7 (s, 1H), 10.9 (s, 1H).

b) R-3-(2-Bromophenoxy)tetrahydrofuran.

Di-isopropylazodicarboxylate (5.5 g) was added dropwise at 0–5° C. to a stirred solution of 2-bromophenol (4.0 g), triphenylphosphine (7.1 g) and S-3-hydroxytetrahydrofuran (2.4 g) in dry tetrahydrofuran (60 ml). The mixture was stirred for 18 h at 20° C., the solvent was evaporated, and the residue stirred in ether (150 ml) for 2 h, giving a white precipitate. This was removed by filtration and the mother liquors were washed with 2N sodium hydroxide solution, water, brine, evaporated, and the residue was purified by column chromatography on silica eluting with 10 to 50% ethyl acetate in isohexane, giving the title compound as a colourless oil (4.5 g).

MS (EI) 242 (M⁺). ¹H NMR (CDCl₃) 2.1–2.3 (m, 2H), 3.9–4.1 (m, 4H), 4.95 (m, 1H), 6.8–6.9 (m, 2H), 7.2–7.3 (m, 1H), 7.5–7.6 (d, 1H).

EXAMPLE 121

(3S)-2-[(Aminocarbonyl)amino]-{5-2-[tetrahydrofuran-3-yloxy]phenyl}-3-thiophenecarboxamide a) The title compound was prepared in a similar manner to Example 9 (e) but using S-3-(2-bromophenoxy)tetrahydrofuran.

MS (ES) 346 (M–H)⁻, 348 (M+H)⁺. ¹H NMR (DMSO-D6) 2.1–2.3 (m, 2H), 3.7–4.0 (m, 4H), 5.1 (m, 1H), 6.8 (rs, 2H), 6.9–7.1 (m, 2H), 7.2 (m, 2H), 7.6 (m, 2H), 7.7 (s, 1H), 10.9 (s, 1H).

b) S-3-(2-Bromophenoxy)tetrahydrofuran

The compound was prepared from R-3-hydroxytetrahydrofuran in a similar manner to Example 120 (b).

MS (EI) 242, 244 (M⁺). ¹H NMR (CDCl₃) 2.1–2.3 (m, 2H), 3.9–4.1 (m, 4H), 4.95 (m, 1H), 6.8–6.9 (m, 2H), 7.2–7.3 (m, 1H), 7.5–7.6 (d, 1H).

EXAMPLE 122

2-[(Aminocarbonyl)amino]-5-{2-[(tetrahydropyran-4-yloxy]phenyl}-3-thiophenecarboxamide a) The title compound was prepared in a similar manner to Example 9 (e) but using 4-(2-bromophenoxy)-tetrahydropyran.

MS (ES) 360 (M–H)⁻, 362 (M+H)⁺. ¹H NMR (DMSO-D6) 1.65–1.8 (m, 2H), 1.9–2.05 (m, 2H) 3.4–3.5 (m, 2H) 3.85–3.95 (m, 2H), 4.7 (m, 1H), 6.8 (brs, 2H), 6.95 (t, 1H), 7.1–7.2 (m, 3H), 7.6–7.65 (m, 2H), 7.7 (s, 1H), 10.9 (s, 1H).

b) 4-(2-Bromophenoxy)tetrahydropyran

The compound was prepared from 4-hydroxytetrahydropyran in a similar manner to Example 120 (b).

MS (EI) 256, 258(M⁺). ¹H NMR (CDCl₃) 1.8–1.9 (m, 2H), 1.95–2.1 (m, 2H), 3.5–3.7 (m, 2H), 3.95–4.05 (m, 2H), 4.5–4.6 (m, 1H), 6.85 (t, 1H), 6.9 (d, 1H), 7.2 (d, 1H), 7.55 (d, 1H).

EXAMPLE 123

2-[(Aminocarbonyl)amino]-5-{2-[cyclopropylmethoxy]phenyl}-3-thiophenecarboxamide a) The title compound was prepared in a similar manner to Example 9 (e) but using 1-bromo-2-(cyclopropylmethoxy)benzene.

MS (ES) 330 (M–H)⁻, 332 (M+H)⁺. ¹H NMR (DMSO-D6) 0.0, (d, 2H), 0.1 (d, 2H), 0.9 (m, 1H), 3.55 (d, 2H), 6.4 (brs, 2H), 6.6 (t, 1H), 6.65 (d, 1H), 6.7–6.9 (m, 2H), 7.2 (m, 2H), 7.4 (s, 1H), 10.55 (s, 1H).

b) 1-Bromo-2-(cyclopropylmethoxy)benzene

Prepared from cyclopropylmethyl bromide and 2-bromophenol by the method of Example 42 (b) except that the reaction mixture was stirred at 75° C. for 4 h. This gave the product as a colourless oil.

MS (EI) 226, 228 (M⁺). ¹H NMR (CDCl₃) 0.35–0.4 (m, 2H), 0.6–0.7 (m, 2H), 1.3 (m, 1H), 3.9 (d, 2H), 6.8 (t, 1H), 6.9 (t, 1H), 7.1 (d, 1H), 7.55 (d, 1H).

EXAMPLE 124

2-[(Aminocarbonyl)amino]-5-{2-[cyclopentyloxy]phenyl}-3-thiophenecarboxamide a) The title compound was prepared in a similar manner to Example 9(e) but using 1-bromo-2-(cyclopentyloxy)benzene.
MS (ES) 344 (M−H), 346 (M+H)+. $^1$H NMR (DMSO-D6) 1.5–1.7 (m, 2H), 1.8–1.95 (m, 6H), 4.95 (m, 1H), 6.8 (s, 2H), 6.9 (t, 1H), 7.0 (d, 1H), 7.3 (m, 2H), 7.6 (m, 2H), 7.7 (s, 1H), 10.9 (s, 1H).

b) 1-Bromo-2-(cyclopentyloxy)benzene
This was prepared from cyclopentanol in a similar manner to Example 120 (b).
MS (EI) 240, 242 (M+). $^1$H NMR (CDCl$_3$) 1.6–1.7 (m, 2H), 1.8–2.0 (m, 6H), 4.8 (m, 1H), 6.8 (t, 1H), 6.9 (d, 1H), 7.2 (t, 1H), 7.5 (d, 1H).

EXAMPLE 125

2-[(Aminocarbonyl)amino]-5-{2-[(1-isopropylpyrrolidin-3-yl)oxy]phenyl}-3-thiophenecarboxamide a) The compound was made from 3-(2-bromophenoxy)-1-isopropylpyrrolidine by a similar manner to Example 10 (e), except that the triisopropyl borate was added after adding the butyl lithium solution in the first step, the solvent for the second step was dimethoxyethane/water (10:1) and solid sodium hydrogen carbonate was used and that the solid product was purified by ion exchange chromatography to yield the product (42 mg).
MS 389 (M+H)+. $^1$H NMR (DMSO-D6) 1.0 (d, 6H), 2.0 (m, 1H), 2.2 (m, 1H), 2.4 (m, 1H), 2.6 (m, 1H), 2.75 (m, 2H), 3.0 (m, 1H), 5.0 (m, 1H), 6.85 (brs, 2H), 7.0 (m, 2H), 7.15 (t, 1H), 7.2 (brs, 1H), 7.6 (m, 2H), 7.75 (s, 1H), 10.9 (s, 1H).

b) 3-(2-Bromophenoxy)-1-isopropylpyrrolidine
To a solution of 2-bromophenol (2.6 g) in dimethylacetamide (20 ml) was added sodium hydride (640 mg) portionwise. A solution of 1-isopropylpyrrolidin-3-yl methanesulphonate [Example 134 (c)] in dimethylacetamide (20 ml) was added and the mixture was heated to 150° C. for 18 h. The mixture was allowed to cool and partitioned between water and dichloromethane. The organic phase was extracted with 2N aqueous hydrochloric acid which was then neutralised and extracted with dichloromethane. The extracts were dried (MgSO$_4$), the solvent removed under vacuum and the product purified by silica chromatography using dichloromethane/aqueous ammonia/methanol mixtures to yield the title compound as a brown oil (496 mg).
MS 284 (M+H)+. $^1$H NMR (DMSO-D6) 1.0 (d, 6H), 1.8 (m, 1H), 2.2 (m, 1H), 2.35–2.6 (m, 2H obscured), 2.7 (m, 2H), 3.0 (m, 1H), 4.9 (m, 1H), 6.9 (t, 1H), 7.05 (d, 1H), 7.3 (t, 1H), 7.55 (d, 1H).

EXAMPLE 126

2-[(Aminocarbonyl)amino]-5-{2-[(1-ethylpyrrolidine-3-yl)oxy]phenyl}-3-thiophenecarboxamide a) The title compound was prepared from 3-(2-bromophenoxy)-1-ethylpyrrolidine in a similar manner to Example 43 (a).
MS (ES) 375 (M+H)+. $^1$HNMR (DMSO-D6) 1.0 (t, 3H), 1.95 (m, 1H), 2.25 (m, 2H), 2.5 (m, obscured), 2.7 (m, 1H), 3.0 (m, 1H), 4.95 (m, 1H), 6.8 (s, 2H), 6.9–7.1 (m, 3H), 7.2 (m, 2H), 7.5–7.7 (m, 3H), 7.75 (s, 1H), 10.9 (s, 1H).

b) 3-(2-Bromophenoxy)-1-ethyl]pyrrolidine
1-Ethyl-3-pyrrolidinol (0.5 ml), 2-bromophenol (0.37 ml) and triphenylphosphine (1.02 g) were dissolved in tetrahydrofuran (10 ml) and the mixture cooled in an ice bath before dropwise addition of diisopropyl azodicarboxylate (0.77 ml). The mixture was allowed to warm to room temperature over 3 h. The mixture was concentrated in vacuo and partitioned between ether (50 ml) and water (50 ml) and the aqueous phase was extracted fisher with ether (50 ml). The combined organic phases were washed with water (2×25 ml), brine (2×25 ml), dried (MgSO$_4$) and concentrated in vacuo. The product was dissolved in ethyl acetate (50 ml) and extracted with 2M aqueous hydrochloric acid (3×20 ml). The aqueous washings were combined and basified by the addition of solid sodium hydroxide and extracted with ethyl acetate (3×20 ml), dried (MgSO$_4$) and concentrated in vacuo. The residue was purified by cation exchange chromatography eluting with ammonia/methanol/dichloromethane mixtures. This gave the title compound as a pale orange oil (529 mg).
MS (ES) 270 (M+H)+. $^1$H NMR (DMSO-D6) 1.0 (t, 3H), 1.8 (m, 1H), 2.25 (m, 1H), 2.4 (m, 3H), 2.65 (m, 2H), 2.9 (m, 1H), 4.9 (m, 1H), 6.9 (m, 1H), 7.05 (d, 1H), 7.3 (t, 1H), 7.55 (d, 1H).

EXAMPLE 127

2-[(Aminocarbonyl)amino]-5-{2-[(1-tert-butyloxycarbonyl-3-pyrrolidinyl)oxy]phenyl}-3-thiophenecarboxamide a) The title compound was prepared from 1-tert-butyloxycarbonyl 3-(2-bromophenoxy)-pyrrolidine in a similar manner to Example 9 (e).
MS (ES) 445 (M−H)−. $^1$H NMR (DMSO-D6) 1.35 (s, 9H), 3.4–3.9 (m, obscured), 5.15 (s, 1H), 6.8 (bs, 2H), 7.05 (t, 1H), 7.1 (m, 1H), 7.2 (m, 2H), 7.6–7.7 (brs, 1H), 7.65 (d, 1H), 7.75 (s, 1H), 10.9 (s, 1H).

b) 3-(2-Bromophenoxy)-1-(tert-butyloxycarbonyl)pyrrolidine
3-(2-Bromophenoxy)pyrrolidine (1 g) was dissolved in methanol (50 ml) and di-tert-butyl dicarbonate (992 mg) was added. The reaction mixture was stirred for 1 h and the reaction mixture concentrated in vacuo yielding a pale orange oil that solidified to white solid on standing (1.5 g).
MS (ES) 342 (M+H)+. $^1$H NMR (DMSO-D6) 1.2 (s, 9H), 2.1 (m, 2H), 3.2–3.6 (m, obscured), 5.15 (s, 1H), 6.9 (m, 1H), 7.15 (m, 1H), 7.35 (m, 1H), 7.55 (dd, 1H).

c) 3-(2-Bromophenoxy)pyrrolidine
1-tert-Butyloxycarbonyl-3-hydroxypyrrolidine (1 g), 2-bromophenol (710 mg) and triphenylphosphine (1.29 g) were dissolved in tetrahydrofuran (15 ml) and the mixture cooled in an ice bath before dropwise addition of diisopropyl azodicarboxylate (0.96 ml). The mixture was allowed to warm to room temperature over 3 h, concentrated in vacuo, partitioned between ether (50 ml) and water (50 ml) and the aqueous phase was extracted further with ether (50 ml). The combined organic phases were washed with water (2×25 ml), brine (2×25 ml), dried (MgSO$_4$) and concentrated in vacuo. The product was dissolved in dichloromethane (10 ml) and trifluoroacetic acid (5 ml) was added and the reaction stirred for 1 h. The mixture was concentrated in vacuo and the residue was purified by cation exchange chromatography eluting with ammonia/methanol/dichloromethane mixtures. This gave the title compound as a pale orange oil (437 mg).

MS (ES) 242 (M+H)⁺. ¹H NMR (DMSO-D6) 1.75 (m, 1H), 2.0 (m, 1H), 2.75–3.2 (m, obscured), 4.9 (m, 1H), 6.85 (m, 1H), 7.1 (m, 1H), 7.3 (m, 1H), 7.5 (m, 1H).

d) 1-tert-Butyloxycarbonyl-3-hydroxypyrrolidine

The title compound was prepared from pyrrolidin-3-ol (2 g) in a similar manner to Example 127 (b) except the product was dissolved in diethyl ether (50 ml) washed with water (3×20 ml), brine (2×20 ml), dried (MgSO₄) and concentrated in vacuo to yield a clear oil (3.5 g).

MS (ES) 188 (M+H)⁺. ¹H NMR (DMSO-D6) 1.2 (s, 9H), 1.6–1.9 (m, 2H), 3.2–3.4 (m, obscured), 4.2 (m, 1H).

EXAMPLE 128

2-[(Aminocarbonyl)amino]-5-[2-(pyrrolidin-3-yloxy)phenyl]-3-thiophenecarboxamide 2-[(Aminocarbonyl)amino]-5-{2-[(1-tert-butyloxycarbonylpyrrolidin-3-yl)oxy]phenyl}-3-thiophenecarboxamide (200 mg) was suspended in dichloromethane (30 ml) and trifluoroacetic acid (5 ml) was added. The mixture was stirred for 1 h, followed by concentration in vacuo. The product was treated with 38% aqueous ammonia and then isolated by filtration as a brown powder (98 mg).

MS (ES) 347 (M+H)⁺. ¹H NMR (DMSO-D6) 1.8–2.0 (m, 2H), 2.7 (m, 1H), 2.8–3.1 (m, 4H), 4.9 (s, 1H), 6.8 (brs, 2H), 6.9 (m, 1H), 7.0 (m, 1H), 7.15 (m, 2H), 7.5–7.7 (m, 2H), 7.7 (s, 1H), 10.9 (s, 1H).

EXAMPLE 129

2-[(Aminocarbonyl)amino]-5-{2-[(1-methylpiperidin-2-yl)methoxy]phenyl}-3-thiophenecarboxamide a) The title compound was made from 2-[(2-bromophenoxy)methyl]-1-methylpiperidine in a similar manner to Example 43 (a).

MS (ES) 389 (M+H)⁺. ¹H NMR (DMSO-D6) 1.4–1.9 (m, 6H), 2.0–2.1 (m, 1H), 2.35 (s, 3H), 2.65 (m, 1H), 2.8 (m, 1H), 2.9 (m, 1H), 4.7 (m, 1H), 6.85 (brs, 2H), 7.0 (m, 1H), 7.1 (m, 1H), 7.25 (m, 1H), 7.6 (m, 2H), 7.8 (s, 1H), 10.9 (s, 1H).

b) 2-[(2-Bromophenoxy)methyl]-1-methylpiperidine

The title compound was made from (1-methylpiperidin-2-yl)methanol in a manner similar to Example 126 (b).

MS (ES) 284 (M+H)⁺. ¹H NMR (CDCl₃) 1.4–2.0 (m, 6H), 2.1–2.2 (m, 1H), 2.35 (s, 3H), 2.55 (m, 1H) 2.7–2.8 (m, 1H), 2.9–3.0 (m, 1H), 4.1–4.2 (m, 1H), 6.8–6.9 (m, 2H), 7.2 (m, 1H), 7.5 (m, 1H).

EXAMPLE 130

(2S)-2-[(Aminocarbonyl)amino]-5-(2-{[1-methylpyrrolidin-2-yl]methoxy}phenyl)-3-thiophenecarboxamide a) The title compound was made from (2S)-2-[(2-bromophenoxy)methyl]-1-methylpyrrolidine in a similar manner to Example 43 (a) and the precipitate purified by preparative HPLC.

MS (ES) 375 (M+H)⁺. ¹H NMR (DMSO-D6) 1.65–1.8 (m, 3H) 2.2 (m, 2H), 2.4 (s, 3H), 2.75 (m, 1H), 3.0 (m, 1H), 3.85 (m, 1H), 4.2 (m, 1H), 6.8–6.9 (brs, 2H), 7.0 (t, 1H), 7.1 (m, 1H), 7.2–7.3 (m, 2H), 7.5–7.7 (m, 2H), 7.8 (s, 1H), 10.9 (s, 1H).

b) (2S-2-[(2-Bromophenoxy)methyl]-1-methylpyrrolidine

The title compound was made from (S)-(–)-1-methyl-2-pyrrolidinemethanol in a manner similar to Example 126 (b).

MS (ES) 270 (M+H)⁺. ¹H NMR (DMSO-D6) 1.65–1.8 (m, 3H), 2.2–2.3 (m, 2H), 2.4 (s, 3H), 2.65 (m, 1H), 3.0 (m, 1H), 3.9–4.05 (m, 2H), 6.9 (m, 1H), 7.1–7.2 (m, 1H), 7.35 (m, 1H), 7.55 (m, 1H).

EXAMPLE 131

2-[(Aminocarbonyl)amino]-5-(2-{[1-(2-methoxyethyl)pyrrolidin-3-yl]oxy}phenyl)-3-thiophenecarboxamide a) The title compound was made from 3-(2-bromophenoxy)-1-(2-methoxyethyl)-pyrrolidine in a similar manner to Example 43 (a). The precipitate was purified by cation exchange chromatography eluting with ammonia/methanol/dichloromethane mixtures.

MS (ES) 405 (M+H)⁺. ¹H NMR (DMSO-D6) 1.9–2.0 (m, 1H), 2.2–2.3 (m, 1H), 2.6–2.7 (m, 2H), 2.75 (m, 2H), 3.1 (m, 1H), 3.2 (m, 1H), 3.25 (s, 3H), 3.45 (m, 2H), 4.95 (m, 1H), 6.8–6.9 (brs, 2H), 6.95–7.05 (m, 2H), 7.25 (m, 2H), 7.6–7.7 (m, 2H), 7.75 (s, 1H), 10.9 (s, 1H).

b) 3-(2-Bromophenoxy)-1-(2-methoxyethyl)pyrrolidine 3-(2-Bromophenoxy)pyrrolidine (1.23 g), 1-bromo-2-methoxyethane (0.526 ml) and potassium carbonate (842 mg) were mixed with dimethylformamide (50 ml) and stirred for two days. The mixture was added to water (100 ml). The mixture was extracted with diethyl ether (3×50 ml), washed with water (2×50 ml), brine (2×30 ml), dried (MgSO₄) and concentrated in vacuo. Purification was achieved using cation exchange chromatography eluting with ammonia/methanol/dichloromethane mixtures yielding product as a clear oil (0.8 g).

Ms (ES) 300 (M+H)⁺. ¹H NMR (DMSO-D6) 1.7–1.8 (m, 1H), 2.2–2.3 (m, 1H), 2.5–2.8 (m, 5H), 2.9 (m, 1H), 3.2 (s, 3H), 3.4 (m, 2H), 4.9 (m, 1H), 6.90–6.95 (m, 1H), 7.0 (m, 1H), 7.25–7.35 (m, 1H), 7.5 (s, 1H).

EXAMPLE 132

(2R)-2-[(Aminocarbonyl)amino]-5-(2-{[1-methylpyrrolidin-2-yl]methoxy}phenyl)-3-thiophenecarboxamide a) The title compound was made from (2R)-2-[(2-bromophenoxy)methyl]-1-methylpyrrolidine in a similar manner to Example 43 (a) and the precipitate purified by preparative LCMS.

MS (ES) 375 (M+H)⁺. ¹H NMR (DMSO-D6) 1.65–1.8 (m, 3H) 2.2 (m, 2H), 2.4 (s, 3H), 2.75 (m, 1H), 3.0 (m, 1H), 3.85 (m, 1H), 4.2 (m, 1H), 6.8–6.95 (brs, 2H), 7.0 (t, 1H), 7.1 (m, 1H), 7.2–7.3 (m, 2H), 7.6–7.7 (m, 2H), 7.8 (s, 1H), 10.9 (s, 1H).

b) (2R)-2-[(2-Bromophenoxy)methyl]-1-methylpyrrolidine (2R)-2-[(2-Bromophenoxy)methylpyrrolidine (1.84 g), potassium carbonate (1.09 g) and methyl iodide (0.49 ml) were stirred in dimethylformamide (10 ml) for 2 h at room temperature. The mixture was concentrated in vacuo and water added (50 ml). The mixture was extracted with diethyl ether (3×30 ml). The organic portions were combined and washed with water (2×20 ml), brine (2×20 ml) and dried (MgSO$_4$) and concentrated in vacuo yielding the title compound as a pale orange oil (0.75 g).

MS (ES) 270 (M+H)$^+$. $^1$H NMR (DMSO-D6) 1.6–1.75 (m, 3H), 2.0 (m, 1H), 2.2 (m, 1H), 2.45 (s, 3H), 2.8 (m, 1H), 2.95 (m, 1H), 3.8–4.05 (m, 2H) 6.8 (m, 1H), 7.1 (m, 1H), 7.3 (m, 1H), 7.55 (m, 1H).

c) (2R)-2-[(2-Bromophenoxy)methyl]pyrrolidine

This compound was made from (2R)-1-tert-butyloxycarbonyl-2-hydroxymethyl)pyrrolidine (2 g) in a similar manner to Example 127 (b-c), yielding the product as a brown oil (1.84 g).

MS (ES) 256 (M+H)$^+$. $^1$H NMR (DMSO-D6) 1.5–1.9 (m, 4H), 2.8–2.9 (m, 2H), 3.45 (m, 1H), 3.85–4.0 (m, 2H), 6.9 (m, 1H), 7.15 (m, 1H), 7.35 (m, 1H), 7.6 (m, 1H).

EXAMPLE 133

2-[(Aminocarbonyl)amino]-5-[2-(2-(2,2,6-trimethylpiperidin-1-yl)ethoxy)phenyl]-3-thiophenecarboxamide a) The title compound was prepared from 1-[2-(2-bromophenoxy)ethyl]-2,2,6-trimethylpiperidine in a similar manner to Example 9 (e).

MS (ES) 431 (M+H)$^+$. $^1$H NMR (DMSO-D6) 0.95 (s, 3H), 1.0 (d, 3H), 1.05 (s, 3H), 1.4 (m, 6H), 2.6 (m, 2H), 3.1 (m, 1H), 3.95 (m, 2H), 6.8 (brs, 2H), 6.95 (m, 1H), 7.05 (dd, 1H), 7.2 (m, 2H), 7.6 (dd, 1H), 7.6 (brs, 1H), 7.75 (s, 1H), 10.91 (brs, 1H).

b) 1-[2-(2-Bromophenoxy)ethyl]2,2,6-trimethylpiperidine

The title compound was prepared from 1-(2-chloroethyl)-2,2,6-trimethylpiperidine hydrochloride and 2-bromophenol in a similar manner to Example 2 (b).

MS (ES) 326 (M+H)$^+$. $^1$H NMR (DMSO-D6) 0.95 (s, 3H), 1.0 (d, 3H), 1.05 (s, 3H), 1.4 (m, 6H), 2.6 (m, 2H), 3.0 (m, 1H), 3.9 (m, 2H), 6.95 (m, 1H), 7.05 (dd, 1H), 7.3 (m, 1H), 7.55 (dd, 1H).

c) 1-(2-Chloroethyl)-2,2,6-trimethylpiperidine

The title compound was prepared as described in GB Patent 831345.

EXAMPLE 134

2-[(Aminocarbonyl)amino]-5-{5-chloro-2-[(1-isopropylpyrrolidin-3-yl)oxy]phenyl}-3-thiophenecarboxamide a) The title compound was prepared from 3-(2-bromo-4-chlorophenoxy)-1-isopropylpyrrolidine in a similar manner to Example 9 (e) except that the concentrated reaction mixture was partitioned between dichloromethane and saturated sodium carbonate solution. The solvent layer was washed (brine), dried and evaporated to an oil. The pure product was obtained by silica chromatography eluting with dichloromethane/methanol mixtures.

MS (ES) 423 (M+H)$^+$. $^1$H NMR (DMSO-D6) 1.0 (d, 6H), 1.95 (m, 1H), 2.2 (m, 1H), 2.55 (m, 1H), 2.7 (m, 1H), as 2.8 (m, 2H), 3.1 (m, 1H), 4.95 (m, 1H), 6.8 (m, 2H), 6.95 (dd, 1H), 7.15 (d, 1H), 7.2 (brs, 1H), 7.6 (brs, 1H), 7.68 (s, 1H), 7.8 (s, 1H), 10.85 (s, 1H).

b) 3-(2-Bromo-4-chlorophenoxy)-1-isopropylpyrrolidine

Sodium hydride (0.43 g, 60% dispersion in oil) was added portionwise to a stirred solution of 2-bromo-4-chlorophenol (2.1 g) in dimethylacetamide (15 ml). After stirring for 15 minutes, a solution of 1-isopropylpyrrolidin-3-yl methanesulphonate (15 mmol) in dimethylacetamide (15 ml) was added portionwise and the resulting mixture was heated at 90° C. for 18 h. The solvent was evaporated and the residue dissolved in ethyl acetate/water. The solvent phase was washed twice with brine and then dried and evaporated to an oil. Purification was achieved using silica chromatography eluting with dichloromethane/methanol mixtures. This gave the title compound (3.0 g).

MS (ES) 318 (M+H)$^+$. $^1$H NMR (DMSO-D6) 1.2 (d, 6H), 2.1 (m, 1H), 2.25 (m, 1H), 3.2 (m, 4H), 3.6 (m, 1H), 5.15 (m, 1H), 7.2 (d, 1H), 7.4 (m, 1H), 7.7 (d, 1H).

c) 1-Isopropylpyrrolidin-3-yl methanesulphonate

A solution of 1-isopropylpyrrolidin-3-ol (2.0 ml) and triethylamine (2.5 ml) in toluene (25 ml) was cooled to 0° C. and methanesulphonyl chloride (1.4 ml) was added dropwise with stirring. The mixture was allowed to warm to ambient temperature and is stirred for a further 2 h. The reaction was filtered and the filtrate evaporated to an oil which was used immediately.

EXAMPLE 135

2-[(Aminocarbonyl)amino]-5-{4-fluoro-2-[(1-isopropylpyrrolidin-3-yl)oxy]phenyl}-3-thiophenecarboxamide a) The title compound was prepared from 3-(2-bromo-5-fluorophenoxy)-1-isopropylpyrrolidine in a similar manner to Example 9 (e) and the purification was achieved as in Example 134 (a).

MS (ES) 407 (M+H)$^+$. $^1$H NMR (DMSO-D6) 1.0 (d, 6H), 1.9 (m, 1H), 2.2 (m, 1H), 2.4 (m, 2H), 2.7 (m, 2H), 3.05 (m, 1H), 4.95 (m, 1H), 6.8 (m, 3H), 7.2 (brs, 1H), 7.55 (m, 2H), 7.65 (s, 1H), 7.8 (s, 1H), 10.88 (brs, 1H).

b) 3-(2-Bromo-5-fluorophenoxy)-1-isopropylpyrrolidine

The title compound was prepared from 2-bromo-5-fluorophenol in a similar manner to Example 134 (b).

MS (ES) 302 (M+H)$^+$. $^1$H NMR (DMSO-D6) 1.0 (d, 6H), 1.8 (m, 1H), 2.2 (m, 1H), 2.4 (m, 1M), 2.65 (m, 2H), 3.0 (m, 2H), 4.9 (m, 1H), 6.75 (m, 1H), 6.95 (m, 1H), 7.6 (m, 1H).

EXAMPLE 136

2-[(Aminocarbonyl)amino]-5-{4,5-difluoro-2-[(1-isopropylpyrrolidin-3-yl)oxy]phenyl}-3-thiophenecarboxamide a) The title compound was prepared from 3-(2-bromo-4,5-difluorophenoxy)-1-isopropylpyrrolidine in a similar manner to Example 9 (e)) and the purification was achieved as Example 134 (a).

MS (ES) 425 (M+H)$^+$. $^1$H NMR (DMSO-D6) 1.05 (d, 6H), 2.0 (m, 1H), 2.25 (m, 1H), 2.4 (m, 1H), 2.55 (m, 1H), 2.7 (m, 2H), 3.1 (m, 1H), 5.0 (m, 1H), 6.9 (brs, 2H), 7.2 (m, 1H), 7.3 (brs, 1H), 7.55 (brs, 1H), 7.6 (m, 1H), 7.8 (s, 1H), 10.9 (brs, 1H).

b) 3-(2-Bromo-4,5-difluorophenoxy)-1-isopropylpyrrolidine

The title compound was prepared from 2-bromo-4,5-difluorophenyl in a similar manner to Example 134 (b) except that the compound was purified by cation exchange chromatography eluting with ammonia/methanol mixtures.

MS (ES) 320 (M$^+$). $^1$H NMR (DMSO-D6) 1.0 (d, 6H), 1.75 (m, 1H), 2.2 (m, 1H), 2.4 (m, 1H), 2.65 (m, 2H), 2.95 (m, 2H), 4.85 (m, 1H), 7.25 (m, 1H), 7.8 (m, 1H).

EXAMPLE 137

2-[(Aminocarbonyl)amino]-5-{2-[(1-isopropylpyrrolidin-3-yl)oxy]-5-methylphenyl}-3-thiophenecarboxamide a) The title compound was prepared from 3-(2-bromo-4-methylphenoxy)-1-isopropylpyrrolidine in a similar manner to Example 9 (e) and the purification was achieved as in Example 134 (a) except that cation exchange chromatography was employed using methanol/ammonia mixtures with final purification by preparative hplc.

MS (ES) 403 (M+H)$^+$. $^1$H NMR (DMSO-D6) 1.0 (d, 6H), 1.9 (m, 1H), 2.1 (m, 1H), 2.15 (s, 3H), 2.4 (m, 1H), 2.55 (m, 1H), 2.7 (m, 2H), 3.0 (m, 1H), 4.9 (m, 1H), 6.8 (brs, 2H), 6.85 (d, 1H), 6.95 (m, 1H), 7.2 (brs, 1H), 7.4 (s, 1H), 7.6 (brs, 1H), 7.7 (s, 1H), 10.89 (brs, 1H).

b) 3-(2-Bromo-4-methylphenoxy)-1-isopropylpyrrolidine

The title compound was prepared from 2-bromo-4-methylphenol in a similar manner to Example 134 (b) except that the compound was purified by cation exchange chromatography eluting with ammonia/methanol mixtures.

MS (ES) 298 (M+H)$^+$.

EXAMPLE 138

2-[(Aminocarbonyl)amino]-5-{5-cyano-2-[(1-isopropylpyrrolidin-3-yl)oxy]phenyl}-3-thiophenecarboxamide a) The title compound was prepared from 3-(2-bromo-4-cyanophenoxy)-1-isopropylpyrrolidine in a similar manner to Example 9 (e) and the purification was achieved in as in Example 134 (a) except that cation exchange chromatography was employed using methanol/ammonia mixtures with final purification by preparative hplc.

MS (ES) 414 (M+H)$^+$. $^1$H NMR (DMSO-D6) 1.0 (d, 6H), 1.95 (m, 1H), 2.15 (m, 1H), 2.6 (m, 1H), 2.8 (m, 2H), 3.1 (m, 2H), 5.1 (m, 1H), 6.8 (brs, 2H), 7.15 (d, 1H), 7.25 (brs, 1H), 7.6 (brs, 1H), 7.65 (d, 1H), 7.85 (s, 1H), 8.0 (s, 1H), 10.9 (brs, 1H).

b) 3-(2-Bromo-4-cyanophenoxy)-1-isopropylpyrrolidine

The title compound was prepared from 2-bromo-4-cyanophenyl in a similar manner to Example 134 (b) except that the compound was purified by cation exchange chromatography eluting with ammonia/methanol mixtures.

MS (ES) 309 (M+H)$^+$. $^1$H NMR (DMSO-D6) 1.0 (d, 6H), 1.8 (m, 1H), 2.2 (m, 2H), 2.6 (m, 1H), 2.65 (m, 2H), 2.95 (m, 1H), 5.0 (m, 1H), 7.2 (d, 1H), 7.8 (m, 1H), 8.1 (m, 1H).

EXAMPLE 139

2-[(Aminocarbonyl)amino]-5-{2-[(1-isopropylpyrrolidin-3-yl)oxy]-5-methoxyphenyl}-3-thiophenecarboxamide a) The title compound was prepared from 3-(2-bromo-4-methoxyphenoxy)-1-isopropylpyrrolidine in a similar manner to Example 9 (e) and the purification was achieved as in Example 134 (a) except that the crude product was purified by trituration with dichloromethane/methanol mixtures.

MS (ES) 419 (M+H)$^+$. $^1$H NMR (DMSO-D6) 1.0 (d, 6H), 1.9 (m, 1H), 2.15 (m, 1H), 2.4 (m, 1H), 2.55 (m, 1H), 2.7 (m, 2H), 3.0 (m, 1H), 3.75 (s, 3H), 4.8 (m, 1H), 6.75 (m, 1H), 6.8 (brs, 2H), 6.9 (m, 1H), 7.2 (m, 1H), 7.22 (brs, 1H), 7.6 (brs, 1H), 7.8 (s, 1H), 10.85 (brs, 1H).

b) 3-(2-Bromo-4-methoxyphenoxy)-1-isopropylpyrrolidine

The title compound was prepared from 2-bromo-4-methoxyphenol in a similar manner to Example 134 (b) except that the compound was purified by cation exchange chromatography eluting with ammonia/methanol mixtures.

MS (ES) 314 (M+H)$^+$. $^1$H NMR (DMSO-D6) 1.0 (d, 6H), 1.9 (m, 2H), 2.4 (m, 1H), (2.5, 1H obscured), 2.75 (m, 3H), 3.8 (s, 3H), 4.8 (m, 1H), 6.7 (m, 1H), 6.9 (m, 1H), 7.2 (m, 1H).

c) 2-Bromo-4-methoxyphenol

The title compound was prepared as described in S. Afr. J. Chem., 1999, 52, 112.

EXAMPLE 140

2-[(Aminocarbonyl)amino]-5-{3,5-difluoro-2-[(1-isopropylpyrrolidin-3-yl)oxy]phenyl}-3-thiophenecarboxamide a) The title compound was prepared from 3-(2-bromo-4,6-difluorophenoxy)-1-isopropylpyrrolidine in a similar manner to Example 9 (e) and the purification was achieved as in Example 134 (a) except that the compound was purified by cation exchange chromatography eluting with ammonia/methanol mixtures and subsequent preparative hplc.

MS (ES) 425 (M+H)$^+$. $^1$H NMR (DMSO-D6) 0.95 (m, 6H), 1.95 (m, 2H), 2.4 (m, 1H), 2.75 (m, 4H), 4.7 (m, 1H), 6.9. (m, 2H), 7.2 (m, 2H), 7.4 (m, 1H), 7.6 (m, 1H), 7.85 (s, 1H), 10.95 (brs, 1H).

b) 3-(2-Bromo-4,6-difluorophenoxy)-1-isopropylpyrrolidine

The title compound was prepared from 2-bromo-4,6-difluorophenyl in a similar manner to Example 134 (b) except that the compound was purified by cation exchange chromatography eluting with ammonia/methanol mixtures and subsequent preparative hplc.

MS (ES) 320 (M+H)$^+$. $^1$H NMR (DMSO-D6) 1.0 (d, 6H), 1.95 (m, 1H), 2.05 (m, 1H), 2.4 (m, 1H), (2.5, 1H obscured), 2.8 (m, 3H), 4.7 (m, 1H), 7.4 (m, 2H).

EXAMPLE 141

2-[(Aminocarbonyl)amino]-5-{2-[(1-isopropylpyrrolidin-3-yl)oxy]-3-methoxyphenyl}-3-thiophenecarboxamide a) The title compound was prepared from 3-(2-bromo-6-methoxyphenoxy)-1-isopropylpyrrolidine in a similar manner to Example 9 (e) and the purification was achieved as in Example 134 (a) except that the compound was purified by cation exchange chromatography eluting with ammonia/methanol mixtures and subsequent preparative hplc.

MS (ES) 419 (M+H)$^+$. $^1$H NMR (DMSO-D6) 0.95 (d, 6H), 1.8 (m, 2H), 2.4 (m, 2H), 2.8 (m, 3H), 3.8 (s, 3H), 4.8 (m, 1H), 6.8 (m, 2H), 6.9 (m, 1H), 7.1 (m, 2H), 7.2 (m, 1H), 7.55 (brs, 1H), 7.7 (s, 1H), 10.92 (brs, 1H).

b) 3-(2-Bromo-6-methoxyphenoxy)-1-isopropylpyrrolidine

The title compound was prepared from 2-bromo-6-methoxyphenol in a similar manner to Example 134 (b) except that the compound was purified by cation exchange chromatography eluting with ammonia/methanol mixtures.

MS (ES) 314 (M+H)+. 1H NMR (DMSO-D6) 1.0 (d, 6H), 1.95 (m, 2H), 2.4 (m, 1H), (2.5, 1H obscured), 2.75 (m, 3H), 3.8 (s, 3H), 4.8 (m, 1H), 7.0 (m, 2H), 7.15 (m, 1H).

c) 2-Bromo-6-methoxyphenol

The title compound was prepared as described in *Synthesis*, 2001, 741.

EXAMPLE 142

2-[(Aminocarbonyl)amino]-5-12-[(1-isopropylpyrrolidin-3-yl)oxy]-5-trifluoromethylphenyl]-3-thiophenecarboxamide a) The title compound was prepared from 3-[2-bromo-4-trifluoromethylphenoxy]-1-isopropylpyrrolidine in a similar manner to Example 9 (e) and the purification was achieved as in Example 134 (a) except that the compound was obtained pure by washing with methanol.

MS (ES) 457 (M+H)+. 1H NMR (DMSO-D6) 1.0 (d, 6H), 1.95 (m, 1H), 2.25 (m, 2H), 2.55 (m, 1H), 2.8 (m, 2H), 3.1 (m, 1H), 5.05 (m, 1H), 6.8 (m, 2H), 7.2 (m, 1H), 7.25 (m, 1H), 7.5 (m, 1H), 7.65 (m, 1H), 7.9 (m, 2H) 10.92 (m, 1H).

b) 3-[2-Bromo-4-trifluoromethylphenoxy]-1-isopropylpyrrolidine

The title compound was prepared from 2-bromo-4-trifluoromethylphenyl in a similar manner to Example 134 (b) except that the compound was purified by cation exchange chromatography eluting with ammonia/methanol mixtures.

MS (ES) 352(M+H)+. 1H NMR (DMSO-D6) 1.0 (d, 6H), 1.8 (m, 1H), 2.2–2.4 (m, 3H), 2.7 (m, 2H), 3.0 (m, 1H), 5.0 (m, 1H), 7.2 (d, 1H), 7.65 (m, 1H), 7.9 (d, 1H).

c) 2-Bromo-4-trifluoromethylphenyl

The title compound was prepared as described in *Chem. Pharm. Bull*, 1996, 44, 4.

EXAMPLE 143

2-[(Aminocarbonyl)amino]-5-{2-[(1-isopropylpyrrolidin-3-yl)oxy]-4-trifluoromethylphenyl}-3-thiophenecarboxamide a) The title compound was prepared from 3-[2-bromo-5-trifluoromethylphenoxy]-1-isopropylpyrrolidine in a similar manner to Example 9 (e) and the purification was achieved as in Example 134 (a) except that the compound was obtained pure by cation exchange chromatography eluting with ammonia/methanol mixtures.

MS (ES) 457 (M+H)+. 1H NMR (DMSO-D6) 1.05 (d, 6H), 2.0 (m, 1H), 2.3 (m, 1H), 2.5 (m, 2H), 2.8 (m, 2H), 3.1 (m, 1H), 5.1 (m, 1H), 6.9 (m, 2H), 7.3 (m, 2H), 7.6 (m, 2H), 7.9 (dd, 1H), 8.0 (s, 1H), 10.95 (s, 1H).

b) 3-[2-Bromo-5-trifluoromethylphenoxy]-1-isopropylpyrrolidine

The title compound was prepared from 2-bromo-5-trifluoromethylphenyl in a similar manner to Example 134 (b) except that the compound was purified by cation exchange chromatography eluting with ammonia/methanol mixtures.

MS (ES) 352 (M+H)+. 1H NMR (CDCl3) 1.05 (d, 6H), 2.0 (m, 1H), 2.3 (m, 1H), 2.5 (m, 1H), 2.8 (m, 3H), 3.2 (m, 1H), 4.85 (m, 1H), 7.0(d, 1H), 7.05 (d, 1H), 7.4 (d, 1H).

c) 2-Bromo-5-(trifluoromethyl)phenol

The title compound was prepared as described in *Chem. Pharm. Bull.*, 1996, 44, 4.

EXAMPLE 144

2-[(Aminocarbonyl amino]-5-{2-[(1-isopropylpyrrolidin-3-yl)oxy]-4-methoxyphenyl}-3-thiophenecarboxamide a) The title compound was prepared from 3-(2-bromo-5-methoxyphenoxy)-1-isopropylpyrrolidine in a similar manner to Example 9 (e) and the purification was achieved as in Example 134 (a) except that the compound was obtained pure by cation exchange chromatography eluting with ammonia/methanol mixtures.

MS (ES) 419 (M+H)+. 1H NMR (DMSO-D6) 1.0 (d, 6M), 1.9 (m, 1H), 2.2 (m, 1H), 2.4 (m, 1H), 2.55 (m, 1H), 2.7 (m, 2H), 3.0 (m, 1H), 3.75 (s, 3H), 4.95 (m, 1H), 6.5 (m, 1H), 6.6 (m, 1H), 6.8 (brs, 2H), 6.9 (m, 1H), 7.2 (brs, 1H), 7.5 (m, 1H), 7.55 (s, 1H), 10.86 (brs, 1H).

b) 3-(2-Bromo-5-methoxyphenoxy)-1-isopropylpyrrolidine

The title compound was prepared from 2-bromo-5-methoxyphenol in a similar manner to Example 134 (b) except that the compound was purified by cation exchange chromatography eluting with ammonia/methanol mixtures.

MS (ES) 314 (M+H)+. 1H NMR (CDCl3) 1.1 (d, 6H), 2.0 (m, 1H), 2.25 (m, 1H), 2.45 (m, 1H), 2.75 (m, 3H), 3.2 (m, 1H), 3.75 (s, 3H), 4.8 (m, 1H), 6.4 (m, 2H), 7.4 (m, 1H).

c) 2-Bromo-5-methoxyphenol

The title compound was prepared as described in *J. Chem. Soc. Perkin Trans*1; 12,2927 (1983).

EXAMPLE 145

2-[(Aminocarbonyl)amino]-5-{5-fluoro-2-[(1-isopropylpyrrolidin-3-yl)oxy]phenyl}-3-thiophenecarboxamide a) The title compound was prepared from 3-(2-bromo-4-fluorophenoxy)-1-isopropylpyrrolidine in a similar manner to Example 9 (e) and the purification was achieved as in Example 134 (a) except that the compound was obtained pure by cation exchange chromatography eluting with ammonia/methanol mixtures.

MS (ES) 407 (M+H)+. 1H NMR (DMSO-D6) 1.0 (d, 6H), 1.95 (m, 1H), 2.2 (m, 1H), 2.4 (m, 1H), 2.6 (m, 1H), 2.75 (m, 2H), 3.05 (m, 1H), 4.95 (m, 1H), 6.8 (m, 2H), 7.0 (m, 2H), 7.2 (brs, 1H), 7.4 (m, 1H), 7.6 (brs, 1H), 7.8 (s, 1H), 10.88 (brs, 1H).

b) 3-(2-Bromo-4-fluorophenoxy)-1-isopropylpyrrolidine

The title compound was prepared from 2-bromo-5-fluorophenol in a similar manner to Example 134 (b) except that the compound was purified by cation exchange chromatography eluting with ammonia/methanol mixtures.

MS (ES) 302 (M+H)+. 1H NMR (DMSO-D6) 1.0 (d, 6H), 1.8 (m, 1H), 2.2 (m, 1H), 2.35 (m, 1H), 2.5 (m, 1H), 2.6 (m, 2H), 2.95 (m, 1H), 4.8 (m, 1H), 7.0 (m, 1H), 7.2 (m, 1H), 7.5 (m, 1H).

EXAMPLE 146

2-[(Aminocarbonyl)amino]-5-{2-[(1-isopropylpyrrolidin-3-yl)oxy]-3-(morpholin-4-ylmethyl)phenyl}-3-thiophenecarboxamide a) The title compound was prepared from 4-{3-bromo-2-[(1-isopropylpyrrolidin-3-yl)oxy]benzyl}morpholine in a similar manner to Example 9 (e) and the purification was achieved as in Example 134 (a) except that the compound was initially purified by cation exchange chromatography eluting with ammonia/methanol mixtures. Final purification was achieved using preparative hplc.

MS (ES) 488 (M+H)$^+$. $^1$H NMR (DMSO-D6) 2.0 (m, 1H), 2.3 (m, 1H), 2.55 (m, 2H), 2.75 (m, 2H), 3.0 (m, 1H), 3.7 (m, 2H), 5.0 (m, 1H), 6.8 (brs, 2H), 6.95 (m, 2H), 7.1 (m, 2H), 7.2 (brs, 1H), 7.3 (m, 2H), 7.6 (m, 2H), 7.8 (s, 1H), 10.95 (s, 1H).

b) 4-{3-Bromo-2-[(1-isopropylpyrrolidin-3-yl)oxy]benyl}morpholine

The title compound was prepared from 2-bromo-6-(morpholin-4-ylmethyl)phenol in a similar manner to Example 134 (b) except that the compound was purified by cation exchange chromatography eluting with ammonia/methanol mixtures.

MS (ES) 383 (M+H)$^+$. $^1$H NMR (CDCl$_3$) 1.1 (m, 6H), 2.15 (m, 2H), 2.5 (m, 4H), 2.6 (m, 1H), 2.9 (m, 4H), 3.6 (d, 2H), 3.7 (m, 4H), 4.9(m, 1H), 6.95 (m, 1H), 7.35 (dd, 1H), 7.45 (dd, 1H).

c) 2-Bromo-6-(morpholin-4-ylmethyl)phenol

Sodium triacetoxyborohydride (3.18 g) was added to a solution of 3-bromo-2-hydroxybenzaldehyde (2.0 g) and morpholine (1.04 ml) in tetrahydrofuran (30 ml) and the mixture stirred at ambient temperature for 18 h. After filtering from a little insoluble material, the filtrate was evaporated. The residue was partitioned between dichloromethane and water and the solvent phase was washed with water, dried and evaporated to an oil.

MS (ES) 272 (M+H)$^+$. $^1$H NMR (CDCl$_3$) 2.6 (m, 4H), 3.7 (s, 2H), 3.8 (m, 4H), 6.75 (m, 1H), 6.9 (m, 1H), 7.4 (m, 1H).

EXAMPLE 147

2-[(Aminocarbonyl)amino]-5-(2-{[(1-(cyclopropylmethyl)pyrrolidin-3-yl]oxy}phenyl)-3-thiophenecarboxamide a) The title compound was prepared from 3-(2-bromophenoxy)-1-(cyclopropylmethyl)-pyrrolidine in a similar manner to Example 134 (a) except that the compound was purified by cation exchange chromatography eluting with ammonia/methanol mixtures.

MS (ES) 401 (M+H)$^+$. $^1$H NMR (DMSO-D6) 0.05 (m, 2H), 0.4 (m, 2H), 0.8 (m, 1H), 1.7 (m, 1H), 1.9 (m, 1H), 2.2 (m, 2H), 2.55 (m, 1H), 2.6 (m, 2H), 3.0 (m, 1H), 4.9 (m, 1H), 6.8 (m, 2H), 6.9 (m, 2H), 7.15 (m, 2H), 7.2 (brs, 1H), 7.55 (m, 1H), 7.65 (s, 1H), 10.84 (s, 1H).

b) 3-(2-Bromophenoxy)-1-(cyclopropylmethyl)pyrrolidine

The title compound was prepared from 2-bromophenol and 1-(cyclopropylmethyl)pyrrolidin-3-yl methanesulphonate in a similar manner to Example 134 (b) except that the compound was purified by cation exchange chromatography eluting with ammonia/methanol mixtures.

MS (ES) 296 (M+H)$_+$. $^1$H NMR (CDCl$_3$) 0.15 (m, 2H), 0.5 (m, 2H), 0.9 (m, 1H), 2.4 (m, 2H), 2.8 (m, 3H), 3.0 (d, 2H), 3.2 (m, 1H), 4.9 (m, 1H), 6.8 (m, 1H), 7.2 (m, 1H), 7.5 (m, 1H).

c) 1-(Cyclopropylmethyl)pyrrolidin-3-yl methanesulphonate

The title compound was prepared in a similar manner to Example 134 (c) except that 1-(cyclopropylmethyl)pyrrolidin-3-ol was used.

d) 1-(Cyclopropylmethyl)pyrrolidin-3-ol

The title compound was prepared in a similar manner to Bull. Chem. Soc. Japan, 69, 213 (1996) except that cyclopropylmethyl bromide was used.

MS (ES) 142 (M+H)$^+$.

EXAMPLE 148

2-[(Aminocarbonyl)amino]-5-{2-[(1-cyclopropylpyrrolidin-3-yl)oxy]phenyl}-3-thiophenecarboxamide a) The title compound was prepared from 3-(2-bromophenoxy)-1-cyclopropylpyrrolidine in a similar manner to Example 9 (e) and the purification was achieved as in Example 134 (a) except that the product was isolated from the dichloromethane extract by cation exchange chromatography eluting with ammonia/methanol mixtures. Final purification was achieved using preparative hplc.

MS (ES) 387 (M+H)$^+$. $^1$H NMR (DMSO-D6) 0.3 (m, 3H), 0.8 (m, 1H), 1.4 (m, 1H), 1.65 (m, 1H), 1.9 (m, 1H), 2.2 (m, 1H), 2.3 (m, 1H), 2.65 (m, 1H), 2.9 (m, 1H), 4.95 (m, 1H), 6.9 (m, 2H), 7.0 (m, 2H), 7.2 (m, 2H), 7.6 (m, 2H), 7.7 (s, 1H), 10.9 (s, 1H).

b) 3-(2-Bromophenoxy)-1-cyclopropylpyrrolidine

The title compound was prepared from 2-bromophenol and 1-cyclopropylpyrrolidin-3-yl methanesulphonate in a similar manner to Example 134 (b) except that the compound was purified by cation exchange chromatography eluting with ammonia/methanol mixtures.

MS (ES) 282(M+H)$^+$. $^1$H NMR (CDCl$_3$) 0.6 (m, 2H), 0.95 (m, 3H), 1.6 (m, 1H), 2.0 (m, 1H), 2.2 (m, 1H), 2.7 (m, 1H), 2.9 (m, 1H), 3.2 (m, 1H), 4.8 (m, 1H), 6.8 (m, 2H), 7.2 (m, 1H), 7.55 (m, 1H).

c) 1-Cyclopropylpyrrolidin-3-yl methanesulphonate

The title compound was prepared in a similar manner to Example 134 (c) except that 1-cyclopropylpyrrolidin-3-ol was used.

d) 1-Cyclopropylpyrrolidin-3-ol

The title compound was prepared in a similar manner to J. Med. Pharm. Chem., 1, 73 (1959) except that cyclopropylamine was used.

MS (ES) 128 (M+H)$^+$. $^1$HNMR (CDCl$_3$) 0.4 (m, 2H), 0.95 (m, 3H), 1.65 (m, 2H), 2.0 (br, 1H), 2.2 (m, 2H), 2.5 (m, 1H), 2.9 (m, 1H), 4.35 (m, 1H).

EXAMPLE 149

2-[(Aminocarbonyl)amino]-5-{2-[(2-(4-fluoropiperidin-1-yl)ethoxy]phenyl}-3-thiophenecarboxamide a) The title compound was prepared from 1-[2-(2-bromophenoxy)ethyl]4-fluoropiperidine in a similar manner to Example 9 (e) and the purification was achieved as in Example 134 (a) except that the product was isolated from the dichloromethane phase using cation exchange chromatography eluting with ammonia/methanol mixtures. Final purification was achieved using preparative hplc.

MS (ES) 407 (M+H)$^+$. $^1$H NMR (DMSO-D6) 1.8 (m, 2H), 2.0 (m, 1H), 2.4 (m, 2H), 2.6 (m, 2H), 3.0 (m, 1H), 4.0 (m, 1H), 4.2 (m, 2H), 4.6 (m, 1H), 5.6 (m, 1H), 6.8 (brs, 2H), 6.95 (m, 1H), 7.05 (m, 1H), 7.2 (m, 2H), 7.6 (m, 2H), 7.75 (d, 1H), 10.9 (brs, 1H).

b) 1-[2-(2-Bromophenoxy)ethyl]-4-fluoropiperidine

A mixture of 1-bromo-2-(2-chloroethoxy)benzene (2.35 g), 4-fluoropiperidine hydrochloride (1.54 g), potassium carbonate (4.06 g) and potassium iodide (0.83 g) in dimethylformamide (20 ml) was heated at 80° C. for 18 h. After evaporation, the residue was partitioned between ethyl acetate and water. The solvent phase was washed (brine), dried and evaporated to give an oil (1.0 g).

MS (ES) 302 (M+H)$^+$. $^1$H NMR (CDCl$_3$) 1.9 (m, 2H), 2.2 (m, 2H), 2.8 (m, 2H), 2.9 (m, 1H), 2.95 (m, 1H), 4.2 (m, 2H), 4.7 (m, 2H), 5.75 (m, 1H), 6.8 (m, 2H), 7.2 (m, 1H), 7.55 (m, 1H).

EXAMPLE 150

2-[(Aminocarbonyl)amino]-5-{2-[1-methylpiperidin-4-yl)oxy]phenyl}-3-thiophenecarboxamide a) The title compound was prepared from 4-(2-bromophenoxy)-1-methylpiperidine in a similar manner to Example 9 (e) except that the pure product was obtained by triturating the crude solid with a dichloromethane/methanol mixture.
MS (ES) 375 (M+H)$^+$. $^1$H NMR (DMSO-D6) 1.85 (m, 2H), 2.05 (m, 4H), 2.8 (s, 3H), 3.1 (m, 2H), 4.6 (m, 1H), 6.8 (m, 3H), 7.2 (m, 3H), 7.65 (m, 2H), 7.8 (s, 1H), 10.94 (brs, 1H).

b) 4-(2-Bromophenoxy-1-methylpiperidine
The title compound was prepared from 2-bromophenol and 1-methylpiperidin-4-yl methanesulphonate in a similar manner to Example 134 (b) except that the compound was purified by cation exchange chromatography eluting with ammonia/methanol mixtures.
MS (ES) 270 (M+H)$^+$.

c) 1-Methylpiperidin-4-yl methanesulphonate
The title compound was prepared in a similar manner to Example 134 (c) except that 1-methylpiperidin-4-ol was used.

EXAMPLE 151

2-[(Aminocarbonyl)amino]-5-{2-[(1-methylpyrrolidin-3-yl)oxy]phenyl}-3-thiophenecarboxamide a) The title compound was prepared from 3-(2-bromophenoxy)-1-methylpyrrolidine in a similar manner to Example 9 (e) except that the pure product was obtained by triturating the crude solid with a dichloromethane/methanol mixture.
MS (ES) 361 (M+H)$^+$. $^1$H NMR (DMSO-D6) 1.95 (m, 1H), 2.2 (m, 1H), 2.25 (s, 3H), 2.45 (m, 1H), 2.65 (m, 2H), 2.9 (m, 1H), 5.0 (m, 1H), 6.8 (brs, 2H), 6.95 (m, 2H), 7.2 (m, 2H), 7.6 (dd, 2H), 7.8 (s, 1H), 10.9 (brs, 1H).

b) 3-(2-Bromophenoxy)-1-methylpyrrolidine
The title compound was prepared from 2-bromophenol and 1-methylpyrrolidin-3-yl methanesulphonate in a similar manner to Example 134 (b) except that the compound was purified by cation exchange chromatography eluting with ammonia/methanol mixtures.
MS (ES) 256 (M+H)$^+$. $^1$H NMR(CDCl$_3$) 2.0 (m, 1H), 2.3 (m, 1H), 2.4 (s, 3H), 2.6 (m, 1H), 2.75 (m, 2H), 3.0 (m, 1H), 4.8 (m, 1H), 6.8 (m, 2H), 7.2 (m, 1H), 7.55 (m, 1H).

c) 1-Methylpyrrolidin-3-yl methanesulphonate
The title compound was prepared in a similar manner to Example 134 (c) except that 1-methylpyrrolidin-3-ol was used.

EXAMPLE 152

2-[(Aminocarbonyl)amino]-5-[4-(2-{morpholin-4-yl}acetyl) phenyl]3-thiophenecarboxamide a) The title compound was prepared from 1-(4-bromophenyl)-2-(morpholin-4-yl)ethanone in a similar manner to Example 9 (e).
MS (ES) 389 (M+H)$^+$. $^1$H NMR (DMSO-D6) 2.55 (m, 4H), 3.6 (m, 4H), 3.8 (s, 2H), 6.8 (brs, 1H), 7.0 (brs, 2H), 7.35 (brs, 1H), 7.6 (d, 2H), 7.9 (s, 1H), 8.0 (d, 2H), 11.06 (s, 1H).

b) 1-(4-Bromophenyl)-2-(morpholin-4-yl)ethanone
Morpholine (4.35 g) in dry toluene (8 ml) was stirred during the addition of aliquots of 2-bromo-1-(4-bromophenyl)ethanone (6.95 g) in dry toluene (70 ml). The resulting precipitate was removed by filtration and the filtrate evaporated to give the product (J. Amer. Chem. Soc., 1940, 62, 2882) as a pale yellow solid (7.2 g).
MS (ES) 284 (M+H)$^+$. $^1$H NMR (CDCl$_3$) 2.61 (m, 4H), 3.78 (m, 6H), 7.61 (dd, 2H), 7.90 (dd, 2H).

EXAMPLE 153

2-[(Aminocarbonyl amino]-5-[2-{2-(4-hydroxy-1-piperidinyl)ethoxy}phenyl]-3-thiophenecarboxamide a) The title compound was prepared from 1-[2-(2-bromophenoxy)ethyl]-4-piperidinol in a similar manner to Example 38. Purification by cation exchange chromatography eluting with ammonia/methanol mixtures gave the product (320 mg).
MS (ES) 405 (M+H)$^+$. $^1$H NMR (DMSO-D6) 1.35 (m, 2H), 1.6 (m, 2H), 2.15 (m, 2H), 2.8 (m, 4H), 3.4 (m, 1H), 4.2 (t, 2H), 6.8 (brs, 2H), 7.0 (m, 2H), 7.1 (m, 1H), 7.2 (m, 2H), 7.6 (m, 2H), 7.8 (s, 1H), 11.0 (s, 1H).

b) 1-[2-(2-Bromophenoxy)ethyl]-4-piperidinol
The title compound was prepared from 1-bromo-2-(2-chloroethoxy)benzene and 4-hydroxypiperidine in a similar manner to Example 149 (b).
MS (ES) 300 (M+H)$^+$. $^1$H NMR (CDCl$_3$) 1.6 (m, 2H), 1.75 (brs, 1H), 1.9 (m, 2H), 2.4 (m, 2H), 2.9 (m, 4H), 3.7 (m, 1H), 4.15 (m, 2H), 6.8 (m, 2H), 7.2 (m, 1H), 7.55 (m, 1H).

EXAMPLE 154

2-[(Aminocarbonyl)amino]-5-[2-(2-(2,2,6,6-tetramethylpiperidin-1-yl)ethoxy)phenyl]-3-thiophenecarboxamide a) The title compound was prepared from 1-[2-(2-bromophenoxy)ethyl]-2,2,6,6-tetramethylpiperidine in a similar manner to Example 9 (e).
MS (ES) 445 (M+H)$^+$. $^1$H NMR (DMSO-D6) 1.0 (s, 12H), 1.35 (m, 4H), 1.5 (m, 2H), 3.0 (t, 2H), 3.95 (t, 2H), 6.9 (brs, 2H), 7.0 (m, 1H), 7.3 (m, 2H), 7.4 (s, 1H), 7.6 (m, 2H), 7.8 (m, 1H), 10.95 (brs, 1H).

b) 1-[2-(2-Bromophenoxy)ethyl 2,2,6,6-tetramethylpiperidine
The title compound was prepared from 1-(2-chloroethyl)-2,2,6,6-tetramethylpiperidine hydrochloride and 2-bromophenol in a similar manner to Example 2 (b).
MS (ES) 340 (M+H)$^+$. $^1$H NMR (DMSO-D6) 1.0 (s, 12H), 1.3 (m, 4H), 1.5 (m, 2H), 2.8 (m, 2H), 3.9 (m, 2H), 6.85 (m, 1H), 7.1 (dd, 1H), 7.3 (m, 1H), 7.55 (dd, 1H).

c) 1-(2-Chloroethyl)-2,2,6,6-tetramethylpiperidine hydrochloride
The title compound was prepared as described in J. Med. Chem., 1963, 6, 681.

EXAMPLE 155

2-[(Aminocarbonyl)amino]-5-{2-[2-(3-pyrrolin-1-yl) ethoxy]phenyl}thiophene-3-carboxamide a) The title compound was prepared in a similar manner to Example 9 (e) but using 1-[2-(2-bromophenoxy)ethyl]-3-pyrroline.
MS (ES) 373 (M+H)$^+$. $^1$H NMR (DMSO-D6) 3.1 (t, 2H), 3.5 (s, 4H), 4.2 (t, 2H), 5.8 (s, 2H), 6.9 (s, 2H), 7.0 (t, 1H), 7.15 (d, 1H), 7.2 (m, 2H), 7.6 (m, 2H), 7.8 (s, 1H), 10.9 (s, 1H).

b) 1-[2-(2-Bromophenoxy)ethyl]-3-pyrroline

The title compound was prepared from 3-pyrroline and 2-(2-bromophenoxy)ethyl chloride in a similar manner to Example 42 (b).

MS (ES) 268 (M+H)$^+$. $^1$H NMR (CDCl$_3$) 3.15 (t, 2H) 3.6 s, (4H), 4.2 (t, 2H), 5.8 (s, 2H), 6.8 (t, 1H), 6.9 (d, 1H), 7.25 (m, 1H), 7.5 (m, 1H).

EXAMPLE 156

Cis/trans-2-[(Aminocarbonyl)amino]-5-{2-[2-(2,5-dimethyl-3-pyrrolin-1-yl)ethoxy]phenylthiophene-3-carboxamide a) The title compound was prepared from cis/trans-1-[2-(2-bromophenoxy)ethyl]-2,5-dimethyl-3-pyrroline in a similar manner to Example 9 (e); the product was purified by chromatography on silica using methanol-dichloromethane mixtures.

MS (ES) 401 (M+H)$^+$. $^1$H NMR (DMSO-D6) 1.0–1.1 (m, 6H), 3.15 (m, 2H), 3.7, 3.85 (m, m, 2H), 4.05–4.2 (m, 2H), 5.55, 5.7 (s, s, 2H), 6.8 (s, 2H), 7.0 (t, 1H), 7.15 (d, 1H), 7.25 (m, 2H), 7.6 (m, 2H), 7.7 (s, 1H), 10.9 (s, 1H).

b) cis/trans-1-[2-(2-Bromophenoxy)ethyl]-2,5-dimethyl-3-pyrroline

The title compound was prepared from cis/trans-2,5-dimethyl-3-pyrroline and 2-(2-bromophenoxy)ethyl chloride in a similar manner to Example 42 (b); the product was purified by chromatography on silica using methanolic ammonia/dichloromethane mixtures.

MS (ES) 296 (M+H)$^+$. $^1$H NMR (CDCl$_3$) 1.1–1.2 (m, 6H), 2.9–3.3 (m, 2H), 3.8, 4.0 (m, m, 2H), 4.15, (m, 2H), 5.65, 5.85 (s, s, 2H), 6.8 (t, 1H), 6.9 (d, 1H), 7.25 (m, 1H), 7.5 (m, 1H).

EXAMPLE 157

(2S)-2-[(Aminocarbonyl)amino]-5-4-(2-methoxymethylpyrrolidin-1-ylmethyl)phenyl]thiophene-3-carboxamide The title compound was prepared in a similar manner to Example 103 (b) but starting from (2S)-2-methoxymethylpyrrolidine.

MS ES 389 (M+H)$^+$. $^1$H NMR (DMSO-D6) 1.55 (m, 1H), 1.65 (m, 2H), 1.90 (m, 1H), 2.15 (m, 1H), 2.75 (m, 1H), 2.85 (m, 1H), 3.20–3.45 (m, 6H), 4.10 (m, 1H), 6.90 (s, 2H), 7.30 (m, 3H), 7.50 (d, 2H), 7.65 (m, 2H), 10.95 (s, 1H).

EXAMPLE 158

2-[(Aminocarbonyl)amino]-5-[4-(4-aminocarbonylpiperidin-1-ylmethyl)phenylthiophene-3-carboxamide The title compound was prepared in a similar manner to Example 103 (b) but starting from 4-carboxamidopiperidine.

MS ES 402 (M+H)$^+$. $^1$H NMR (DMSO-D6) 1.55 (m, 2H), 1.65 (m, 2H), 1.90 (m, 2H), 2.05 (m, 1H), 2.80 (m, 2H), 3.40 (s, 2H), 6.70 (s, 1H), 6.95 (s, 2H), 7.20 (s, 1H), 7.30 (m, 3H), 7.45 (d, 2H), 7.65 (m, 2H), 11.00 (s, 1H).

EXAMPLE 159

2-[(Aminocarbonyl)amino]-5-[4-(3-hydroxymethylpiperidin-1-ylmethyl)phenyl]thiophene-3-carboxamide The title compound was prepared in a similar manner to Example 106 but using 3-hydroxymethylpiperidine MS (ES) 389 (M+H)$^+$. $^1$H NMR (DMSO-D6) 0.90 (m, 1H), 1.45 (m, 1H), 1.60 (m, 4H), 1.90 (m, 1H), 2.70 (m, 1H), 2.85 (m, 1H), 3.20 (m, 2H), 3.40 (m, 2H), 4.35 (s, 1H), 6.90 (s, 2H), 7.30 (m, 3H), 7.45 (d, 2H), 7.70 (m, 2H), 11.00 (s, 1H).

EXAMPLE 160

2-[(Aminocarbonyl)amino]-5-[4-(4 hydroxymethylpiperidin-1-methyl phenyl]thiophene 3-carboxamide The title compound was prepared in a similar manner to Example 106 but using 4-hydroxymethylpiperidine.

MS ES 389 (M+H)$^+$. $^1$H NMR (DMSO-D6) 1.15 (m, 2H), 1.35 (m, 1H), 1.60 (m, 2H), 1.85 (m, 2H), 2.80 (m, 2H), 3.20 (m, 2H), 3.40 (s, 2H), 4.35 (t, 1H), 6.90 (s, 2H), 7.30 (m, 3H), 7.45 (d, 2H), 7.65 (m, 2H), 10.95 (s, 1H).

EXAMPLE 161

2-[(Aminocarbonyl)amino]-5-[2-(3-{morpholin-4-yl}pyrrolidin-1-yl)phenyl]thiophene-3-carboxamide a) The title compound was prepared from 4-[1-(2-bromophenyl)pyrrolidin-3-yl]morpholine in a similar manner to Example 9 (e), except that on work-up the reaction mixture was evaporated and the residue sonicated in dichloromethane and aqueous sodium hydrogen carbonate solution. The solvents were decanted off and the residual black gum was dissolved in methanol and purified by cation exchange chromatography, eluting with 0–5% methanol in dichloromethane, then 2–5% ammonia solution (7M in methanol) in dichloromethane. Fractions containing product were evaporated, the residue was triturated with ether and the solid product collected by filtration.

MS (ES) 416 (M+H)$^+$. $^1$H NMR (DMSO-D6) 1.66–1.77 (m, 1H), 1.93–2.03 (m, 1H), 2.27–2.48 (m, 4H), 2.83–3.15 (m, 5H), 3.48–3.62 (m, 4H), 6.83 (brs, 2H), 6.91 (td, 1H), 7.02 (dd, 1H), 7.15–7.23 (m, 2H), 7.30 (dd, 1H), 7.40 (s, 1H), 7.59 (brs, 1H), 10.95 (s, 1H).

b) 4-[1-(2-Bromophenyl)pyrrolidin-3-yl]morpholine 1-(2-Bromophenyl)pyrrolidin-3-ol (1 g) was stirred in toluene (30 ml). Triethylamine (0.69 ml) was added and the solution was cooled in an ice-bath. Methane sulphonyl chloride (0.38 ml) was added dropwise. The reaction mixture was allowed to warm to room temperature over 2 h and stirred for a further 2.5 h. The mixture was filtered, washed through with toluene and the filtrate concentrated to ca. 20 ml in vacuo. Morpholine (10 ml) was then added and the solution stirred at room temperature overnight, a further portion of morpholine (10 ml) was added and the solution was heated at reflux for 24 h. Volatile materials were then removed in vacuo, the residue was diluted with water (40 ml) and extracted with diethyl ether (3×20 ml). The combined extracts were washed with brine, dried (MgSO$_4$), filtered and evaporated. The residue was triturated with isohexane/diethyl ether and product collected by filtration as a yellow solid (0.93 g).

MS (ES) 311 (M+H)+. ¹H NMR(CDCl₃) 1.80–1.95 (m, 1H), 2.10–2.25 (m, 1H), 2.45–2.65 (m, 4H), 2.90–3.05 (m, 1H), 3.18–3.30 (m, 1H), 3.34–3.50 (m, 2H), 3.53–3.66 (m, 1H), 3.70–3.82 (m, 4H), 6.77 (td, 1H), 6.92 (dd, 1H), 7.20 (td, 1H), 7.50 (dd, 1H).

c) 1-(2-Bromophenyl)pyrrolidin-3-ol

2-Bromoaniline (2 g) was heated with 1,4-dibromo-2-butanol (1.58 ml) and diisopropylethylamine (4.9 ml) in toluene (10 ml) at reflux for 20 h. The reaction mixture was allowed to cool, diluted with water (60 ml) and the aqueous phase extracted with ethyl acetate (3×30 ml). The combined extracts were washed with water, brine, dried (MgSO₄), filtered and evaporated. The residue was adsorbed onto silica and purified by column chromatography, eluting with a gradient of 0–20% ethyl acetate in isohexane, to afford the product as a yellow oil (2.30 g).

MS (ES) 242 (M+H)+. ¹H NMR (CDCl₃) 1.89 (d, 1H), 1.91–2.04 (m, 1H), 2.15–2.28 (m, 1H), 3.10–3.21 (m, 1H), 3.29–3.36 (m, 1H), 3.50–3.57 (m, 1H), 3.62–3.73 (m, 1H), 4.46–4.55 (m, 1H), 6.80 (td, 1H), 6.95 (dd, 1H), 7.21 (td, 1H), 7.51 (dd, 1H).

EXAMPLE 162

2-[(Aminocarbonyl)amino]-5-{2-[4-(2-methoxyethyl)piperazin-1-yl]phenyl}thiophene-3-carboxamide a) The title compound was prepared from 1-(2-bromophenyl)-4-(2-methoxyethyl)-piperazine in a similar manner to Example 9 (e), except that on work-up the reaction mixture was evaporated and the residue sonicated in dichloromethane and aqueous sodium hydrogen carbonate solution. The layers were separated and the aqueous phase extracted with a further portion of dichloromethane. The combined organic extracts were evaporated and purified by cation exchange chromatography, eluting with 0–8% methanol in dichloromethane, then 2–6% ammonia solution (7M in methanol) in dichloromethane.

Fractions containing product were evaporated, the residue was triturated with a mixture of methanol and diethyl ether and the solid product collected by filtration.

MS (ES) 404 (M+H)+. ¹H NMR (DMSO-D6) 2.45–2.54 (m, 2H, partially obscured), 2.58–2.68 (m, 4H), 2.76–2.87 (m, 4H), 3.22 (s, 3H), 3.44 (t, 2H), 6.80 (brs, 2H), 7.04–7.23 (m, 4H), 7.52 (d, 1H), 7.61 (brs, 1H), 7.70 (s, 1H), 10.89 (s, 1H).

b) 1-(2-Bromophenyl)-4-(2-methoxyethyl)piperazine

The title compound was prepared in a similar manner to Example 110 (a) but using 1-(2-methoxyethyl)piperazine.

MS (ES) 299 (M+H)+. ¹H NMR (CDCl₃) 2.62–2.75 (m, 6H), 3.05–3.15 (m, 4H), 3.38 (s, 3H), 3.55 (t, 2M), 6.91 (td, 1H), 7.06 (dd, 1H), 7.22–7.30 (m, 1H), 7.55 (dd, 1H).

EXAMPLE 163

2-[(Aminocarbonyl)amino]-5-{2-[(1S, 4S)-2,5-diazabicyclobicyclo [2.2.1]hept-2-yl]phenyl}thiophene-3-carboxamide a) The title compound was prepared from 2-[(aminocarbonyl)amino-5-bromothiophene-3-carboxamide and tert-butyl 5-(2-bromophenyl)-[(1S,4S)-2,5-diazabicyclo[2.2.1] heptane]-2-carboxylate in a similar manner to Example 9 (e). On work-up the product was subjected to cation exchange chromatography, eluting with a gradient of 0–10% methanol in dichloromethane. Product fractions were evaporated and triturated with a mixture of methanol and ether, then collected by filtration. The BOC-protected product was then stirred in 1:10 water: TFA (2 ml) at room temperature for 1 h, evaporated to dryness, redissolved in dichloromethane and purified by cation exchange chromatography, eluting with 0–12% ammonia solution (7M in methanol) in dichloromethane.

MS (ES) 358 (M+H)+. ¹H NMR (DMSO-D6) 1.62 (d, 1H), 1.85 (d, 1H), 2.75 (d, 1H), 2.85 (d, 1H), 3.05 (d, 1H), 3.19 (d, 1H), 3.20 (s, 1H), 3.65 (s, 1H), 4.07 (s, 1H), 6.77–6.95 (m, 3H), 6.97 (d, 1H), 7.10–7.33 (m, 4H), 7.63 (brs, 1H), 11.00 (s, 1H).

b) tert-Butyl 5-(2-bromophenyl)-[(1S, 4S)-2,5-diazabicyclo[2.2.1]heptane]-2-carboxylate The title compound was prepared from 1,2-dibromobenzene and tert-butyl (1S,4S)-(−)-2,5-diazabicyclo[2.2.1]heptane-2-carboxylate in a similar manner to Example 110 (a).

MS (ES) 353 (M+H)+. ¹H NMR (DMSO-D6) 1.46 (s, 9H), 1.82–2.00 (m, 2H), 3.27–3.47 (m, 2H), 3.57–3.89 (m, 2H), 4.33–4.64 (m, 2H), 6.73 (t, 1H), 7.83 (d, 1H), 7.14–7.22 (m, 1H), 7.47–7.56 (m, 1H).

Pharmacological Evaluation of Compounds

IKK-2 Filter Kinase Assay

Compounds were tested for inhibition of IKK-2 using a filter kinase assay. The test compounds were dissolved to 10 mM in dimethylsulphoxide (DMSO). The compounds were then diluted 1 in 40 in kinase buffer (50 mM Tris, pH 7.4 containing 0.1 mM EGTA, 0.1 mM sodium orthovanadate and 0.1% β-mercaptoethanol). 1 in 3 serial dilutions were made from this solution with 2.5% DMSO in kinase buffer. 20 µl of compound dilution was added to wells of a 96 well plate in duplicate. 20 µl 2.5% DMSO in kinase buffer instead of compound was added to control wells (0% inhibition). 20 µl 0.5 M EDTA was added instead of compound to background wells (100% inhibition).

10 µl of a mixture of magnesium acetate, unlabelled ATP, and ³³P-labelled ATP was added to each well made such that the final concentration was 10 mM magnesium acetate, 1 µM ATP and 0.1 µCi ³³P ATP. 20 µl of a mixture of IKK-2 (0.15 µg/well), 1–53 GST-IκB (0.5 µg/well) and bovine serum albumin (BSA) (8.5 µg/well) was added to each well to start the reaction. The final reaction volume was 50 µl.

The kinase reactions were incubated at 21° C. for 80 minutes and the reaction stopped by precipitating the protein by the addition of an equal volume (50 µl) of 20% trichloroacetic acid (TCA). The precipitate was allowed to form for 10 minutes and then filtered onto a GF/C unifilter 96 well plate. Each filter was washed twice with approximately 1 ml 2% TCA. The filter plate was dried at 30–40° C. for 60 minutes, 20 µl scintillant was added to each well and the plate sealed and radioactivity counted on a Packard Topcount microplate scintillation counter.

When tested in the above assay, the compounds of Examples 1 to 163 gave $IC_{50}$ values of less than 10 µM indicating that they are expected to show useful therapeutic activity.

IKK-1 Filter Kinase Assay

The selectivity of compounds was assessed by testing them for inhibition of IKK-1 using a filter kinase assay. The assay conditions were identical to the IKK-2 filter kinase assay except that a mixture of IKK-1 (0.25 µg/well) and 1–53 GST IκB (9 µg/well) was added to each well to start the reaction.

Inhibition of LPS-induced TNFα production by PBMCs

The effect of test compounds on nuclear factor kappa B (NFκB) activation in cells was assessed by measuring inhibition of tumour necrosis factor alpha (TNFα) production by human peripheral blood mononuclear cells (PBMCs) stimulated by bacterial lipopolysaccharide (LPS).

Human blood (250 ml), anticoagulated with heparin, was collected from healthy volunteers. Aliquots of blood (25 ml) were layered on 20 ml Lymphoprep (Nycomed) in 50 ml polypropylene centrifuge tubes. The tubes were centrifuged (Sorval RT600B) at 2,500 rpm for 30 minutes. The cloudy layer containing PBMCs was collected with a fine tipped Pasteur pipette, transferred into 8 clean polypropylene centrifuge tubes (approximately 10 ml per tube) and diluted to 50 ml with phosphate-buffered saline (PBS). These tubes were centrifuged at 2,000 rpm for 8 minutes. PBS (10 ml) was added to each cell pellet and the cells were gently re-suspended. The cells were pooled in 4 centrifuge tubes, PBS was added to each tube to make the volume up to 50 ml and the tubes were centrifuged at 1,400 rpm for 8 minutes. The cell pellets were again re-suspended in 10 ml PBS, pooled in 2 centrifuge tubes, the volume made up to 50 ml with PBS and the tubes centrifuged at 900 rpm for 10 minutes.

The final cell pellets were gently re-suspended in 10 ml tissue culture medium (RPMI containing 1% heat-inactivated human serum, L-glutamine and penicillin and streptomycin), combined into 1 tube and the volume made up to 30 ml with RPMI medium. The cells were counted and the cell suspension was diluted to $2.6 \times 10^6$ cells/ml.

Test compounds were dissolved in DMSO to 10 mM and diluted 1 in 250 (40 μM) with RPMI medium. The compounds were then serially diluted 1 in 3 with 0.4% DMSO in RPMI medium. Aliquots of test compound dilutions (50 μl) were transferred to the wells of a 96-well plate. Control wells contained 0.4% DMSO in RPMI instead of compound.

Aliquots of the cell suspension (100 μl) were added to each well and the plates incubated at 37° C. for 30 minutes. 50 μl of 40 μg/ml LPS (Sigma, L-4130) was added to wells to stimulate INFa production by the cells and the plates were incubated overnight at 37° C. RPMI medium (50 μl) was added to negative control wells instead of LPS. The final incubation volume was 200 μl.

Plates were centrifuged for 4 minutes at 1,200 rpm and supernatants were removed for measurement of TNFα concentration. Viability of the remaining cell pellet was measured using WST-1 reagent (Boehringer Mannheim, 1044807). 100 μl RPMI medium containing 10 μl WST-1 reagent was added to each well and the plates were incubated for 0.5 to 3 h. The absorbance at 450 nm was then measured using a 96-well plate spectrophotometer.

TNFα in the supernatants (freshly harvested or stored frozen at −20° C.) were measured using an enzyme-linked immunosorbant assay (ELISA). The ELISA plate was prepared by coating the wells of a 96 well plate with a sheep anti-human TNFα monoclonal antibody (100 μl of 1 μg/ml antibody diluted in coating buffer; 0.5 M carbonate/bicarbonate buffer, pH 9.6 containing 0.2 g/l sodium azide) and incubating overnight at 4° C. Blank wells were not coated. The wells were washed once with 0.1% BSA in PBS containing 0.05% Tween (PBS/Tween) then incubated for 1 h at room temperature with 1% BSA in coating buffer (200 μl). The wells were then washed 3 times with 0.1% BSA in PBS/Tween.

The samples of supernatant from the PBMC incubation were diluted 1 in 3 with 1% BSA in PBS/Tween. 100 μl aliquots of these dilutions were added to the ELISA plate.

Other wells contained 100 μl TNFα standard (10, 3.3, 1.1, 0.37, 0.12, 0.04, 0.014 and 0 ng/ml). The ELISA plate was incubated at room temperature for 2 h before the wells were washed 3 times with 0.1% BSA in PBS/Tween. A rabbit anti-human TNFα antibody (100 μl of a 2.5 μg/ml solution) was added to each well and the plate incubated at room temperature for 1.5 h. The wells were then washed 3 times with 0.1% BSA in PBS/Tween. Goat anti-rabbit IgG-horse radish peroxidase conjugate (ICN, 674371; 100 μl of a 1 in 10,000 dilution) was added to each well and the plate incubated at room temperature for 1.5 h. The wells were washed 3 times with 0.1% BSA in PBS/Tween.

Peroxidase substrate was prepared by dissolving a 1 mg TMB tablet (Sigma, T-5525) in 100 μl DMSO (100 μl) and adding this and 36 μl UHPO (BDH, 30559; 1 g tablet dissolved in 25 ml distilled water) to 10 ml 0.1 M citrate/aceate buffer, pH6. 100 μl substrate was added to each well and the plate incubated in the dark at room temperature for approximately 30 minutes. The reaction was stopped by adding 25 μM sulphuric acid to each well. The absorbance at 450 nm was measured in a 96 well plater spectrophotometer.

The invention claimed is:

1. A compound of formula (I)

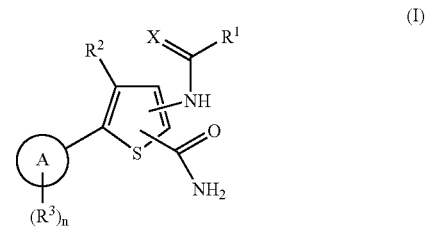

in which:

$R^1$ represents $NH_2$;

X represents O;

$R^2$ represents hydrogen, halogen, cyano, nitro, —$NR^6R^7$, $C_1$–$C_2$ alkyl, or trifluoromethyl;

A represents a pyridyl group; said pyridyl group being optionally substituted by one or more substituents selected independently from halogen, cyano, nitro, —$NR^8R^9$, —$CONR^8R^9$, —$COOR^8$, —$NR^8COR^9$, —$S(O)_sR^8$, —$SO_2NR^8R^9$, —$NR^8SO_2R^9$, $C_1$–$C_6$ alkyl, trifluoromethyl, —$(CH_2)_tR^{10}$, —$O(CH_2)_tR^{11}$ or —$OR^{12}$;

n represents an integer 1 or 2; and when n represents 2, each $R^3$ group may be selected independently;

$R^3$ represents a group —W—Y—Z wherein:

W represents O or S;

Z represents a bond;

Z represents:

(a) a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, —$NR^{16}R^{17}$, —$CONR^{16}R^{17}$, —$COOR^{16}$—$COR^{16}$—$NR^{16}COR^{17}$, —$S(O)_uR^{16}$, —$SO_2NR^{16}R^{17}$, —$NR^{16}SO_2R^{17}$, hydroxyl, $C_2$–$C_6$ alkenyl, $C_2$–$C_6$ alkynyl, $C_1$–$C_6$ alkyl and $C_1$–$C_6$ alkoxy; said alkyl or alkoxy group being optionally further substituted by one or more groups selected from halogen, cyano, hydroxyl, $C_1$–$C_4$ alkoxy and $NR^{18}R^{19}$; or (b) a 3- to 8-membered saturated or partially unsaturated monocyclic or saturated bicyclic ring system optionally incorporating one or two heteroatoms selected independently from O, N and S, and optionally incorporating a carbonyl group; said ring system being optionally substituted by one or more substituents selected independently from halogen, cyano, $-NR^{16}R^{17}$, $-CONR^{16}R^{17}$, $-COOR^{16}$, $-COR^{16}$, $-NR^{16}COR^{17}$, $-S(O)_uR^{16}$, $-SO_2NR^{16}R^{17}$, $-NR^{16}SO_2R^{17}$, hydroxyl, $C_2-C_6$ alkenyl, $C_2-C_6$ alkynyl, $C_1-C_6$ alkyl, $C_3-C_6$ cycloalkyl and $C_1-C_6$ alkoxy; said alkyl or alkoxy group being optionally further substituted by one or more groups selected from halogen, cyano, hydroxyl, $C_3-C_6$ cycloalkyl, $C_1-C_4$ alkoxy and $NR^{18}R^{19}$; provided that said saturated monocyclic ring Z is not bonded to Y through nitrogen if the group $-W-Y-$ represents $-(CH_2)_{2-4}-$ or $-O-(CH_2)_{2-4}-$ when the saturated ring Z is also unsubstituted; or (c) if W represents O, then Z may also represent hydroxyl, $CF_3$, $CHF_2$ or $CH_2F$, cyclopentylmethyl, $CH_2CHF_2$, tetrahydro-2-furanylmethyl, 2-furanylmethyl, 2-thienylmethyl, tetrahydro-3-furanyl, cyclopropylmethyl, benzyloxyethyl, tereohydro-2-furanyl, benzyl, 2-(1-pyrrolidin-2-one)ethyl, 1-methylpyrrolidin-2-on-4-yl) methyl, or 2,2-dimethyl-3-pyrrolidinyl-propyl, provided that the group $-Y-Z$ does not thereby represent $-O-(CH_2)_{2-4}-OCH_3$;

$R^{10}$ and $R^{11}$ independently represent $NR^{20}R^{21}$ where $R^{20}$ and $R^{21}$ are independently hydrogen or $C_1-C_6$ alkyl optionally substituted by $C_1-C_4$ alkoxy; or the group $NR^{20}R^{21}$ represents a 5- or 6-membered saturated azacyclic ring optionally containing a further O, S or $NR^{22}$ group; where $R^{22}$ is hydrogen or $C_1-C_6$ alkyl; or $R^{10}$ and $R^{11}$ independently represent $C_1-C_6$ alkoxy;

$R^4$ and $R^5$ independently represent H or $C_1-C_4$ alkyl; or the group $NR^4R^5$ represents a 5- or 6-membered saturated azacyclic ring optionally containing a further O, S or $NR^{23}$ group; where $R^{23}$ is hydrogen or $C_1-C_4$ alkyl;

$R^6$ and $R^7$ independently represent H or $C_1-C_2$ alkyl;

$R^8$, $R^9$ and $R^{12}$ independently represent H or $C_1-C_6$ alkyl;

$R^{16}$ and $R^{17}$ independently represent H or $C_1-C_6$ alkyl optionally substituted by OH, $C_1-C_4$ alkoxy or one or more fluoro atoms; or the group $NR^{16}R^{17}$ represents a 5- or 6-membered saturated azacyclic ring optionally containing a further O, S or $NR^{24}$ group; where $R^{24}$ is hydrogen or $C_1-C_6$ alkyl optionally substituted by OH, $C_1-C_4$ alkoxy or one or more fluoro atoms;

$R^{18}$ and $R^{19}$ independently represent H or $C_1-C_4$ alkyl; or the group $NR^{18}R^{19}$ represents a 5- or 6-membered saturated azacyclic ring optionally containing a further O, S or $NR^{25}$ group; where $R^{25}$ is hydrogen or $C_1-C_4$ alkyl;

m, s, u and v independently represent an integer 0, 1 or 2;

t represents an integer 2, 3 or 4;

and pharmaceutically acceptable salts thereof:

with the proviso that the following two compounds are excluded:

2-[(aminocarbonyl)amino]-5-(4-[2-(1-(2,2,6,6-tetramethyl)piperidinyl)ethoxy]phenyl)-3-thiophenecarboxamide;

2-[(aminocarbonyl)amino]-5-(4-(thiazol-4-yl-methoxy)phenyl)-3-thiophenecarboxamide.

2. A compound of formula (I), according to claim 1, in which $R^2$ represents H.

3. A compound of formula (I), according to claim 1, in which W represents O.

4. A compound of formula (I), according to claim 1, selected from:
- 2-[(aminocarbonyl)amino]-5-[6-(2,2-difluoroethoxy)pyridin-3-yl]-3-thiophenecarboxamide;
- 2-[(aminocarbonyl)amino]-5-[6-(cyclopentyloxy)pyridin-3-yl]-3-thiophenecarboxamide;
- 2-[(aminocarbonyl)amino]-5-[6-[(tetrahydrofuran-2-yl)methoxy]pyridin-3-yl]-3-thiophenecarboxamide;
- 2-[(aminocarbonyl)amino]-5-{3-[6-(furan-2-yl-methoxy)]-pyridine}-3-thiophenecarboxamide;
- (R)-2-[(aminocarbonyl)amino]-5-{3-[6-(tetrahydrofuran-3-yloxy)]-pyridine)}-3-thiophenecarboxamide;
- 2-[(aminocarbonyl)amino]-5-{3-[6-(1-isopropyl-pyrrolidin-3-yloxy)]-pyridine}-3-thiophenecarboxamide;
- 2-[(aminocarbonyl)amino]-5-{3-[6-(1-t-butyloxycarbonyl-piperidin-4-yloxy)]-pyridine)}-3-thiophenecarboxamide;
- 2-[(aminocarbonyl)amino]-5-{3-[6-(piperidin-4-yloxy)]-pyridine}-3-thiophenecarboxamide;
- 2-[(aminocarbonyl)amino]-5-{3-[6-(1-(2-methoxyethyl)-piperidin-4-yloxy)]-pyridine}-3-thiophenecarboxamide;
- 2[(aminocarbonyl)amino]-5-{3-[6-(N-methanesulphonyl)-piperidin-4-yloxy]-pyridine}-3-thiophenecarboxamide;
- 2-[(aminocarbonyl)amino]-5-{3-[6-(thien-2-ylmethoxy)]pyridine}-3-thiophenecarboxamide;
- 2-[(aminocarbonyl)amino]-5-{3-[6-(cyclopentylmethoxy)]pyridine}-3-thiophenecarboxamide;
- 2-[(aminocarbonyl)amino]-5-[3-(6-benzyloxy)pyridine]-3-thiophenecarboxamide;
- 2-[(aminocarbonyl)amino]-5-{3-[6-(tetrahydrofuran-3-yloxy)]pyridine}-3-thiophenecarboxamide;
- 2-[(aminocarbonyl)amino]-5-{3-[6-(tetrahydrofuran-3-ylmethoxy)]pyridine}-3-thiophenecarboxamide;
- 2-[(aminocarbonyl)amino]-5-{3-[6-(cyclopropylmethoxy)]pyridine}-3-thiophenecarboxamide;
- (S)-2-[(aminocarbonyl)amino]-5-{3-[6-(tetrahydrofuran-3-yloxy)]pyridine}-3-thiophenecarboxamide;
- 2-[(aminocarbonyl)amino]-5-{3-[6-(tetrahydropyran-4-yloxy)]pyridine}-3-thiophenecarboxamide;
- 2-[(aminocarbonyl)amino]-5-{3-[6-(tetrahydrothiopyran-3-yloxy)]pyridine}-3-thiophenecarboxamide;
- 2-[(aminocarbonyl)amino]-5-{3-[6-(1-isopropylazetidin-3-yloxy)]pyridine}-3-thiophenecarboxamide;
- 2-[(aminocarbonyl)amino]-5-{3-[6-(benzyloxy-2-ethoxy)]pyridine}-3-thiophenecarboxamide;
- 2-[(aminocarbonyl)amino]-5-{3-[6-(N-methylpiperidin-3-yloxy)]pyridine}-3-thiophenecarboxamide;
- 2-[(aminocarbonyl)amino]-5-{3-[6-(2-(1-pyrrolidin-2-one)ethoxy)]pyridine}-3-thiophenecarboxamide;
- 2-[(aminocarbonyl)amino]-5-[6-{(1-methylpyrrolidin-2-on-4-yl)methoxy}pyridin-3-yl]-3-thiophenecarboxamide;
- 2-[(aminocarbonyl)amino]-5-[6-(2,2-dimethyl-3-pyrrolidinylpropoxy)pyridin-3-yl]-3-thiophenecarboxamide; and
- 2-[(aminocarbonyl)amino]-5-[(6-cyclopropylmethylthio)pyridin-3-yl]-3-thiophenecarboxamide;

or pharmaceutically acceptable salts thereof.

5. A process for the preparation of a first compound of formula (I), according to claim 1, which comprises:

(a) reaction of a compound of formula (II):

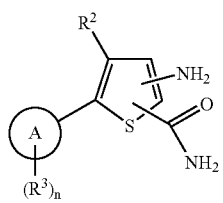

(II)

with an isocyanate or an isothiocyanate or an acyl derivative, $R^1$—CO—L where L is a leaving group, to produce the first compound of formula (I); or (b) reaction of compound of formula (III)

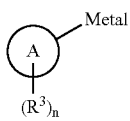

(III)

with a compound of formula (IV)

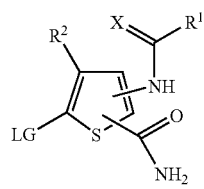

(IV)

and LG represents a leaving group, to produce the first compound of formula (I); or (c) reaction of compound of formula (V)

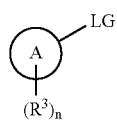

(V)

and LG represents a leaving group, with a compound of formula (VI)

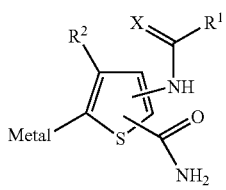

(VI)

to produce the first compound of formula (I);

and where necessary converting the first compound of formula (I), or another salt thereof, into a pharmaceutically acceptable salt thereof; or converting the first compound of formula (I) into a second compound of formula (I); and where desired converting the first compound of formula (I) into an optical isomer thereof.

6. A pharmaceutical composition comprising a compound of formula (I), or a pharmaceutically acceptable salt thereof; as claimed in claim 1 in association with a pharmaceutically acceptable adjuvant, diluent or carrier.

7. A process for the preparation of a pharmaceutical composition as claimed in claim 6 which comprises mixing a compound of formula (I), or a pharmaceutically acceptable salt thereof, with a pharmaceutically acceptable adjuvant, diluent or carrier.

8. A method of treatment of a patient having an inflammatory disease selected from the group consisting of asthma, rheumatoid arthritis, multiple sclerosis, and chronic obstructive pulmonary disease, the method comprising:

administering to a person suffering from said inflammatory diseases a therapeutically effective amount of a compound of formula (I), or a pharmaceutically acceptable salt thereof, as claimed in claim 1.

9. The method as claimed in claim 8 wherein the inflammatory disease is asthma.

10. The method as claimed in claim 8 wherein the inflammatory disease is rheumatoid arthritis.

11. The method as claimed in claim 8 wherein the inflammatory disease is multiple sclerosis.

12. The method as claimed in claim 8 wherein the inflammatory disease is chronic obstructive pulmonary disease.

* * * * *